(12) United States Patent
Wogoman et al.

(10) Patent No.: US 8,986,390 B2
(45) Date of Patent: Mar. 24, 2015

(54) METHOD OF TRIALING A KNEE PROSTHESIS

(75) Inventors: Thomas E. Wogoman, Warsaw, IN (US); Jon M. Edwards, Warsaw, IN (US); Duncan G. Young, Hebden Bridge West (GB); Liam T. Dower, Ely (GB); Rusty T. Meier, Warsaw, IN (US); David W. Waite, II, Warsaw, IN (US); Rebecca L. Chaney, Warsaw, IN (US); Michael J. Rock, Leeds (GB); Matthew S. Wallace, Huntertown, IN (US); David C. Pollock, Lewisville, NC (US); Scott M. Thomas, Fort Wayne, IN (US)

(73) Assignee: DePuy (Ireland) (IE)

( * ) Notice: Subject to any disclaimer, the term of this patent is extended or adjusted under 35 U.S.C. 154(b) by 98 days.

(21) Appl. No.: 13/530,771

(22) Filed: Jun. 22, 2012

(65) Prior Publication Data

US 2013/0006371 A1 Jan. 3, 2013

Related U.S. Application Data

(60) Provisional application No. 61/503,311, filed on Jun. 30, 2011.

(51) Int. Cl.
*A61F 2/38* (2006.01)
*A61B 17/17* (2006.01)
*A61F 2/46* (2006.01)

(52) U.S. Cl.
CPC .............. *A61F 2/4684* (2013.01); *A61F 2/389* (2013.01); *A61B 17/1764* (2013.01); *A61F 2/461* (2013.01)
USPC .................. 623/20.15; 623/20.16; 623/20.28; 623/20.29; 623/20.33

(58) Field of Classification Search
USPC .................... 623/20.14–20.16, 20.28–20.29, 623/20.32–20.33
See application file for complete search history.

(56) References Cited

U.S. PATENT DOCUMENTS

| D269,547 S | 6/1983 | Rosenthal |
| 4,659,331 A | 4/1987 | Matthews et al. |

(Continued)

FOREIGN PATENT DOCUMENTS

| EP | 1219269 A1 | 7/2002 |
| EP | 1415625 A2 | 3/2004 |

(Continued)

OTHER PUBLICATIONS

Coordinate Ultra Revision Knee System, Surgical Technique, 1997, p. 24.

(Continued)

*Primary Examiner* — Randy Shay
(74) *Attorney, Agent, or Firm* — Barnes & Thornburg LLP

(57) ABSTRACT

A method of trialing prosthetic components of a knee prosthesis including positioning a femoral trial component on a surgically-prepared distal end of a patient's femur, assembling a tibial bearing trial component, and positioning the tibial bearing trial component on a tibial base trial component seated on a surgically-prepared proximal end of a patient's tibia. The method may also include adjusting the patient's leg with the tibial bearing trial component engaging the femoral trial component, and readjusting the patient's leg with the tibial bearing trial component engaging the femoral trial component after positioning the tibial bearing trial component on the tibial base trial component and a keel punch.

18 Claims, 36 Drawing Sheets

(56) References Cited

U.S. PATENT DOCUMENTS

| | | | |
|---|---|---|---|
| D338,270 S | 8/1993 | Stephens et al. |
| 5,306,276 A | 4/1994 | Johnson et al. |
| 5,356,414 A | 10/1994 | Cohen et al. |
| 5,364,401 A | 11/1994 | Ferrante et al. |
| 5,486,178 A | 1/1996 | Hodge |
| 5,514,143 A | 5/1996 | Bonutti et al. |
| 5,540,696 A | 7/1996 | Booth et al. |
| 5,569,260 A | 10/1996 | Petersen |
| 5,597,379 A | 1/1997 | Haines et al. |
| 5,601,565 A | 2/1997 | Huebner |
| 5,611,802 A | 3/1997 | Samuelson et al. |
| 5,643,272 A | 7/1997 | Haines et al. |
| 5,649,928 A | 7/1997 | Grundei |
| 5,683,469 A | 11/1997 | Johnson et al. |
| 5,690,636 A | 11/1997 | Wildgoose et al. |
| 5,702,464 A | 12/1997 | Lackey et al. |
| 5,704,941 A | 1/1998 | Jacober et al. |
| 5,709,689 A | 1/1998 | Ferrante et al. |
| 5,720,752 A | 2/1998 | Elliott et al. |
| 5,735,904 A | 4/1998 | Pappas |
| 5,749,876 A | 5/1998 | Duvillier et al. |
| 5,769,854 A | 6/1998 | Bastian et al. |
| 5,788,700 A | 8/1998 | Morawa et al. |
| 5,860,980 A | 1/1999 | Axelson et al. |
| 5,935,128 A | 8/1999 | Carter et al. |
| 5,976,147 A | 11/1999 | Lasalle et al. |
| 5,989,261 A | 11/1999 | Walker et al. |
| 6,022,377 A | 2/2000 | Nuelle et al. |
| 6,024,746 A | 2/2000 | Katz et al. |
| 6,102,955 A | 8/2000 | Mendes et al. |
| 6,159,216 A | 12/2000 | Burkinshaw et al. |
| 6,344,043 B1 | 2/2002 | Pappas |
| 6,355,045 B1 | 3/2002 | Gundlapalli et al. |
| 6,478,799 B1 | 11/2002 | Williamson |
| 6,485,521 B1 | 11/2002 | Say et al. |
| 6,663,636 B1 | 12/2003 | Lin |
| 6,712,824 B2 | 3/2004 | Millard et al. |
| 6,821,470 B2 | 11/2004 | Gundlapalli et al. |
| D518,178 S | 3/2006 | Christiansen |
| 7,104,996 B2 | 9/2006 | Bonutti |
| 7,291,174 B2 | 11/2007 | German et al. |
| 7,344,541 B2 | 3/2008 | Haines et al. |
| 7,695,519 B2 | 4/2010 | Collazo |
| D619,251 S | 7/2010 | Justiniano-Garcia et al. |
| 8,187,283 B2 * | 5/2012 | Thomas | 606/102 |
| D666,713 S | 9/2012 | Waite et al. |
| 8,551,179 B2 * | 10/2013 | Jones et al. | 623/20.35 |
| 2002/0082607 A1 * | 6/2002 | Heldreth et al. | 606/102 |
| 2004/0039450 A1 | 2/2004 | Griner et al. |
| 2005/0075640 A1 | 4/2005 | Collazo et al. |
| 2006/0089641 A1 | 4/2006 | Collazo |
| 2006/0184176 A1 | 8/2006 | Straszheim-Morley et al. |
| 2007/0233137 A1 | 10/2007 | Seo et al. |
| 2008/0119938 A1 | 5/2008 | Oh |
| 2008/0147075 A1 | 6/2008 | Bonutti |
| 2008/0154270 A1 | 6/2008 | Haines et al. |
| 2008/0221569 A1 | 9/2008 | Moore et al. |
| 2008/0269901 A1 | 10/2008 | Baynham et al. |
| 2009/0076514 A1 | 3/2009 | Haines |
| 2009/0082773 A1 | 3/2009 | Haines |
| 2009/0125114 A1 | 5/2009 | May et al. |
| 2009/0138018 A1 | 5/2009 | Haines |
| 2010/0016979 A1 | 1/2010 | Wyss et al. |
| 2010/0076438 A1 | 3/2010 | Correia et al. |
| 2010/0082111 A1 | 4/2010 | Thomas |
| 2010/0125337 A1 | 5/2010 | Grecco et al. |
| 2010/0298941 A1 * | 11/2010 | Hes et al. | 623/17.16 |
| 2011/0066246 A1 | 3/2011 | Ries et al. |
| 2011/0178605 A1 | 7/2011 | Auger et al. |
| 2012/0041566 A1 | 2/2012 | Lenz et al. |
| 2012/0158152 A1 * | 6/2012 | Claypool et al. | 623/20.33 |
| 2012/0323334 A1 | 12/2012 | Jones et al. |
| 2013/0006252 A1 | 1/2013 | Waite, II et al. |
| 2013/0006253 A1 | 1/2013 | Waite, II et al. |
| 2013/0006370 A1 | 1/2013 | Wogoman et al. |
| 2013/0006377 A1 | 1/2013 | Waite, II et al. |

FOREIGN PATENT DOCUMENTS

| | | |
|---|---|---|
| EP | 1836997 A1 | 9/2007 |
| EP | 2168537 A1 | 3/2010 |
| WO | 9925263 A1 | 3/1999 |
| WO | 0013597 A1 | 3/2000 |
| WO | 2008054389 A | 5/2008 |
| WO | 2011073632 A1 | 6/2011 |

OTHER PUBLICATIONS

GMK Revision, Surgical Technique, Ref. 99.27.12US rev. 1, 1999, 74 pages.

P.F.C. Sigma Knee System, Revision, Surgical Technique, 2000, p. 66.

P.F.C. Sigma Rotating Platform Knee System with M.B.T. Tray, Primary Procedure with a Curved or Posterior Stabilized Implant, 2003, 43 pages.

Smith & Nephew, Legion, Revision Knee System, Surgical Technique, 2005, 40 pages.

PFC Sigma RP-F, Specialist 2 Instruments, Surgical Technique, Performance in Flexion, 2007, 32 pages.

Sigma High Performance Instruments, Design Rationale, 2007, 12 pages.

Biomet, Vanguard SSK, Revision System, Surgical Technique, Feb. 2008, 64 pages.

LCS High Performance Instruments, Surgical Technique, 2008, 44 pages.

DePuy Orthopaedics, Inc., Sigma Revision and M.B.T. Revision Tray, Surgical Technique, 2008, 82 pages.

Zimmer NexGen LCCK, Surgical Technique for use with LCCK 4-in-1 Instrument, 2009, 52 pages.

Sigma High Performance Instruments, Classic Surgical Technique, 2010, 52 pages.

Sigma Revision and M.B.T. Revision Tray, Surgical Technique, 2012, p. 84.

S-Rom Noiles Rotating Hinge, Surgical Technique, 2012, p. 76.

Declaration of Thomas E. Wogoman (with Exhibits A-I), executed Aug. 11, 2014, 145 pages.

* cited by examiner

METHOD OF TRIALING A KNEE PROSTHESIS

This application claims priority under 35 U.S.C. §119 to U.S. Patent Application No. 61/503,311, which was filed on Jun. 30, 2011 and is incorporated herein by reference.

CROSS-REFERENCE

Cross-reference is made to co-pending U.S. Provisional Patent Application Ser. No. 61/503,303 entitled "METHOD OF USING A TRIALING SYSTEM FOR A KNEE PROSTHESIS" by Tom Wogoman et al.; and co-pending U.S. Provisional Patent Application Ser. No. 61/503,300 entitled "TRIALING SYSTEM FOR A KNEE PROSTHESIS" by Tom Wogoman et al., each of which is assigned to the same assignee as the present application, each of which is filed concurrently herewith, and each of which is hereby incorporated by reference.

TECHNICAL FIELD

The present disclosure relates generally to orthopaedic surgical instruments and, more particularly, to surgical instruments used with a patient's tibia.

BACKGROUND

Joint arthroplasty is a well-known surgical procedure by which a diseased and/or damaged natural joint is replaced by a prosthetic joint. A typical knee prosthesis includes a patella prosthetic component, a tibial tray, a femoral component, and a polymer insert or bearing positioned between the tibial tray and the femoral component. Femoral components are designed to be attached to a surgically-prepared distal end of a patient's femur. Tibial trays are designed to be attached to a surgically-prepared proximal end of a patient's tibia.

To facilitate the replacement of the natural joint with the knee prosthesis, orthopaedic surgeons use a variety of orthopaedic surgical instruments such as, for example, prosthetic trial components, cutting blocks, drill guides, milling guides, and other surgical instruments. Prosthetic trial components, such as, for example, a femoral trial component and a tibial bearing trial component, are used to size and select the components of the knee prosthesis that will replace the patient's natural joint. A procedure that utilizes the trial components to size and select the components of the knee prosthesis is often referred to as a trial reduction.

SUMMARY

According to one aspect of the disclosure, an orthopaedic surgical instrument system includes an orthopaedic surgical instrument adapted to be positioned on a surgically-prepared proximal end of a patient's tibia. The orthopaedic surgical instrument includes a central post that defines a longitudinal axis. The system also includes a tibial bearing trial assembly coupled to the orthopaedic surgical instrument. The tibial bearing trial assembly includes one of a plurality of tibial bearing surface trial components, each tibial bearing surface trial component having an articular surface, and a shim. The shim is configured to be coupled to a first tibial bearing surface trial component of the plurality of tibial bearing surface trial components in a first orientation in which the tibial bearing trial assembly is permitted to pivot about the axis. The shim is configured to be coupled to a second tibial bearing surface trial of the plurality of tibial bearing surface trial components in a second orientation in which the tibial bearing trial assembly is substantially prevented from rotating about the longitudinal axis.

In some embodiments, the shim may have an aperture defined therein. The aperture may include a central passageway sized to receive the central post, a first slot extending from the central passageway, and a second slot extending from the central passageway. In some embodiments, a lug may extend from the central post. The lug may be received in the first slot when the shim is positioned over the central post in the first orientation and received in the second slot when the shim is positioned over the central post in the second orientation.

In some embodiments, the orthopaedic surgical instrument may include a tibial base trial component adapted to be positioned on the surgically-prepared proximal end of the patient's tibia. The tibial base trial component may have an upper surface configured to contact the shim when the tibial bearing trial assembly is coupled to the orthopaedic surgical instrument. Additionally, in some embodiments, the orthopaedic surgical instrument may include a base insert adapted to be positioned in an opening defined in the tibial base trial component. The base insert may have the central post extending therefrom.

In some embodiments, the orthopaedic surgical instrument may include a keel punch adapted to be positioned in an opening defined in the tibial base trial component. The keel punch may include a main platform having the central post extending upwardly therefrom, and a pair of arms extending outwardly from the main platform. The pair of arms may be configured to be positioned in the surgically-prepared proximal end of the patient's tibia.

In some embodiments, each tibial bearing surface trial component may include a pair of pegs extending downwardly therefrom, and the shim may include a pair of attachment openings. Each attachment opening may be sized to receive one of the pair of pegs to removably couple each tibial bearing surface trial component to the shim.

According to another aspect, an orthopaedic surgical instrument system includes an orthopaedic surgical instrument having a central post defining a longitudinal axis, and a shim including an aperture configured to receive the central post. The shim is configured to be positioned on the orthopaedic surgical instrument in a first orientation in which the shim is permitted to pivot about the longitudinal axis, and a second orientation in which the shim is prevented from rotating about the longitudinal axis. In some embodiments, the aperture may include a central passageway sized to receive the central post of the orthopaedic surgical instrument, and a slot extending from the central passageway. The slot may be defined by an arcuate inner wall extending between a pair of planar inner walls. In some embodiments, the arcuate inner wall may define an arc extending approximately fifty degrees.

In some embodiments, the orthopaedic surgical instrument may include a lug extending from the central post. The lug may be configured to be received in the slot when the shim is positioned on the orthopaedic surgical instrument in the first orientation such that when the shim is pivoted in a first direction about the longitudinal axis, a first planar inner wall of the pair of planar inner walls is advanced into contact with the lug, and when the shim is pivoted in a second direction about the longitudinal axis, a second planar inner wall of the pair of planar inner walls is advanced into contact with the lug.

In some embodiments, the aperture of the shim may include a second slot extending from the central passageway, and the lug may be received in the second slot when the shim is positioned on the orthopaedic surgical instrument in the second orientation. In some embodiments, the second slot may be defined by a pair of inner walls configured to engage the lug when the lug is received in the second slot such that the shim is substantially prevented from rotating about the longitudinal axis.

In some embodiments, the system may further include a tibial bearing surface trial component including an articular surface configured to contact a pair of femoral condyles and a bottom surface having a pair of pegs extending downwardly therefrom. The shim may include a pair of attachment openings. Each attachment opening may be sized to receive one of the pair of pegs to removably couple the tibial bearing surface trial component to the shim.

Additionally, in some embodiments, the tibial bearing surface trial component may be permitted to be secured to the shim when the shim is positioned in the first orientation and prevented from being secured to the shim when the shim is positioned in the second orientation. In some embodiments, the pair of pegs may include a first peg and a second peg having a peg size different from the first peg, and the pair of attachment openings may include a first attachment opening sized to receive the first peg and a second attachment opening sized to the receive the second peg. The second attachment opening may have an opening size different from the first attachment opening and configured to match the peg size of the second peg.

According to another aspect, an orthopaedic surgical instrument includes a tibial trial shim including a plate having a predetermined thickness. The plate has an aperture defined therein that includes a central passageway, a rectangular slot extending from a first side of the central passageway, and an arcuate slot extending from a second side of the central passageway.

In some embodiments, the plate may have a pair of attachment openings defined therein. Each attachment opening may be configured to secure the tibial trial shim to a tibial bearing surface trial component. In some embodiments, a first attachment opening of the pair of attachment openings may be defined through the plate on the first side of the central passageway, a second attachment opening of the pair of attachment openings may be defined through the plate on the second side of the central passageway, and the first attachment opening may have a different size from the second attachment opening.

Additionally, in some embodiments, the first attachment opening and the second attachment opening may be circular, and the diameter of the first attachment opening may be greater than the diameter of the second attachment opening.

In some embodiments, the orthopaedic surgical instrument may further include a plurality of tibial bearing surface trial components configured to be removably coupled to the tibial trial shim. Each tibial bearing surface trial component may have an upper bearing surface configured to contact a pair of femoral condyles and a bottom surface having a pair of pegs extending therefrom. The first attachment opening of the tibial trial shim may be sized to receive a first peg of the pair of pegs and the second attachment opening of the tibial trial shim may be sized to the receive a second peg of the pair of pegs.

In some embodiments, the plate may include a first planar surface, a second planar surface, and a sidewall extending between the first planar surface and the second planar surface. A first channel may be defined in the first planar surface. The first channel may extend inwardly from the sidewall toward the aperture. A second channel may be defined in the second planar surface. The second channel may extend inwardly from the sidewall toward the aperture.

In some embodiments, the aperture may be positioned between the first channel and the second channel. In some embodiments, the aperture may include a slot extending from the central passageway through a posterior section of the sidewall. In some embodiments, the central passageway may define an axis through the plate, and the arcuate slot may be defined by an arcuate inner wall having an edge that extends approximately fifty degrees about the axis. In some embodiments, the arcuate slot may be further defined by a pair of planar inner walls and the arcuate inner wall may extend between the pair of planar inner walls.

According to another aspect, a method of trialing prosthetic components of a knee prosthesis is disclosed. The method includes positioning a tibial base trial component on a surgically-prepared proximal end of a patient's tibia, and inserting a base insert into an opening defined in the tibial base trial component. The base insert has a central post extending upwardly from an upper surface thereof. The method also includes selecting a tibial bearing surface trial component, securing a shim to the selected tibial bearing surface trial component to form a tibial bearing trial assembly, positioning the tibial bearing trial assembly over the central post of the base insert, and adjusting the patient's leg with the tibial bearing trial assembly positioned over the central post of the base insert. If a first tibial bearing surface trial component is selected, securing the shim includes securing the shim to the first tibial bearing surface trial component in a first orientation and adjusting the patient's leg includes rotating the tibial bearing trial assembly relative to the tibial base trial component. If a second tibial bearing surface trial component is selected, securing the shim includes securing the shim to the second tibial bearing surface trial component in a second orientation such that the tibial bearing trial assembly is substantially prevented from rotating relative to the tibial base trial component.

In some embodiments, the base insert may include a lug extending from the central post, and positioning the tibial bearing trial assembly over the central post of the base insert may include positioning the lug and the central post in an aperture defined in the shim. Additionally, in some embodiments, selecting the tibial bearing surface trial component may include selecting a mobile bearing surface trial component, and securing the shim may include securing the shim to the mobile bearing surface trial component in the first orientation.

In some embodiments, rotating the tibial bearing trial assembly relative to the tibial base trial component may include moving an arcuate inner wall of the shim relative to the lug. In some embodiments, inserting the base insert into the opening defined in the tibial base trial component may include inserting a spike of the base insert into the proximal end of the patient's tibia. In some embodiments, selecting the tibial bearing surface trial component may include selecting a fixed bearing surface trial component and securing the shim may include securing the shim to the fixed bearing surface trial component in the second orientation.

Additionally, in some embodiments, positioning the tibial bearing trial assembly may include positioning the lug between a pair of planar inner walls of the shim to prevent the tibial bearing trial assembly from rotating relative to the tibial base trial component.

In some embodiments, the method may further include locating an alignment etching on the tibial base trial component and marking the proximal end of the patient's tibia at the alignment etching after adjusting the patient's leg. Additionally, in some embodiments, the method may further include removing the tibial bearing trial assembly from the base insert, and detaching the shim from the tibial bearing surface trial component. The shim may have a first predetermined thickness. The method may also include selecting a second shim having a second predetermined thickness different from the first predetermined thickness, securing the second shim to the tibial bearing surface trial component to form a second tibial bearing trial assembly, positioning the second tibial bearing trial assembly over the central post of the base insert, and adjusting the patient's leg with the second tibial bearing trial assembly positioned over the central post of the base insert.

In some embodiments, detaching the shim from the tibial bearing surface trial component may include inserting a separator tool into a channel defined in an upper surface of the shim and actuating a lever to engage a bottom surface of the tibial bearing surface trial component to separate the shim from the tibial bearing surface trial component.

In some embodiments, adjusting the patient's leg may include placing the patient's knee in flexion, attaching an alignment handle to the tibial base trial component, inserting a first alignment rod into a first passageway defined in the alignment handle, and inserting a second alignment rod into a second passageway defined in the alignment handle. The second passageway may extend orthogonal to the first passageway.

In some embodiments, securing the shim to the tibial bearing surface trial component may include positioning a pair of pegs of the tibial bearing surface trial component into a pair of openings defined in the shim. In some embodiments, the method may further include selecting a prosthetic tibial bearing component corresponding to the selected tibial bearing surface trial component and the selected shim. Additionally, in some embodiments, the method may further include removing the tibial bearing trial assembly from the base insert and the tibial base trial component, removing the base insert from the opening defined in the tibial base trial component, and impacting a keel punch into the proximal end of the patient's tibia through the opening of the tibial base trial component. The keel punch may have a central post extending upwardly from an upper surface thereof. The method may also include positioning the tibial bearing trial assembly over the central post of the keel punch, and adjusting the patient's leg with the tibial bearing trial assembly positioned over the central post of the keel punch.

According to another aspect, the method of trialing prosthetic components of a knee prosthesis includes positioning an orthopaedic surgical instrument on a surgically-prepared proximal end of a patient's tibia, and selecting a tibial bearing surface trial component. The tibial bearing surface trial component is one of a mobile bearing surface trial component and a fixed bearing surface trial component. The method also includes positioning a shim and the selected tibial bearing surface trial component on the orthopaedic surgical instrument. A first surface of the shim is positioned in contact with the tibial bearing surface trial component if the tibial bearing surface trial component is the mobile bearing surface trial component. A second surface of the shim is positioned in contact with the tibial bearing surface trial component if the tibial bearing surface trial component is the fixed bearing surface trial component.

In some embodiments, the method may further include rotating the tibial bearing surface trial component and the shim relative to the orthopaedic surgical instrument if the mobile bearing surface trial component is selected. Additionally, in some embodiments, the shim may be configured to substantially prevent the tibial bearing surface trial component from rotating relative to the orthopaedic surgical instrument if the fixed bearing surface trial component is selected. In some embodiments, the method may further include selecting a prosthetic tibial bearing component corresponding to the selected tibial bearing surface trial component and the shim.

In some embodiments, the method may further include securing the shim to the selected tibial bearing surface trial component prior to positioning the shim and the tibial bearing surface trial component on the orthopaedic surgical instrument.

According to another aspect, a method of assembling a surgical instrument includes selecting a tibial bearing surface trial component, orienting a shim relative to the tibial bearing surface trial component, and securing the shim to the tibial bearing surface trial component. The shim is secured in a first orientation relative to the tibial bearing surface trial component if the tibial bearing surface trial component is a first tibial bearing surface trial component. The shim is secured in a second orientation that is opposite the first orientation if the tibial bearing surface trial component is a second tibial bearing surface trial component.

According to another aspect of the disclosure, the method includes positioning a polymer femoral trial component on a surgically-prepared distal end of a patient's femur, assembling a tibial bearing trial component, positioning the tibial bearing trial component on a tibial base trial component seated on a surgically-prepared proximal end of a patient's tibia, adjusting the patient's leg with the tibial bearing trial component engaging the polymer femoral trial component, removing the tibial bearing trial component from the tibial base trial component, inserting a keel punch into the surgically-prepared proximal end of the patient's tibia through an opening of the tibial base trial component, placing the tibial bearing trial component on the tibial base trial component and the keel punch, and readjusting the patient's leg with the tibial bearing trial component engaging the polymer femoral trial component after positioning the tibial bearing trial component on the tibial base trial component and the keel punch. In some embodiments, adjusting the patient's leg may include moving the patient's leg between extension and flexion such that a plurality of teeth of the polymer femoral trial component grip the surgically-prepared distal end of the patient's femur.

In some embodiments, the method may further include inserting a base insert into the opening of the tibial base trial component before positioning the tibial bearing trial component on the tibial base trial component. In some embodiments, assembling the tibial bearing trial component may include securing a shim to a first tibial bearing surface trial component in a first orientation, and positioning the tibial bearing trial component includes positioning a lug of the base insert in a first slot of the shim such that the tibial bearing trial component is prevented from substantially rotating relative to the tibial base trial component.

Additionally, in some embodiments, positioning the tibial bearing trial component on the tibial base trial component and the keel punch may include positioning a lug of the keel punch in the first slot of the shim such that the tibial bearing trial component is prevented from substantially rotating relative to the tibial base trial component. In some embodiments, assembling the tibial bearing trial component may include securing the shim to a second tibial bearing surface trial component in a second orientation, positioning the tibial bearing trial component may include positioning the lug of the base insert in a second slot of the shim such that the tibial bearing trial component is permitted to substantially rotate relative to the tibial base trial component, and adjusting the patient's leg may include rotating the tibial bearing trial component relative to the tibial base trial component. In some embodiments, inserting the base insert may include inserting a spike of the base insert into the patient's tibia.

In some embodiments, positioning the tibial bearing trial component on the tibial base trial component and the keel punch may include positioning a lug of the keel punch in the second slot of the shim such that the tibial bearing trial component is permitted to substantially rotate relative to the tibial base trial component, and readjusting the patient's leg may include rotating the tibial bearing trial component relative to the tibial base trial component. Additionally, in some embodiments, the method further may include placing a guide tower on the tibial base trial component, and securing the keel punch to a lower end of a handle by engaging a lever of the handle with the keel punch. Further, inserting the keel punch into the surgically-prepared proximal end of the patient's tibia may include inserting the keel punch and the lower end of the handle through an upper end of the guide tower.

In some embodiments, positioning the polymer femoral trial component may include securing an impactor head to the handle, attaching the polymer femoral trial component to the impactor head, and tapping a head end of the handle to attach the polymer femoral trial component to the surgically-prepared distal end of the patient's femur. Additionally, in some embodiments, the method may further include installing a tibial tray of the knee prosthesis in the surgically-prepared proximal end of the patient's tibia, positioning the tibial bearing trial component on the tibial tray, and readjusting the patient's leg after positioning the tibial bearing trial component on the tibial tray.

According to another aspect, a method of trialing prosthetic components of a knee prosthesis includes positioning a femoral trial component on a surgically-prepared distal end of a patient's femur, and selecting a first femoral prosthetic component if a sidewall of the femoral trial component is positioned beyond an outer edge of the surgically-prepared distal end of the patient's femur and the surgically-prepared distal end of the patient's femur is visible through a notch defined in the sidewall of the femoral trial component, and a second femoral prosthetic component if the sidewall of the femoral trial component is positioned within the outer edge of the surgically-prepared distal end of the patient's femur. The first femoral prosthetic component is more narrow than the second femoral prosthetic component. The method also includes positioning a tibial bearing trial component on a tibial base trial component seated on a surgically-prepared proximal end of a patient's tibia, and adjusting the patient's leg with the tibial bearing trial component engaging the femoral trial component.

In some embodiments, the femoral trial component may be formed from a polymeric material. In some embodiments, the method may further include inserting a keel punch into the surgically-prepared proximal end of the patient's tibia through an opening of the tibial base trial component, positioning the tibial bearing trial component on the tibial base trial component and the keel punch, and readjusting the patient's leg with the tibial bearing trial component engaging the femoral trial component after positioning the tibial bearing trial component on the tibial base trial component and the keel punch.

In some embodiments, the method may further include selecting a tibial bearing surface trial component from a plurality of tibial bearing surface trial components, orienting a shim relative to the tibial bearing surface trial component, and securing the shim to the tibial bearing surface trial component to assemble the tibial bearing trial component. The shim may be secured in a first orientation relative to the tibial bearing surface trial component if the tibial bearing surface trial component is a first tibial bearing surface trial component. The shim may be secured in a second orientation that is opposite the first orientation if the tibial bearing surface trial component is a second tibial bearing surface trial component.

In some embodiments, adjusting the patient's leg may include rotating the tibial bearing trial component relative to the tibial base trial component if the tibial bearing surface trial component is the first tibial bearing surface trial component.

According to another aspect, a method of trialing prosthetic components of a knee prosthesis includes positioning a polymer femoral trial component on a surgically-prepared distal end of a patient's femur, moving the patient's leg between extension and flexion such that a plurality of teeth of the polymer femoral trial component grip the surgically-prepared distal end of the patient's femur, and selecting a femoral prosthetic component of the knee prosthesis for implantation.

In some embodiments, the plurality of teeth of the polymer femoral trial component may extend from a posterior fixation surface defined by a plurality of ribs. The posterior fixation surface may extend generally in a superior/inferior direction. In some embodiments, selecting the femoral prosthetic component may include identifying a position of a sidewall of the polymer femoral trial component relative to an outer edge of the surgically-prepared distal end of the patient's femur. Selecting the femoral prosthetic component may also include selecting a first femoral prosthetic component if the sidewall is positioned beyond the outer edge of the surgically-prepared distal end of the patient's femur and the surgically-prepared distal end of the patient's femur is visible through a notch defined in the sidewall, and a second femoral prosthetic component if the sidewall of the polymer femoral trial component is positioned within the outer edge of the surgically-prepared distal end of the patient's femur. The first femoral prosthetic component may be more narrow than the second femoral prosthetic component.

In some embodiments, the method may further include drilling a pair of fixation holes in the surgically-prepared distal end of the patient's femur. In some embodiments, drilling the pair of fixation holes may include inserting a surgical drill into a guide hole defined in the polymer femoral trial component.

BRIEF DESCRIPTION OF THE DRAWINGS

The detailed description particularly refers to the following figures, in which.

DETAILED DESCRIPTION OF THE DRAWINGS

Figure 1:
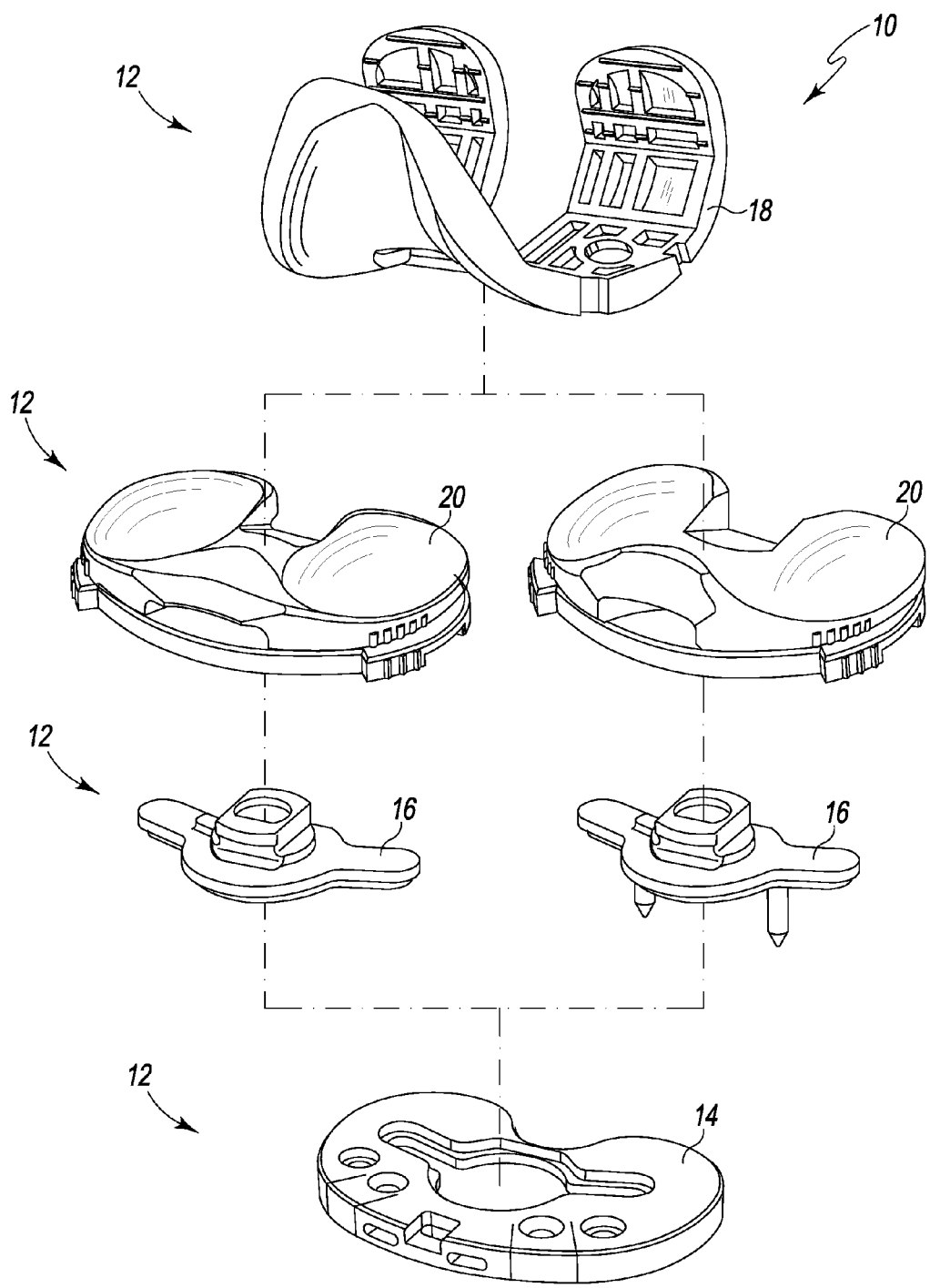
FIG. 1 is an exploded perspective view of an orthopaedic surgical instrument system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIGS. 1-16, an orthopaedic surgical instrument system 10 (hereinafter system 10) is shown. The system 10 is used during joint arthroplasty procedures, such as a total knee replacement procedure. It should be appreciated, however, that although the system 10 is described below in regard to the performance of a total knee replacement procedure, certain concepts associated with the system 10 may be utilized in replacement procedures of numerous other joints throughout the body.

As shown in FIG. 1, the system 10 has a number of trial components 12, including a tibial base trial 14, a number of base inserts 16, a femoral trial 18, and a number of tibial bearing trial assemblies 20. The system 10 also includes a tibial keel punch 22 (see FIG. 15) and a guide tower 24 (see FIG. 16). Additionally, the system 10 includes a number of surgical tools, such as, for example, an alignment handle 26 (see FIG. 17) and an impaction handle 28 (see FIG. 18), which are used to manipulate the trial components 12 and the other surgical instruments during the performance of an orthopaedic surgical procedure, as described in greater detail below.

The system 10 may be utilized to size and select the prosthetic components of a knee prosthesis (see FIGS. 19 and 20) that will replace the patient's natural joint. To do so, the femoral trial 18 is attached to a surgically-prepared distal end 600 of a patient's femur 602 (see FIG. 20), whereas the tibial base trial 14 is attached to a surgically-prepared proximal end 604 of a patient's tibia 606 (see FIG. 20). One of the tibial bearing trials 20, each of which is a multi-piece assembly, as discussed in greater detail below, is positioned on the tibial base trial 14 between the femoral trial 18 and the base trial 14. As described in greater detail below, the surgeon uses the system 10 in a trial reduction process to determine the type and configuration of each of the various types of prosthetic components that are to be implanted.

The system 10 may be also utilized to surgically prepare the proximal end 604 of a patient's tibia 606 for implantation of a tibial prosthetic component, such as a tibial tray, during the performance of an orthopaedic surgical procedure. The tibial base trial 14 and the guide tower 24 are positioned on the proximal end 604 of the patient's tibia 606, and the surgeon uses the trial 14 and the tower 24 to guide, for example, a surgical drill while reaming the proximal end 604 of the patient's tibia 606. Thereafter, the keel punch 22 is impacted into the proximal end 604 of the patient's tibia 606 before the guide tower 24 is removed. An additional trial reduction may be performed with the keel punch 22 before the surgeon installs the components of the knee prosthesis, as described in greater detail below.

Figure 2:
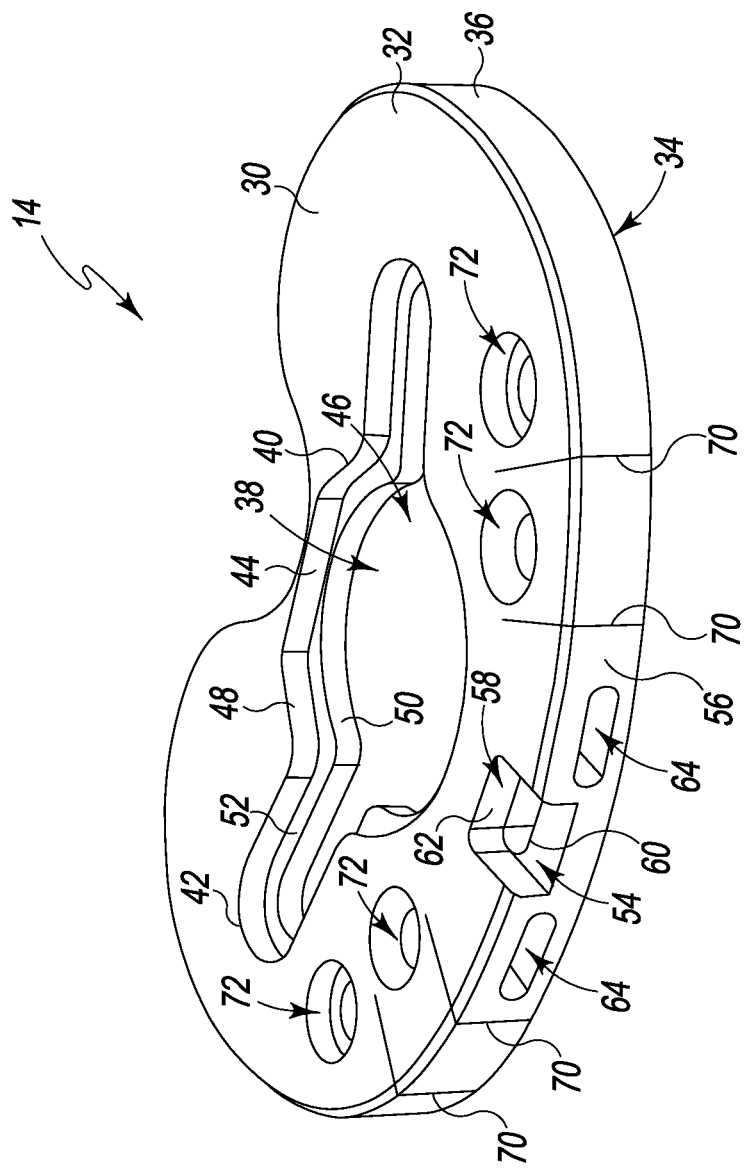
FIG. 2 is a perspective view of a tibial base trial component of the orthopaedic surgical instrument system of FIG. 1.

Referring now to FIG. 2, the base trial 14 includes a plate 30 having an upper surface 32, a lower surface 34, and an outer sidewall 36 extending between the surfaces 32, 34. The plate 30 has a plate opening 38 defined in the upper surface 32. The plate opening 38 has a central opening 40 and a pair of elongated openings 42 extending outwardly therefrom. An inner wall 44 extends downwardly from the opening 38 to define a passageway 46 through the plate 30. The inner wall 44 includes an upper wall 48 and a lower wall 50 offset or otherwise spaced inwardly from the upper wall 48. The upper wall 48 and lower wall 50 cooperate to define a shelf surface 52 therebetween. As will be discussed in greater detail below, the configuration of the passageway 46 permits the advancement of various surgical drills, punches, and other instruments into the proximal end 604 of the patient's tibia 606. It should be appreciated that the tibial base trial 14 may be formed in a number of different sizes to accommodate tibias of various sizes.

The plate 30 also includes a lever-receiving notch 54 that is defined in an anterior aspect 56 thereof. The notch 54 includes a channel 58 that is defined in the upper surface 32 and extends posteriorly from the outer sidewall 36. An oblong-shaped slot 60 is defined in the posterior end 62 of the channel 58. The slot 60 extends downwardly through the lower surface 34 of the plate 30. As shown in FIG. 2, a pair of oblong-shaped apertures 64 is defined in the sidewall 36, one on each side of the notch 54. As will be discussed in greater detail below, the notch 54 and the apertures 64 are configured to receive a lever 66 and a pair of pins 68, respectively, associated with the alignment handle 26 (see FIG. 17).

A plurality of alignment etchings 70 extend along the upper surface 32 and the outer sidewall 36 of the plate 30. The surgeon may use one or more of the alignment etchings 70 to mark the proper position of the base trial 14 on the proximal end 604 of the patient's tibia 606 and ensure that the base trial 14 is consistently positioned at the same location thereon. The plate 30 also includes a number of fastener holes 72 that are defined in the anterior aspect 56 thereof. The fastener holes 72 are configured to receive fasteners such as fixation pins, which may be utilized to secure the base trial 14 to the proximal end 604 of the patient's tibia 606.

Figure 3:
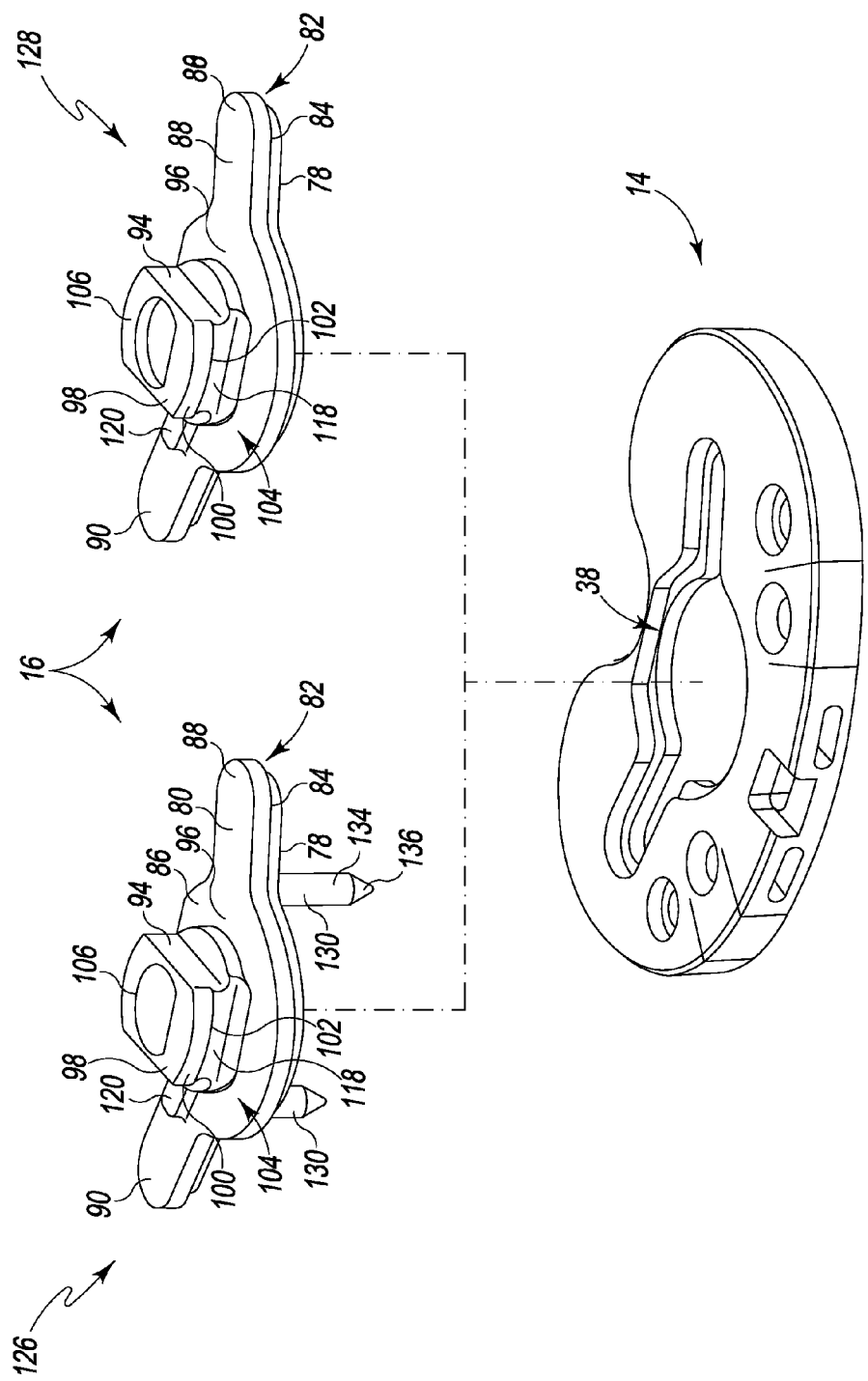
FIG. 3 is a perspective view of a base insert component of the orthopaedic surgical instrument system of FIG. 1.

Referring now to FIG. 3, the system 10 further includes a pair of evaluation bullets or base inserts 16. The base inserts 16 are configured to be positioned separately in the plate opening 38 of the base trial 14. Each base insert 16 has a lower body 78 and an upper body 80 that cooperate to define a rim 82 around the periphery thereof. The rim 82 has a bottom surface 84 configured to engage the shelf surface 52 of the base trial 14 when the base insert 16 is seated on the base trial 14. The body 80 includes a central platform 86 sized to be received in the central opening 40 of the base trial 14. The body 80 also includes a pair of prongs 88, 90 that extend outwardly from the central platform 86. The prongs 88, 90 are sized to be received in the elongated openings 42 of the base trial 14.

The body 80 of the base trial 14 includes a post 94 extending upwardly from an upper surface 96 thereof. The post 94 extends to a top end 98, and a lip 100 extends outwardly therefrom. The lip 100 has a bottom surface 102 that extends substantially parallel to the upper surface 96, and the surfaces 96, 102 cooperate to define a lever-receiving notch 104. The lever-receiving notch 104 is configured to receive a locking flange 498 associated with the impaction handle 28, as described in greater detail below.

Figure 4:
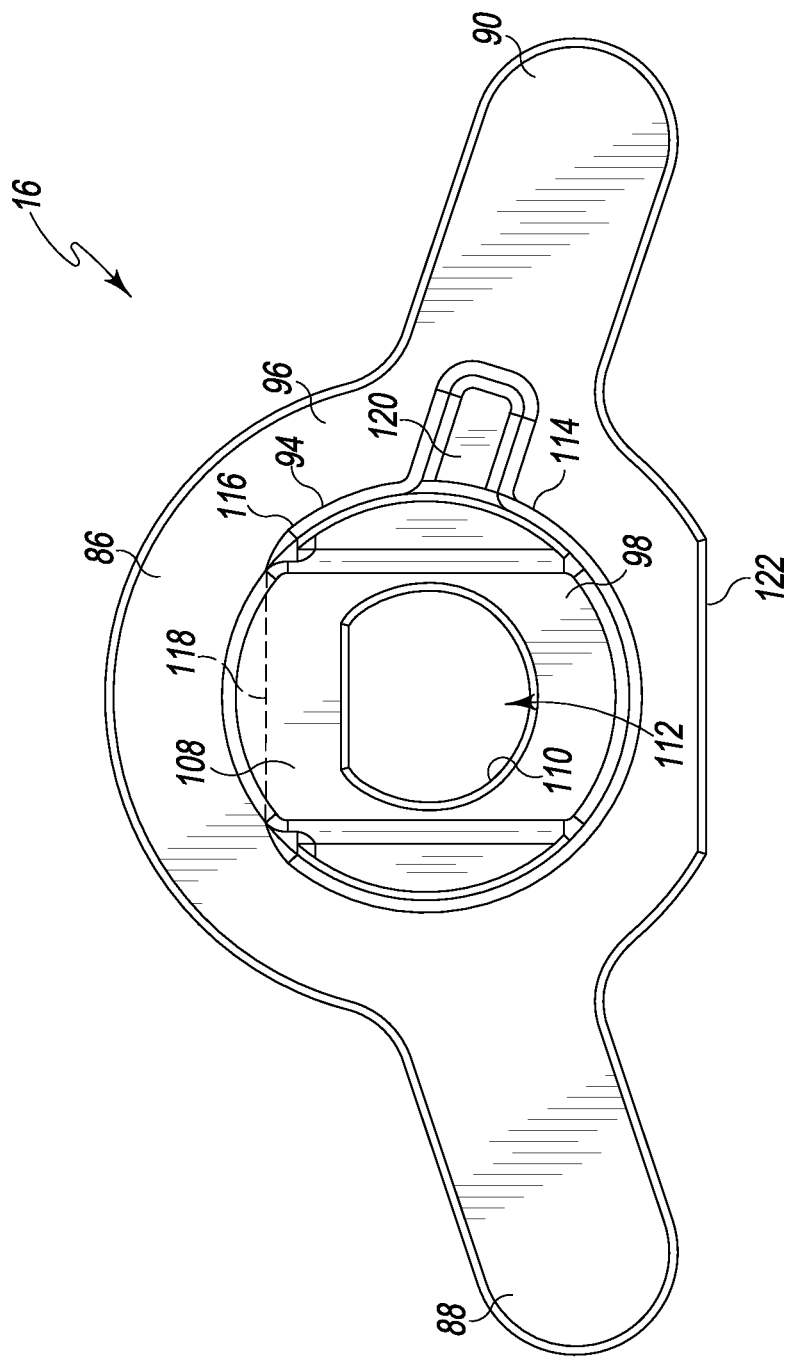
FIG. 4 is a top plan view of the base insert component of FIG. 3.

As shown in FIG. 4, the post 94 also has an opening 106 defined in an upper surface 108 thereof. An inner wall 110 extends downwardly from the opening 106 to define a central passageway 112 through the base insert 16. The opening 106 is configured to receive a guide pin 508 associated with the impaction handle 28 (see FIG. 18). The inner wall 110 has a keyed section 114 that permits the base insert 16 to be attached to the impaction handle 28 in only a single predetermined orientation.

The post 94 of each base insert 16 has a generally curved sidewall 116 and a flat sidewall 118 positioned under the lip 100. Each base insert 16 includes a block or lug 120 extending outwardly from the curved sidewall 116 of the post 94 toward the prong 90. As will be described in greater detail below, the lug 120 engages the tibial bearing trial 20 to prevent or permit the tibial bearing trial 20 from rotating relative to the tibial base trial 14. It should be appreciated that in other embodiments the lug 120 might extend from, for example, the other side of the post 94 toward the prong 88. It should also be appreciated that in other embodiments the base insert 16 may include additional lugs. In the illustrative embodiment, the lug 120 has a rectangular cross section, but it should be appreciated that in other embodiments the lug 120 may have, for example, a square or other geometrical cross section. As will be described in greater detail below, the post 94 and the lug 120 are positioned in the tibial bearing trial 20 when the tibial bearing trial 20 is positioned on the tibial base trial 14.

The central platform 86 of the body 80 also has a keyed section 122. The keyed section 122 and the orientation of the prongs 88, 90 relative to the platform 86 permit each base insert 16 to be inserted into the plate opening 38 of the base trial 14 in a single, predetermined orientation.

Returning to FIG. 3, the pair of base inserts 16 includes a spiked base insert 126 and a spikeless base insert 128. The spiked base insert 126 also includes a pair of mounting spikes 130 that extend downwardly from the prongs 88, 90, respectively. Each spike 130 includes an upper cylindrical section 134 and a pointed conical tip 136 configured to engage the proximal end 604 of the patient's tibia 606, thereby temporarily securing the base insert 126 to the proximal end 604 of the patient's tibia 606.

As discussed above, the system 10 also includes a femoral trial 18 that is configured to be secured to the distal end 600 of the patient's femur 602. One example of a femoral trial is shown and described in co-pending U.S. Patent App. Ser. No. 61/503,237, entitled "POLYMER FEMORAL TRIAL COMPONENT" by Thomas Wogoman, which is expressly incorporated herein by reference. The femoral trial 18 is configured to assist the surgeon in selecting a femoral prosthetic component, which will emulate the configuration of the patient's natural femoral condyles. As such, the femoral trial 18 includes a pair of condyle surfaces 140, 142, which may be shaped (i.e., curved) in a manner that approximates the condyles of the natural femur. The condyle surface 140 and the condyle surface 142 are spaced apart from one another, thereby defining an intercondylar notch 144 therebetween.

The condyle surfaces 140, 142 are formed in an articular side 146 of the femoral trial 18. A fixation side 148, which is the side of the femoral trial 18 that contacts the surgically-prepared distal end 600 of the patient's femur 602, is opposite the articular side 146. The fixation side 148 includes a plurality of ribs 138 that extend in a direction away from the articular side 146. The outer surfaces 150 of the ribs 138 define multiple surfaces that match and mate with planar surfaces surgically cut into the distal end 600 of the patient's femur 602, as described in greater detail below.

Figure 5:
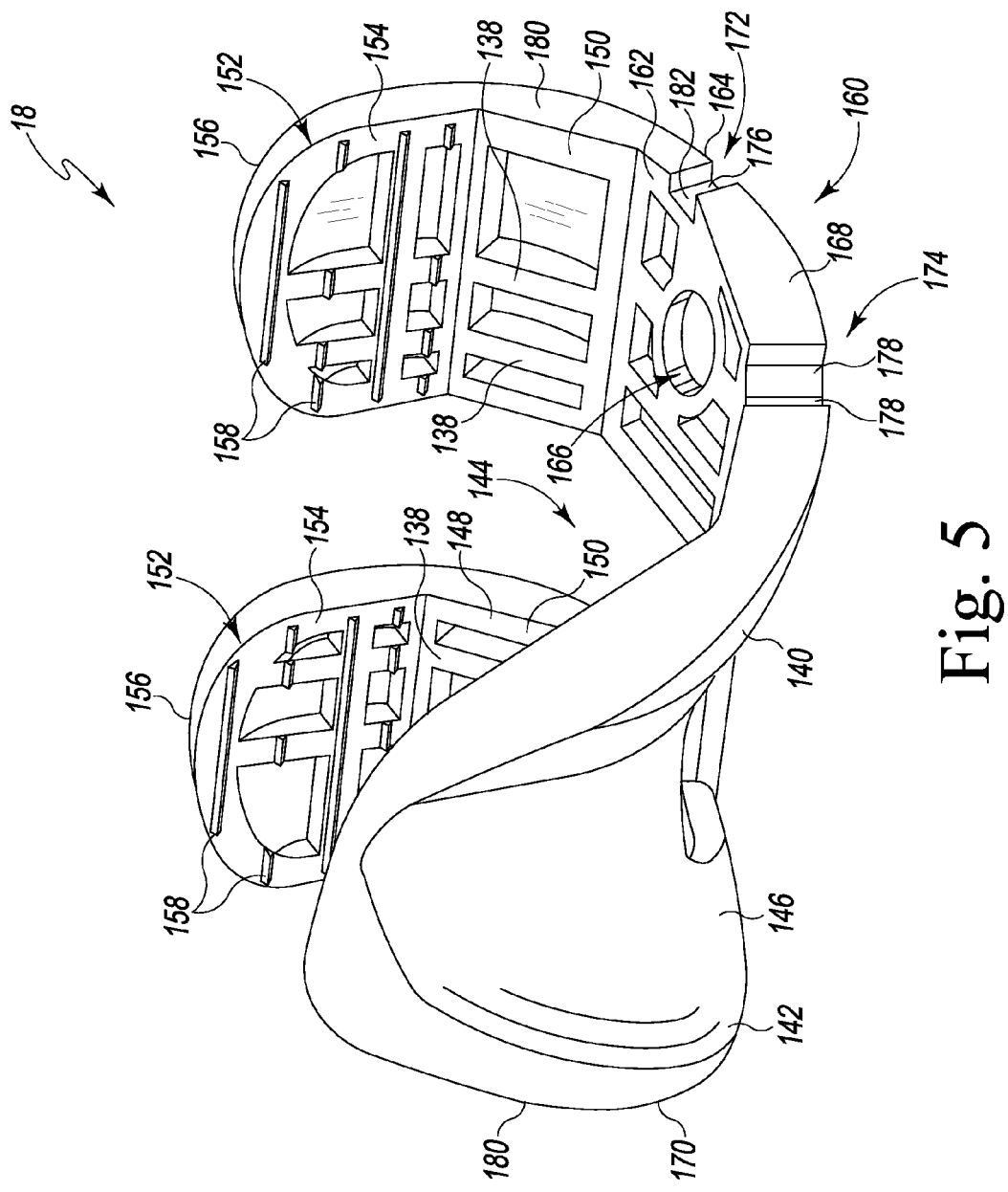
FIG. 5 is a perspective view of a femoral trial component of the orthopaedic surgical instrument system of FIG. 1.

The femoral trial 18 includes a pair of posterior femoral condyles 152 that form the posterior structure of the femoral trial 18. One of the femoral condyles 152 is medially positioned and the other laterally positioned when the femoral trial 18 is attached to the distal end 600 of the patient's femur 602 depending on which knee is being replaced. Each of the posterior femoral condyles 152 includes a planar posterior fixation surface 154 defined by the ribs 138 on the fixation side 148, with one of the posterior fixation surfaces 154 being the lateral fixation surface and the other being the medial fixation surface. Each posterior fixation surface 154 is positioned opposite a posterior condyle surface 156 on the articulation side 146 of the femoral trial 18. As shown in FIG. 5, the posterior fixation surfaces 154 and the posterior condyle surfaces 156 extend generally in the superior/inferior direction.

The femoral trial 18 of the system 10 also includes a plurality of teeth 158 that extend outwardly from each of the posterior fixation surfaces 154 in a direction away from the articular side 146. The teeth 158 are configured to engage the surgically-prepared distal end 600 of the patient's femur 602 when the femoral trial 18 is coupled thereto. The illustrative teeth 158 extend parallel to each other in the medial-lateral direction and have a triangular cross section. It should be appreciated that in other embodiments the teeth 158 may be angled relative to each other or arranged in various patterns on the posterior fixation surfaces 154. Additionally, one or more of the teeth 158 may extend inferiorly-superiorly along the posterior fixation surface 154 in addition to, or instead of, extending medially-laterally. It should also be appreciated that in other embodiments one or more teeth may be formed on any of the other surfaces of the fixation side 148 of the femoral trial 18.

As shown in FIG. 5, the femoral trial 18 has a distal condylar region 160 that includes a pair of distal fixation surfaces 162 (one being medially positioned, the other laterally positioned) defined by the outer surfaces 150 of the ribs 138. Each of the distal fixation surfaces 162 is opposite a distal condyle surface 164. The distal fixation surfaces 162 extend generally in the anterior-posterior direction. The distal condylar region 160 also includes a pair of apertures or through-holes 166, one of which is positioned laterally while the other is positioned medially. Each through-hole 166 is sized to receive a surgical drill, as described in greater detail below.

A pair of sidewalls 168, 170 extends between the articular side 146 and the fixation side 148, with one sidewall being medially positioned and the other laterally positioned depending on which knee is being replaced. Each of the sidewalls 168, 170 has a pair of notches 172, 174 defined therein. The notch 172 has a base surface 176 extending between the articular side 146 and the fixation side 148. Similarly, the notch 174 has a pair of base surfaces 178 extending between the articular side 146 and the fixation side 148. The sidewalls 168, 170 define an outer edge 180 of the femoral trial 18 corresponding to a standard femoral prosthetic component size. The base surfaces 176, 178 of the notches 172, 174 define another edge 182 of the femoral trial 18 corresponding to a standard, but more narrow, femoral prosthetic component size. In the illustrative embodiment, the notches 172, 174 extend inwardly approximately 1.75 millimeters from each of the sidewalls 168, 170, respectively, to the base surfaces 176, 178. As such, a single femoral trial 18 may be used to size multiple femoral prosthetic component sizes.

Figure 6:
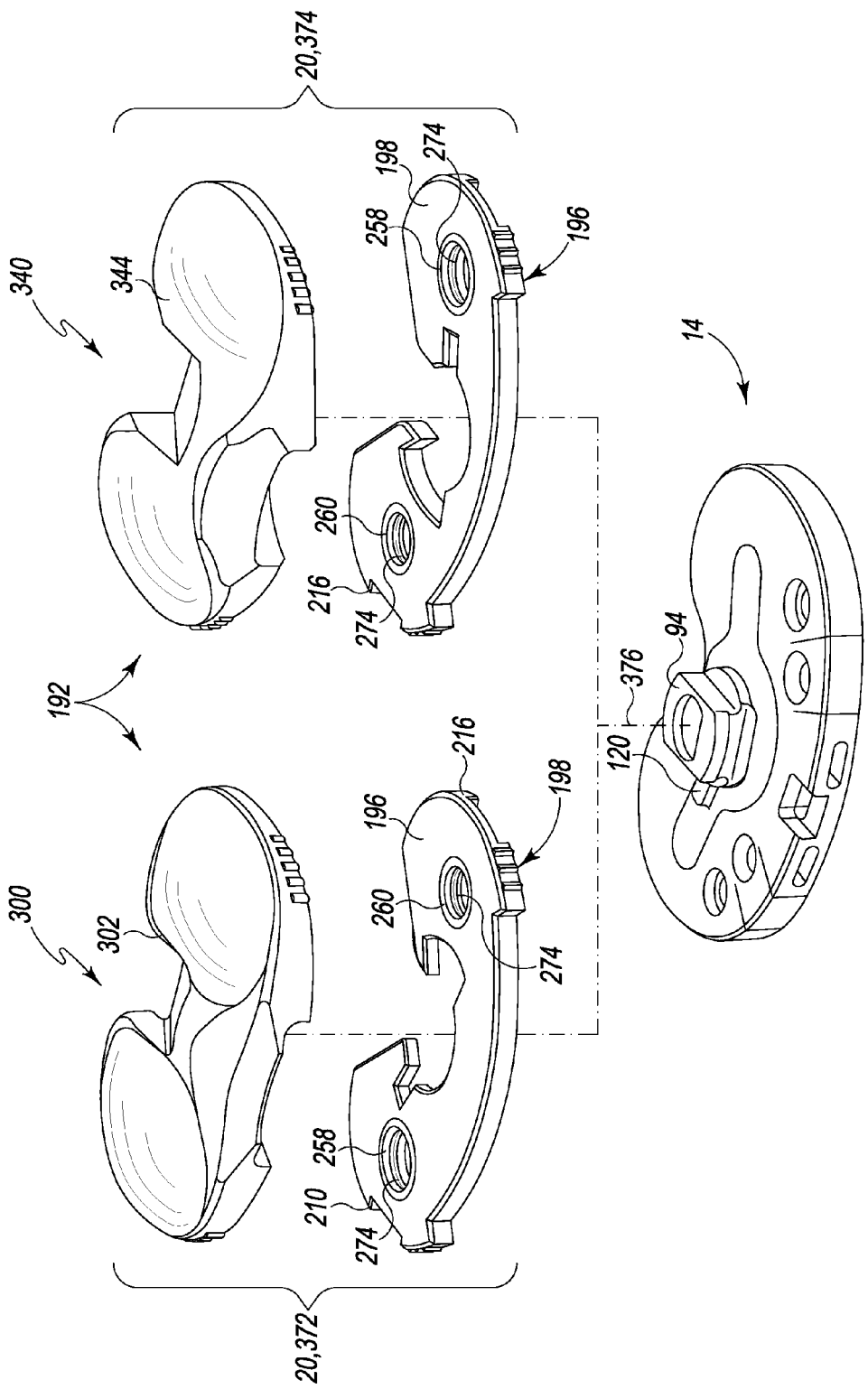
FIG. 6 is an exploded perspective view of the tibial base trial component, the base insert component, and a number of tibial bearing trial components of the orthopaedic surgical instrument system of FIG. 1.

Referring now to FIGS. 6-14, a number of tibial bearing trials 20 of the system 10 are shown. As discussed above, each tibial bearing trial 20 is a multi-piece assembly configured to assist the surgeon in selecting a size and configuration of a prosthetic tibial bearing component of the knee prosthesis. As shown in FIG. 6, a tibial bearing trial 20 may be assembled with one of a number of tibial bearing surface trials 192 and one of a plurality of trial shims 190. Each bearing surface trial 192 has a different size and/or configuration, and each shim 190 has a different thickness. Because each shim 190 is configured to be secured to each bearing surface trial 192, the surgeon is able to assemble a tibial bearing trial 20 of one size and configuration, evaluate the performance of that tibial bearing trial 20, and then modify the tibial bearing trial 20 as necessary to determine intraoperatively the type and configuration of the prosthetic tibial bearing component to be implanted.

Figure 9:
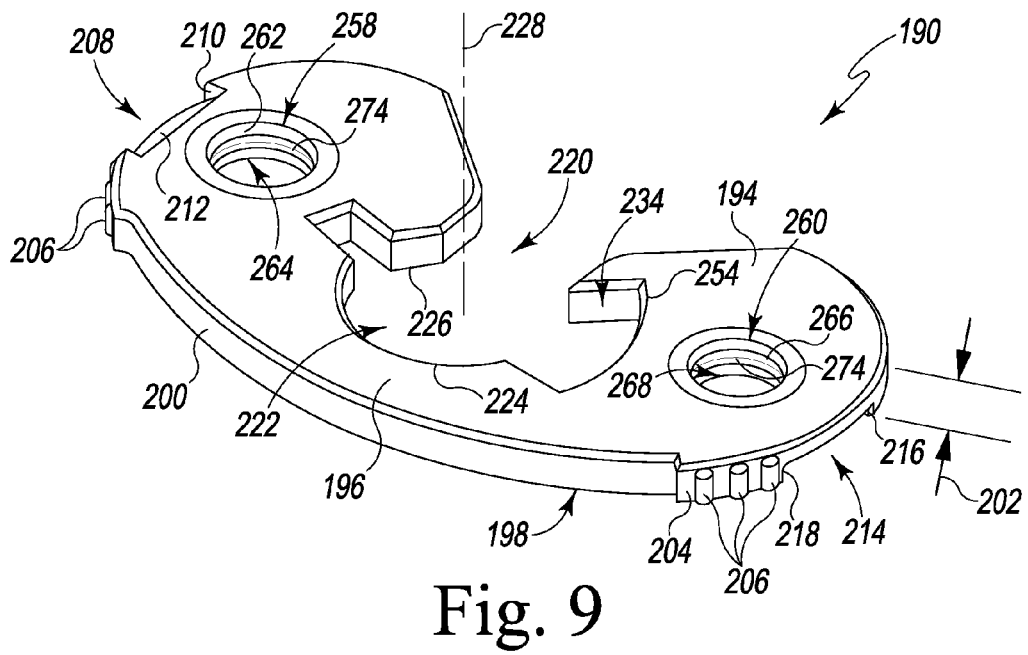
FIG. 9 is a perspective view of one embodiment of a trial shim of the tibial bearing trial component of FIG. 6.
Figure 10:
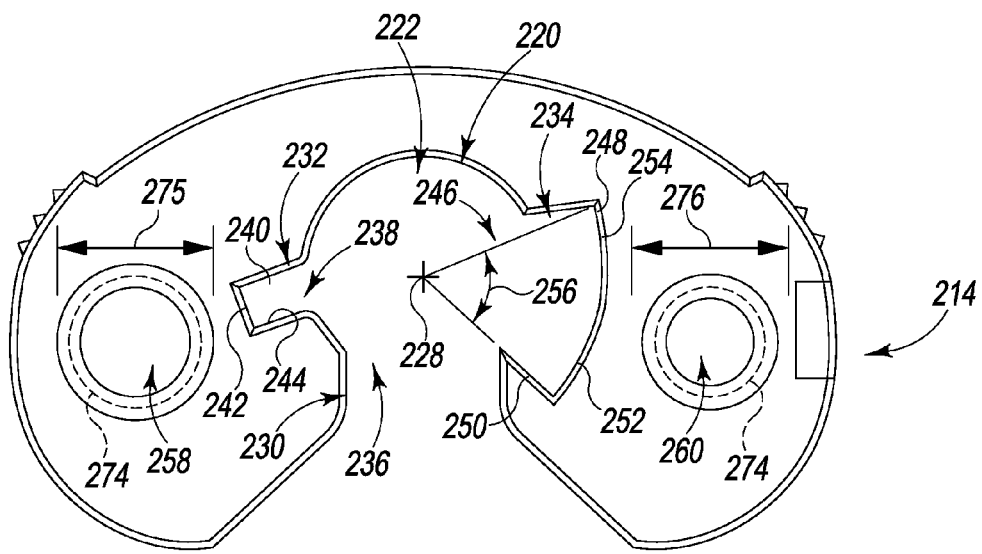
FIG. 10 is a top plan view of the trial shim of FIG. 9.

Referring now to FIGS. 9 and 10, one of the trial shims 190 is shown. The shim 190 includes a plate 194 having a planar surface 196 and a planar surface 198 opposite the planar surface 196. An outer sidewall 200 extends between the surfaces 196, 198 and defines a predetermined thickness 202 of the shim 190. As discussed above, the system 10 may include a plurality of trial shims, each of which may have a different thickness.

As shown in FIG. 9, a vertical surface 204 of the sidewall 200 is contoured with a number of ribs 206. The ribs 206 are sized and positioned to receive the fingertips of the surgeon to assist with the assembly of a trial 20. The plate 194 has a notch 208 defined in one side 210 thereof. The notch 208 includes a channel 212 that is defined in the planar surface 196 and extends inwardly from the sidewall 200. The plate 194 has another notch 214 defined in an opposite side 216 thereof. The notch 214 includes a channel 218 that is defined in the planar surface 198 and extends inwardly from the sidewall 200. As will be described in greater detail below, the notches 208, 214 are utilized to separate the shim 190 from the tibial bearing surface trial 192.

The shim 190 has an aperture 220 defined through the plate 194. As will be described in greater detail below, the aperture 220 is configured to receive the post 94 and the lug 120 of the base insert 16 when the shim 190 is positioned on the base trial 14. The aperture 220 includes a central passageway 222 extending between an opening 224 defined in the surface 196 of the plate 194 and an opening 226 defined in the surface 198. The central passageway 222 is sized to receive the post 94 of the base insert 16. The central passageway 222 also defines an axis 228 extending through the plate 194.

As shown in FIG. 10, the aperture 220 also includes a number of slots 230, 232, 234 extending outwardly from the passageway 222. The slot 230 extends from a posterior side 236 of the passageway 222 through the outer sidewall 200 of the plate 194. The slot 232 is rectangular and extends from another side 238 of the central passageway 222 toward the side 212 of the plate 194. The rectangular slot 232 is defined by substantially planar inner walls 240, 242, 244, which extend between the surfaces 196, 198 of the plate 194. As will be described in greater detail below, the lug 120 is received in the rectangular slot 232 when the shim 190 is attached in one orientation to one of the tibial bearing surface trials 192.

The slot 234 is arcuate in shape and extends outwardly from a side 246 of the central passageway 222 opposite the side 238. The arcuate slot 234 is defined by a pair of substantially planar inner walls 248, 250 and an arcuate inner wall 252 extending between the inner walls 248, 250. As will be described in greater detail below, the lug 120 is received in the arcuate slot 234 when the shim 190 is attached to another one of the tibial bearing surface trials 192 in another orientation.

The arcuate inner wall 252 has an edge 254 defined in the surface 196. The edge 254 defines an arc 256 about the axis 228 of the plate 194. In the illustrative embodiment, the arc 256 has a magnitude of approximately fifty degrees. It should be appreciated that in other embodiments the magnitude of the arc 256 may be greater or lesser than fifty degrees depending on nature of the knee prosthesis to be implanted.

The shim 190 also includes a pair of attachment openings 258, 260 that are defined in the surface 196 of the plate 194. The opening 258 is positioned between the side 238 of the passageway 222 and the side 216 of the plate 194. The opening 260 is positioned between the opposite side 246 of the passageway 222 and the side 212 of the plate 194. A cylindrical inner wall 262 extends downwardly from the opening 258 to define a through-hole 264. Similarly, a cylindrical inner wall 266 extends downwardly from the opening 260 to define a through-hole 268. The through-holes 264, 268 are configured to receive pegs 270, 272 of the tibial bearing surface trial 192, as will be described in greater detail below. As shown in FIG. 9, each inner wall 262, 266 has an indent or channel 274 defined therein sized to receive a corresponding spring 276 of the pegs 270, 272 to retain the pegs 270, 272 in the through-holes 264, 268.

The opening 258 (and through-hole 264) has a diameter 275, while the opening 260 (and through-hole 268) has a diameter 276 that is less than the diameter 275. In that way, the openings 258, 260 have the same shape but have a unique size. It should be appreciated that in other embodiments the openings 258, 260 may have rectangular, square, triangular, or other geometric shape. Additionally, while in the illustrative embodiment the openings 258, 260 have the same shape, it should be appreciated that in other embodiments each opening may have a unique shape. As will be described in greater detail below, the configuration of the openings 258, 260 ensures that the shim 190 may be attached to each tibial bearing surface trial 192 in a single, predetermined orientation.

Returning to FIG. 6, one of the bearing surface trials 192 is a fixed bearing surface trial 300. The term "fixed bearing surface trial" as used herein refers to a bearing surface trial that is fixed in position relative to the tibial base trial 14 when the bearing surface trial and shim are attached thereto (i.e., it is configured to not substantially rotate or move in the anterior-posterior direction or medial-lateral direction relative to the tibial base trial 14). The fixed bearing surface trial 300 may be embodied as a cruciate retaining trial, a posterior stabilized trial, a revision trial, or other surface trial configuration, per the surgeon's preference. For example, in embodiments where the fixed bearing surface trial 300 is embodied as a posterior stabilized trial, the fixed bearing surface trial 300 may include a spine extending upwardly from the upper bearing surface of the trial 300.

Figure 11:
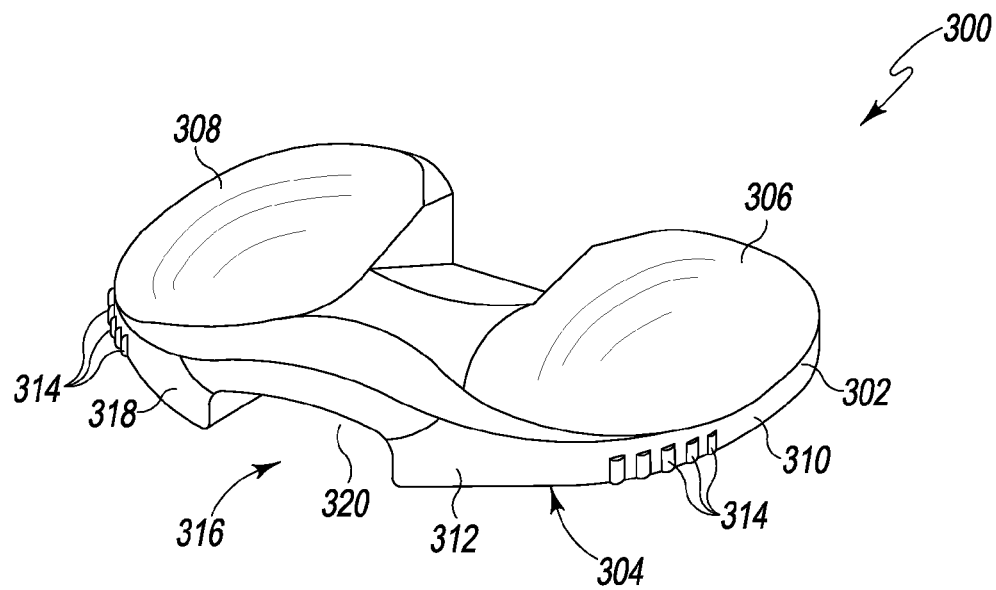
FIG. 11 is a perspective view of one embodiment of a fixed bearing surface trial component of one of the tibial bearing trial components of FIG. 6.
Figure 12:
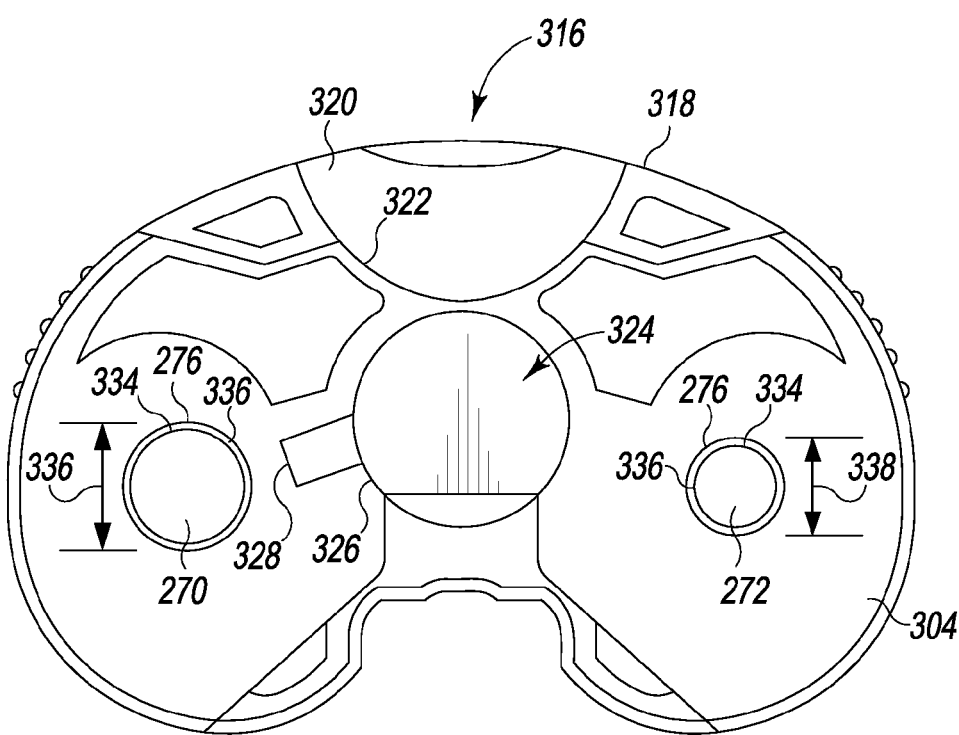
FIG. 12 is a bottom plan view of the fixed bearing surface trial component of FIG. 11.

Referring now to FIGS. 11 and 12, the fixed bearing surface trial 300 has a platform 302 including a lower surface 304 that contacts the surface 196 of the shim 190 when the shim 190 is secured thereto. The platform 302 of the fixed bearing surface trial 300 also includes a pair of articular surfaces 306, 308 that are positioned opposite the lower surface 304. The articular surfaces 306, 308 are configured to rotate with the condyle surfaces 140, 142, respectively, of the femoral trial 18. The platform 302 is defined by an outer sidewall 310 extending between the lower surface 304 and the articular surfaces 306, 308. A surface 312 of the sidewall 310 is contoured with a number of ribs 314, which are sized to receive the fingertips of the surgeon and assist with the assembly of a tibial bearing surface trial 192.

The platform 302 also has a notch 316 defined in an anterior aspect 318 thereof. As will be described in greater detail below, the notch 316 is used to separate the tibial bearing trial 20 from the tibial base trial 14 when the tibial bearing trial 20 is positioned thereon. The notch 316 includes a channel 320 that is defined in the lower surface 304. As shown in FIG. 12, the channel 320 is dome-shaped and is defined by a curved inner wall 322 extending inwardly from the sidewall 310. It should be appreciated that in other embodiments the channel 320 may be defined by substantially straight inner walls such that the channel is, for example, rectangular in shape.

As shown in FIG. 12, the platform 302 of the fixed bearing surface trial 300 has an aperture 324 defined in the lower surface 304 thereof. The aperture 324 includes a central opening 326 and a slot 328 extending outwardly from the central opening 326. When the shim 190 is secured to the lower surface 304 of the platform 302, the central opening 326 is substantially aligned with the central passageway 222 of the shim 190 and the slot 328 is substantially aligned with the rectangular slot 232 of the shim 190. Thus, the central opening 326 is circular in shape and is sized to receive the top end 98 of the post 94 of the base insert 16. Similarly, the slot 328 of the aperture 324 is rectangular and is sized to receive the lug 120 of the base insert 16.

The fixed bearing surface trial 300 also includes a pair of pegs 270, 272 that extend downwardly from the lower surface 304. The pegs 270, 272 are positioned on each side of the aperture 324. Each of the pegs 270, 272 has a cylindrical body 334, and each body 334 extends the same length from the lower surface 304. The peg 270 has a diameter 337 that corresponds to the diameter 275 of the opening 258 of the shim 190, and the peg 272 has a diameter 338 that corresponds to the diameter 276 of the opening 260 of the shim 190. In that way, the shim 190 may be attached to the lower surface 304 of the fixed bearing surface trial 300 and positioned on the tibial base trial 14 in only a single orientation. It should be appreciated that in other embodiments the pegs 270, 272 may have a rectangular, square, triangular, or other geometrically-shaped cross section. Additionally, while in the illustrative embodiment the pegs 270, 272 have the same shape, it should be appreciated that in other embodiments each peg may have a unique shape.

As discussed above, each of the pegs 270, 272 includes a spring 276 sized to be received in a corresponding channel 274 defined in the shim 190. Each spring 276 is received in a slot 336 defined in the body 334 of each of the pegs 270, 272. In the illustrative embodiment, each spring 276 is a ring-shaped coil configured to snap into each channel 274 of the shim 190 to secure to the shim 190 to the bearing surface trial 192. One example of a spring 276 is the Bal Seal Engineering Rotary Seal, which is commercially available from Bal Seal Engineering, Inc. of Foothill Ranch, Calif., U.S.A. It should be appreciated that in other embodiments the spring may take the form of another biasing or friction element, such as, for example, an o-ring, a retaining ring, or other element capable of securing the shim 190 to the surface trial 192. Additionally, in other embodiments, the bearing surface trial 192 may be secured to the shim 190 via friction between the pegs 270, 272 and the inner walls 262, 266 of the shim 190.

Returning to FIG. 6, the other bearing surface trial 192 is embodied as a mobile bearing surface trial 340. The term "mobile bearing surface trial" as used herein refers to a bearing surface trial that is permitted to rotate relative to the tibial base trial 14 when the bearing surface trial and the shim are attached thereto (i.e., it is configured to substantially rotate or move in the anterior-posterior direction or the medial-lateral direction relative to the tibial base trial 14). The mobile bearing surface trial 340 may be embodied as a cruciate retaining trial, a posterior stabilized trial, a revision trial, or other surface trial configuration, per the surgeon's preference. For example, in embodiments where the mobile bearing surface trial 340 is embodied as a posterior stabilized trial, the mobile bearing surface trial 340 may include a spine extending upwardly from the upper bearing surface thereof.

Figure 13:
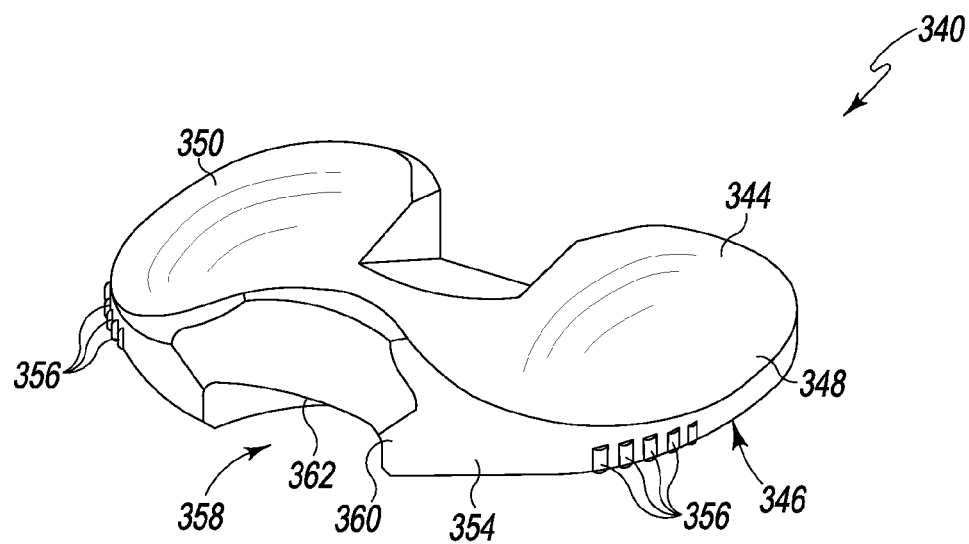
FIG. 13 is a perspective view of one embodiment of a mobile bearing surface trial component of one of the tibial bearing surface trial components of FIG. 6.
Figure 14:
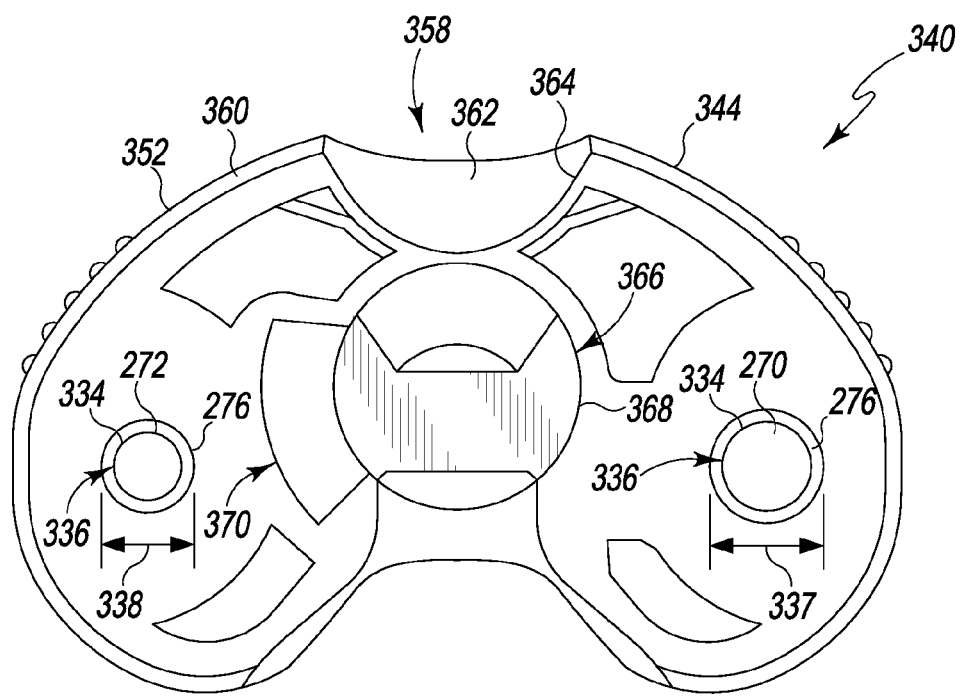
FIG. 14 is a bottom plan view of the mobile bearing surface trial component of FIG. 13.

Referring now to FIGS. 13 and 14, the mobile bearing surface trial 340 has a platform 344 including a lower surface 346 that contacts the surface 198 of the shim 190 when the shim 190 is secured thereto. The platform 344 of the mobile bearing surface trial 340 also includes a pair of articular surfaces 348, 350 that are positioned opposite the lower surface 346. The articular surfaces 348, 350 are configured to rotate with the condyle surfaces 140, 142, respectively, of the femoral trial 18. The platform 344 is defined by an outer sidewall 352 extending between the lower surface 346 and the articular surfaces 348, 350. A surface 354 of the sidewall 352 is contoured with a number of ribs 356, which are sized to receive the fingertips of the surgeon and assist with the assembly of the tibial bearing surface trial 192.

The platform 344 also has a notch 358 defined in an anterior aspect 360 thereof. As will be described in greater detail below, the notch 358, like the notch 316, is used to separate the tibial bearing trial 20 from the tibial base trial 14 when the tibial bearing trial is positioned thereon. The notch 358 includes a channel 362 that is defined in the lower surface 346. As shown in FIG. 12, the channel 362 is dome-shaped and is defined by a curved inner wall 364 extending inwardly from the sidewall 352. It should be appreciated that in other embodiments the channel 362 may be defined by substantially straight inner walls such that the channel is, for example, rectangular in shape.

As shown in FIG. 14, the platform 344 of the mobile bearing surface trial 340 has an aperture 366 defined in the lower surface 346 thereof. The aperture 366 includes a central opening 368 and an arcuate slot 370 extending outwardly from the central opening 368. When the shim 190 is secured to the lower surface 346 of the platform 344, the central opening 368 is substantially aligned with the central passageway 222 of the shim 190 and the slot 328 is substantially aligned with the arcuate slot 234 of the shim 190. Thus, the central opening 368 is circular in shape and is sized to receive the top end 98 of the post 94 of the base insert 16. Similarly, the slot 370 of the aperture 366 is sized to receive the lug 120 of the base insert 16.

The mobile bearing surface trial 340 also includes a pair of pegs 270, 272 that extend downwardly from the lower surface 346. The pegs 270, 272 are positioned on each side of the aperture 366. Each of the pegs 270, 272 has a cylindrical body 334, and each body 334 extends the same length from the lower surface 346. The peg 270 has a diameter 337 that corresponds to the diameter 275 of the opening 258 of the shim 190, and the peg 272 has a diameter 338 that corresponds to the diameter 276 of the opening 260 of the shim 190. As discussed above, each of the pegs 270, 272 also includes a spring 276 sized to be received in a corresponding channel 274 defined in the shim 190. Each spring 276 is received in a slot 336 defined in the body 334 of each of the pegs 270, 272. In that way, the shim 190 may be attached to the lower surface 346 of the mobile bearing surface trial 340 and positioned on the tibial base trial 14 in only a single orientation that is the reverse of the orientation of the shim 190 when the shim 190 is attached to the fixed bearing surface trial 300.

Returning to FIG. 6, the surgeon may assemble one of the shims 190 with one of the bearing surface trials 192 to form a tibial bearing trial 20. For example, the surgeon may select one of the fixed bearing surface trials 300 and secure the shim 190 thereto to form a fixed bearing trial 372. To do so, the surgeon aligns the pegs 270, 272 of the bearing surface trial 192 with the openings 258, 260 and then advances the pegs into the correct opening such that the springs 276 are received in the channels 274 defined in the shim 190. The surgeon may choose to position the fixed bearing trial 372 on the base trial 14 by aligning the apertures 220, 324 of the fixed bearing trial 372 with the post 94 and the lug 120 of the base insert 16. The fixed bearing trial 372 is then placed over the post 94 and the lug 120 and the surface 198 of the shim 190 is advanced into contact with the upper surface 32 of the base trial 14.

Figure 7:
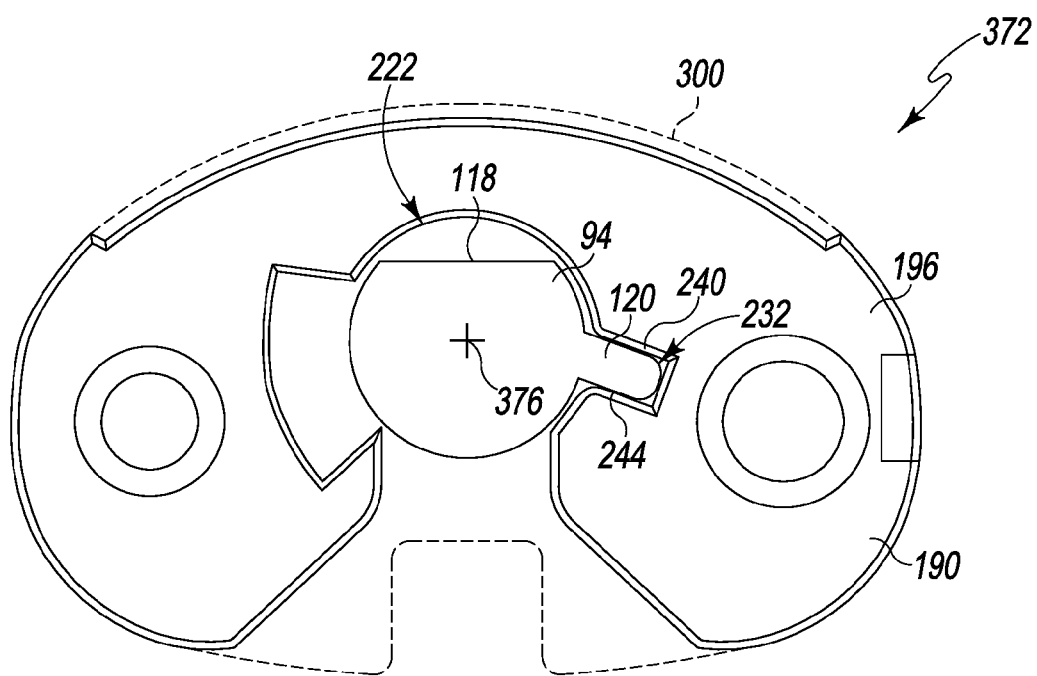
FIG. 7 is a top plan view of the tibial base trial component, the base insert component, and a fixed bearing trial component.

When the fixed bearing trial 372 is properly seated as shown in FIG. 7, the lug 120 is received in the slot 232 of the shim 190 and the post 94 is received in the central passageway 222. The inner walls 240, 244 of the shim 190 cooperate with the lug 120 to prevent the fixed bearing trial 372 from rotating relative to the base trial 14. It should be appreciated that in other embodiments the shim 190 may be positioned on the tibial base trial 14 prior to attaching the fixed bearing surface trial 300 thereto.

Alternatively, the surgeon may assemble one of the shims 190 with one of the mobile bearing surface trials 340 to form a mobile bearing trial 374. The surgeon positions the mobile bearing trial 374 on the base trial 14 by aligning the apertures 220, 324 of the mobile bearing trial 374 with the post 94 and the lug 120 of the base insert 16. The surgeon then places the mobile bearing trial 374 over the post 94 and the lug 120 and advances the surface 196 of the shim 190 into contact with the upper surface 32 of the base trial 14.

Figure 8:
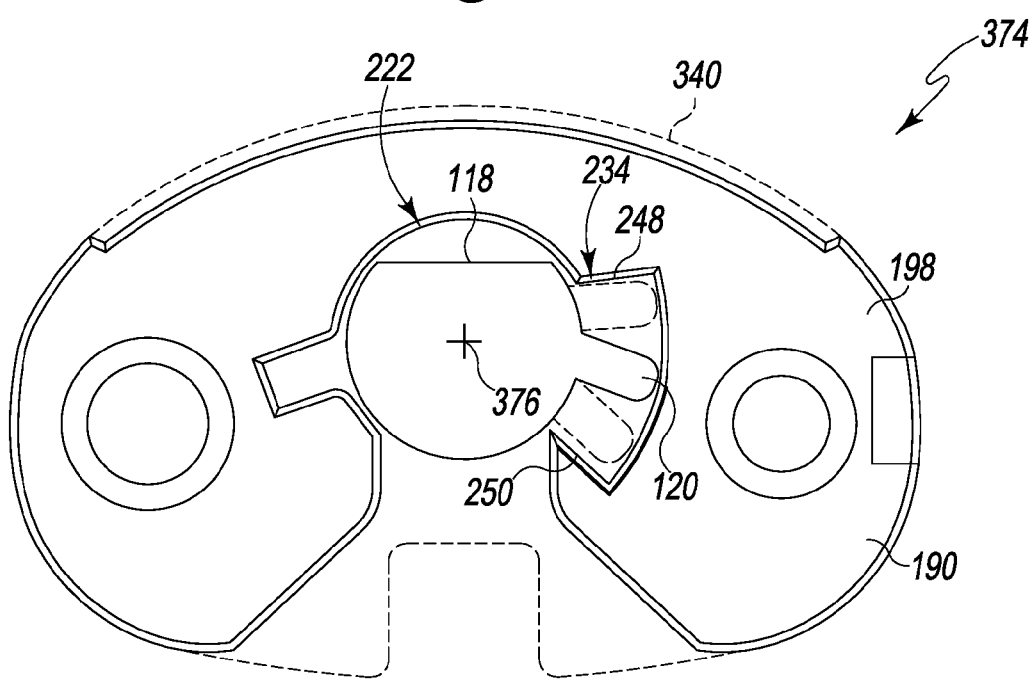
FIG. 8 is a top plan view of the tibial base trial component, the base insert component, and a mobile bearing trial component.

When the mobile bearing trial 374 is properly seated as shown in FIG. 8, the lug 120 is received in the slot 234 of the shim 190 and the post 94 is received in the central passageway 222. It should be appreciated that in other embodiments the shim 190 may be positioned on the tibial base trial 14 prior to attaching the mobile bearing surface trial 340 thereto. As shown in FIG. 8, the post 94 defines a longitudinal axis 376 extending in a superior/inferior direction along the passageway 112 of the base insert 16. The arcuate slot 234 of the shim 190 permits the mobile bearing trial 374 to rotate relative to the base trial 14 about the axis 376. When the mobile bearing trial 374 is rotated in one direction, the lug 120 may be advanced along the arcuate inner wall 252 into contact with the inner wall 248 of the shim 190; when the mobile bearing trial 374 is rotated in the opposite direction, the lug 120 may be advanced along the arcuate inner wall 252 into contact with the opposite inner wall 250. In that way, rotation of the mobile bearing trial 374 about the axis 376 is limited by the arc 256 defined by the arcuate inner wall 252 to approximately fifty degrees.

Figure 15:
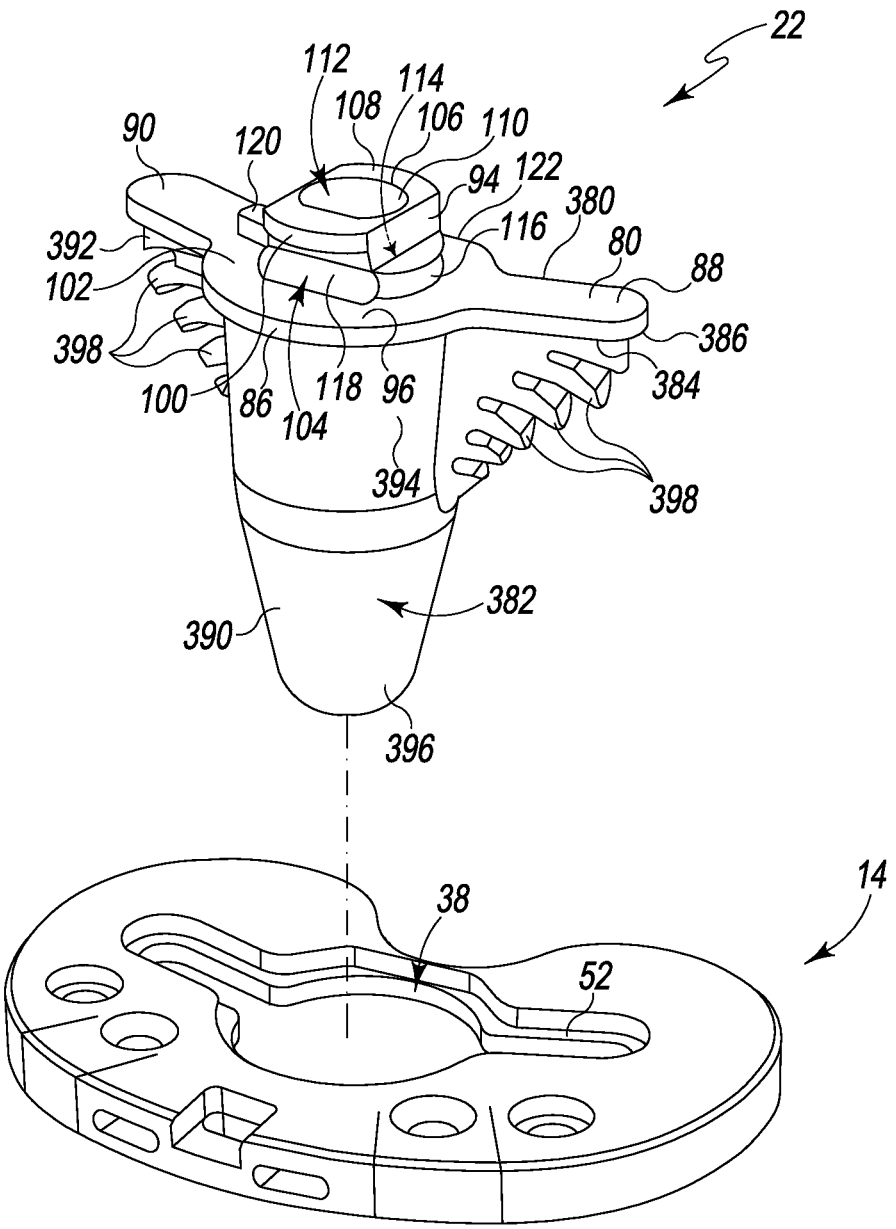
FIG. 15 is an exploded perspective view of a keel punch used with the tibial base trial component of the orthopaedic surgical instrument system of FIG. 1.

Referring now FIG. 15, the system 10 further includes a keel punch 22. The keel punch 22 is configured to be inserted through the plate opening 38 of the base trial 14 into the proximal end 604 of the patient's tibia 606 to prepare the patient's tibia 606 for a prosthetic component. The keel punch 22 has an upper frame 380 and a main body 382 extending downwardly therefrom. The upper frame 380 and the main body 382 cooperate to define a rim 384 around the periphery thereof. The rim 384 has a bottom surface 386 configured to engage the shelf surface 52 of the base trial 14 when the keel punch 22 is seated on the base trial 14 and in the proximal end 604 of the patient's tibia 606.

As shown in FIG. 15, the upper frame 380 of the keel punch 22 has a configuration similar to the upper body 80 of the base trial 14. The upper frame 380 includes a central platform 86 sized to be received in the central opening 40 of the base trial 14. The upper frame 380 also includes a pair of prongs 88, 90 that extend outwardly from the central platform 86, which are sized to be received in the elongated openings 42 of the base trial 14.

The upper frame 380 of the keel punch 22 includes a post 94 extending upwardly from an upper surface 96 thereof. The post 94 extends to a top end 98, and a lip 100 extends outwardly therefrom. The lip 100 has a bottom surface 102 that extends parallel to the upper surface 96, and the surfaces 96, 102 cooperate to define a lever-receiving notch 104. The lever-receiving notch 104 is configured to receive the locking flange 498 associated with the impaction handle 28, as described in greater detail below.

The post 94 also has an opening 106 defined in an upper surface 108 thereof. An inner wall 110 extends downwardly from the opening 106 to define a central passageway 112 through the keel punch 22. The inner wall 110 has a keyed section 114 (see FIG. 15) that permits the keel punch 22 to be attached to the impaction handle 28 in only a single predetermined orientation.

As shown in FIG. 15, the post 94 of the keel punch 22 has a generally curved sidewall 116 and a flat sidewall 118 positioned under the lip 100. The keel punch 22 also includes a block or lug 120 extending outwardly from the curved sidewall 116 of the post 94 toward the prong 90. Like the base insert 16, the post 94 and the lug 120 of the keel punch 22 are positioned in the tibial bearing trial 20 when the tibial bearing trial 20 is positioned on the tibial base trial 14 and the keel punch 22 is positioned in the tibial base trial 14.

The central platform 86 of the keel punch 22 also has a keyed section 122 (see FIG. 15). The keyed section 122 and the orientation of the prongs 88, 90 relative to the platform 86 permit the keel punch 22 to be inserted into the plate opening 38 of the base trial 14 in a single, predetermined orientation.

The main body 382 of the keel punch 22 includes a central bullet 390 and a pair of lower arms 392 that are positioned below the prongs 88, 90 and extend outwardly from the central bullet 390. The central bullet 390 has circular cross section that varies in diameter along its length (i.e., the diameter of the bullet 390 tapers in the superior-inferior direction). In that way, the cross sectional diameter of the bullet 390 at an upper end 394 is greater than the cross sectional diameter of the bullet 390 at a lower end 396. A number of downwardly extending teeth 398 are defined in each of the lower arms 392. The teeth 398 are configured to engage the patient's tibia 606 to define an opening 672 in the proximal end 604 of the patient's tibia 606 sized to receive the tibial implant (see FIG. 37).

Figure 16:
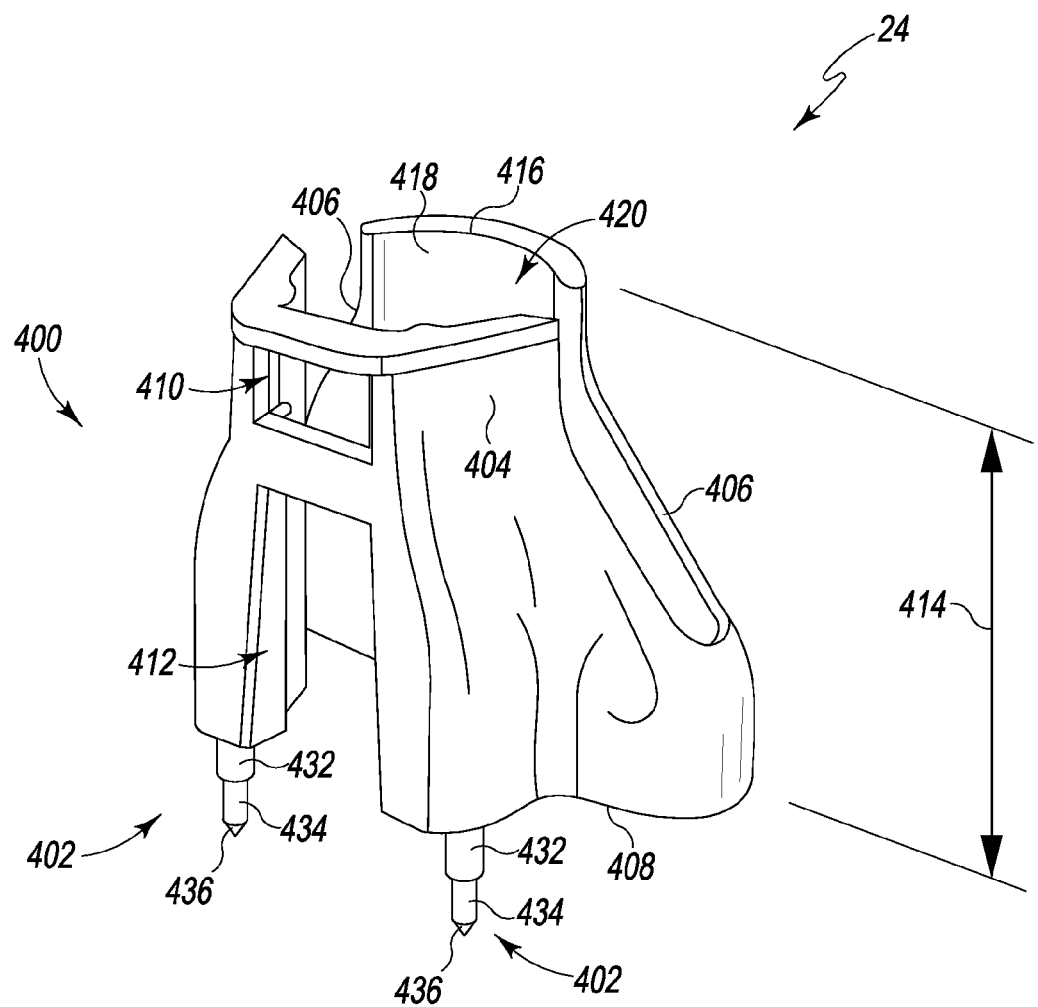
FIG. 16 is a perspective view of a guide tower of the orthopaedic surgical instrument system of FIG. 1.

As described above, the system 10 also includes the guide tower 24, which is configured to be positioned on the base trial 14 during use. One example of a guide tower is shown and described in co-pending U.S. Patent App. Ser. No. 61/503,324, entitled "KEEL PUNCH AND IMPACTION HANDLE ASSEMBLY AND ASSOCIATED SURGICAL INSTRUMENTS FOR USE IN SURGICALLY PREPARING A TIBIA FOR IMPLANTATION OF A PROSTHETIC COMPONENT" by David Waite et al., which is incorporated herein by reference. As shown in FIG. 16, the guide tower 24 includes a tower base 400 and a pair of fixation pins 402 extending downwardly from the tower base 400. The tower base 400 includes a main body 404 and a pair of arms 406 extending outwardly from the main body 404. A bottom surface 408 of the tower base 400 is configured to be positioned on the base trial 14, and the fixation pins 402 extend downwardly therefrom. The main body 404 also has an upper aperture 410 and a lower aperture 412 defined therein, and the main body 404 has a height 414, which may correspond to a predetermined drilling depth in the patient's tibia 606, as described in greater detail below.

As shown in FIG. 16, the tower base 400 has an upper guide opening 416 defined therein. The tower base 400 has an inner wall 418 that extends downwardly from the upper guide opening 416 to a lower guide opening (not shown) defined in the bottom surface 408. The inner wall 418 defines a vertically-extending passageway 420 through the main body 404 and the arms 406. The cross sectional shape of the passageway 420 of the tower base 400 substantially matches the cross sectional shape of the passageway 46 of the base trial 14. When the guide tower 24 is properly positioned on the base trial 14, the passageways 46, 420 are substantially aligned. In that way, the configuration of the passageway 420, like the configuration of the passageway 46, permits the advancement of various surgical drills, punches, and other instruments into the proximal end 604 of the patient's tibia 606, as will be described in greater detail below. The apertures 410, 412 extend inwardly and are in communication with the passageway 420.

The fixation pins 402 extending from the bottom surface 408 are sized to be received in a corresponding pair of the fastener holes 72 defined in the base trial 14. Each fixation pin 402 includes an upper section 432 and a lower section 434 extending downwardly from the upper section 432. Each fixation pin 402 further includes a pointed conical tip 436 configured to engage the proximal end 604 of the patient's tibia 606. It should be appreciated that in other embodiments the guide tower 24 may include additional or fewer fixation pins 402.

In the illustrative embodiment, the base trial 14, the base insert 16, the keel punch 22, and the guide tower 24 are formed from an implant-grade metallic material such as steel, titanium, or cobalt chromium. The femoral trial 18, the shims 190, and the tibial bearing surface trials 192 are formed from a polymeric material such as polyethylene or ultra-high molecular weight polypropylene (UHMWPE).

Figure 17:
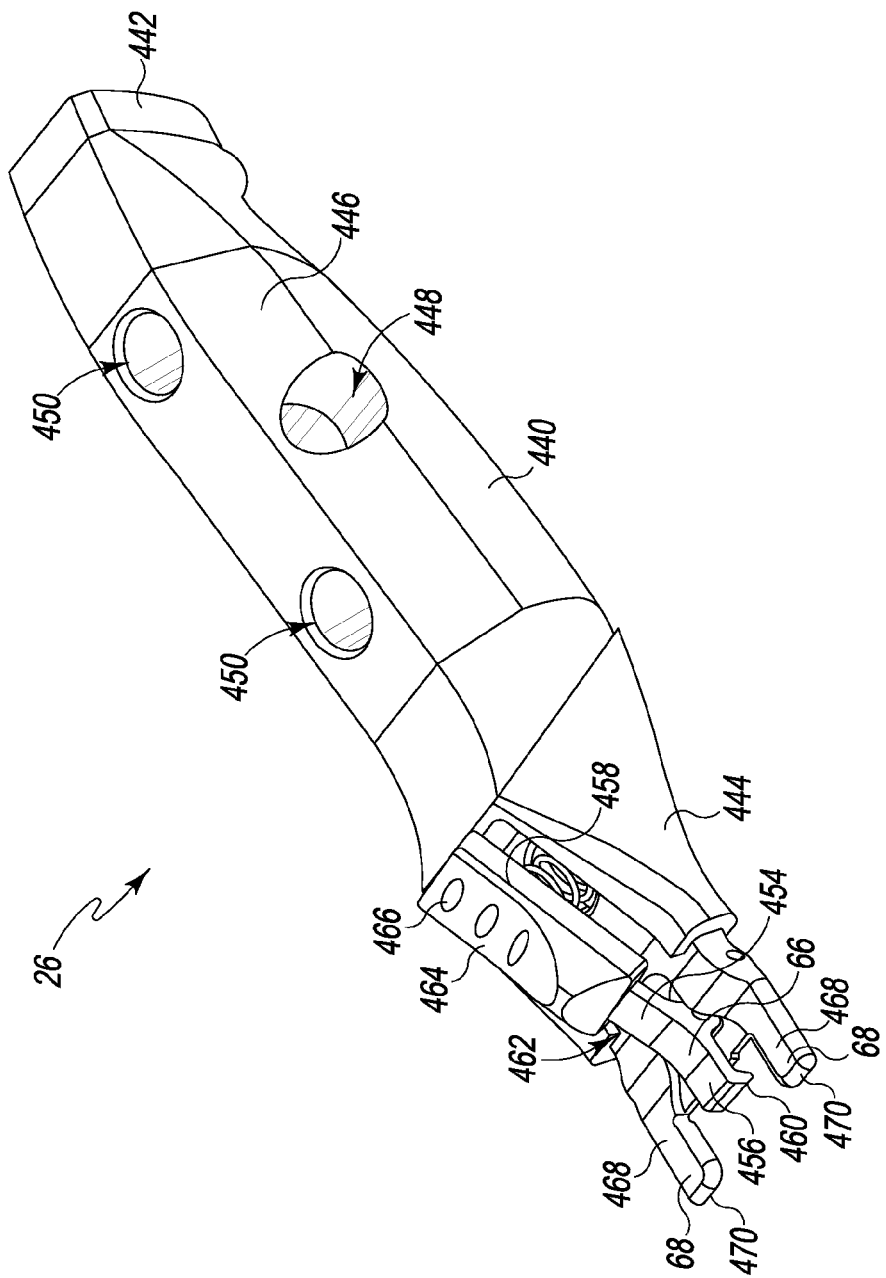
FIG. 17 is a perspective view of an alignment handle of the orthopaedic surgical instrument system of FIG. 1.

As described above, the system 10 further includes the detachable alignment handle 26, which the surgeon may use to adjust the position of the base trial 14. Referring now to FIG. 17, the alignment handle 26 includes an elongated body 440 and the lever 66, which is pivotally coupled to elongated body 440. The elongated body 440 has a back end 442 and a front end 444, and a grip 446 is positioned therebetween. A plurality of alignment rod holes 448, 450 extend through the elongated body 440, with the alignment rod hole 448 extending orthogonal to the alignment rod hole 450. As will be described in greater detail below, the holes 448, 450 are sized to receive a pair of alignment rods 662, 664 (see FIG. 30) that are used to confirm the overall alignment of the trial components 12 in the patient's knee.

The lever 66 of the alignment handle 26 includes a rocker arm 454 having a latching end 456 and an actuation end 458. A flange or catch 460 extends downwardly from the rocker arm 454 at the latching end 456. The catch 460 is sized to be received in the slot 60 of the base trial 14. The lever 66 is pivotally coupled to the body 440 via a joint 462. A biasing element (not shown) is positioned between actuation end 458 of the rocker arm 454 and the body 440. The lever 66 also includes a user-operated button 464 that is secured to the rocker arm 454 at the actuation end 458. In the illustrative embodiment, the button 464 includes a contoured outer surface 466 that is configured to receive a fingertip of a surgeon or other user.

As shown in FIG. 17, the pins 68 of the alignment handle 26 are positioned on each side of the lever 66. Each pin 68 has a body 468 that extends outwardly from the front end 444 of the elongated body 440 to a tip 470. The body 468 has an oblong-shaped cross section that corresponds to the oblong-shape of the apertures 64 defined in the base trial 14. As described above, each pin 68 is configured to be received in a corresponding aperture 64 defined in the base trial 14.

In use, the alignment handle 26 may be secured to the base trial 14 by positioning the tips 470 of the pins 68 in the apertures 64 defined in the base trial 14. The pins 68 may be then advanced into the apertures 64 to bring the catch 460 into contact with the sidewall 36 of the base trial 14. The bias exerted by the biasing element may be overcome by pressing down on the button 464, thereby causing the lever 66 to pivot about joint 462 and aligning the catch 460 with the channel 58 of the notch 54 defined in the base trial 14. The latching end 456 of the lever 66 may then be advanced into the notch 54. When the latching end 456 is positioned at the posterior end 62 of the notch 54, the catch 460 is positioned over the oblong-shaped slot 60. After the button 464 is released, the biasing element urges the lever 66 to pivot such that the catch 460 is advanced into the slot 60, thereby securing the base trial 14 to the alignment handle 26.

Figure 18:
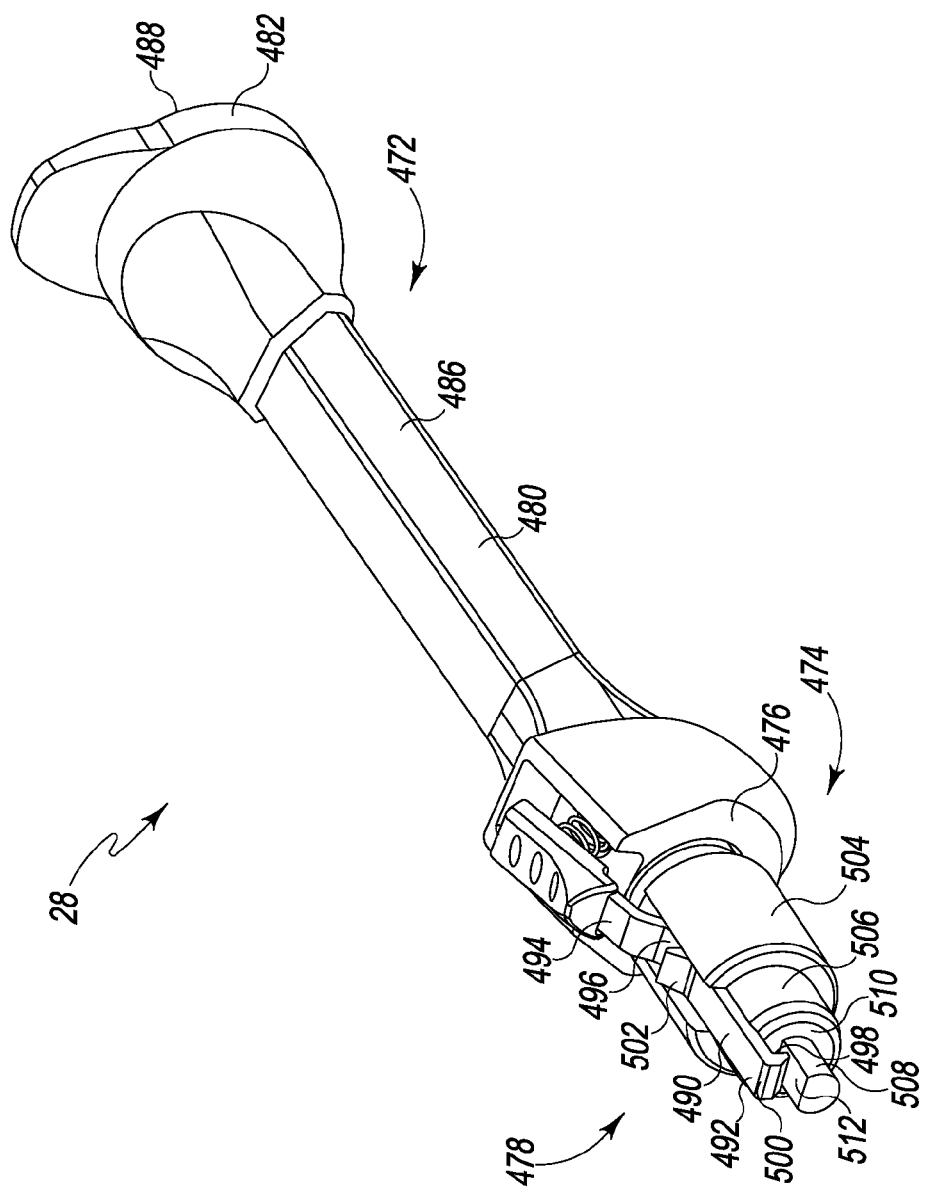
FIG. 18 is a perspective view of an impaction handle of the orthopaedic surgical instrument system of FIG. 1.

As described above, the system 10 also includes the impaction handle 28, which may be attached to the base insert 16, the keel punch 22, or the guide tower 24. Referring now to FIG. 18, the impaction handle 28 includes an elongated body 472, a mounting shaft 474 connected to an end 476 of the elongated body 472, and a attachment mechanism 478 configured to attach the base insert 16, the keel punch 22, or the guide tower 24 to the handle 28. The elongated body 472 includes a neck 480 extending from the end 476 and a head 482 connected to the neck 480 at the opposite end of the elongated body 472.

A grip 486 is secured to the neck 480 and is configured to receive the hand of a surgeon or other user. The head 482 of the impaction handle 28 includes a metal plate 488 positioned at the end 484. In use, the surgeon holds the impaction handle 28 via the grip 486 and strikes the metal plate 488 with a mallet, sledge, or other impaction tool to drive the keel punch 22 into the proximal end 604 of the patient's tibia 606.

The attachment mechanism 478 of the impaction handle 28 includes a lever 490 pivotally coupled to the mounting shaft 474. The lever 490 includes a latching arm 492 and an actuation arm 494 extending at an angle from an end 496 of the latching arm 492. The locking flange 498 is positioned at an opposite end 500 of the latching arm 492 and extends downwardly therefrom. As described above, the locking flange 498 is configured to engage the lip 100 of the base insert 16 or the keel punch 22 to secure the base insert 16 or the keel punch 22 to the impaction handle 28. Another locking flange or catch 502 is positioned adjacent to the end 496 of the latching arm 492. As will be described in greater detail below, the aperture 410 of the guide tower 24 is sized to receive the catch 502 such that the guide tower 24 may be secured to the impaction handle 28.

As shown in FIG. 18, the mounting shaft 474 of the impaction handle 28 includes a housing 504 extending from the end 476 of the elongated body 472 and a rod 506, which extends from the housing 504. A guide pin 508 of the impaction handle 28 extends from an end face 510 of the rod 506. The guide pin 508 has a cross section that substantially matches the shape of the opening 106 defined in the post 94 of the base insert 16 and the keel punch 22. As shown in FIG. 18, the guide pin 508 includes a flat face 512 that is sized to be received in the keyed section 114 of the inner wall 110 of the post 94.

The latching arm 492 of the lever 490 extends beyond the housing 504 such that the locking flange 498 is positioned over the guide pin 508 and extends toward the flat face 512. This arrangement permits the locking flange 498 to be positioned in the notch 104 of the post 94 and the guide pin 508 to be positioned in the opening 106 of the post 94 to secure the base insert 16 or the keel punch 22 to the impaction handle 28.

To secure, for example, the base insert 16 to the impaction handle 28, the guide pin 508 is positioned in the opening 106 of the post 94. By pressing down on the actuation arm 494 with a predetermined amount of force, the bias exerted by a biasing element may be overcome, thereby causing the lever 490 to pivot. As the lever 490 is pivoted, the locking flange 498 is moved away from the flat face 512 of the guide pin 508.

The guide pin 508 may be advanced along the passageway 112 of the base insert 16 until the top end 98 of the post 94 is placed in contact with the end face 510 of the rod 506. In that position, the locking flange 498 is positioned over the lever-receiving notch 104. When the actuation arm 494 is released, the lever 490 is urged to pivot by the biasing element and the locking flange 498 is advanced into the notch 104 of the base insert 16.

Figure 19:
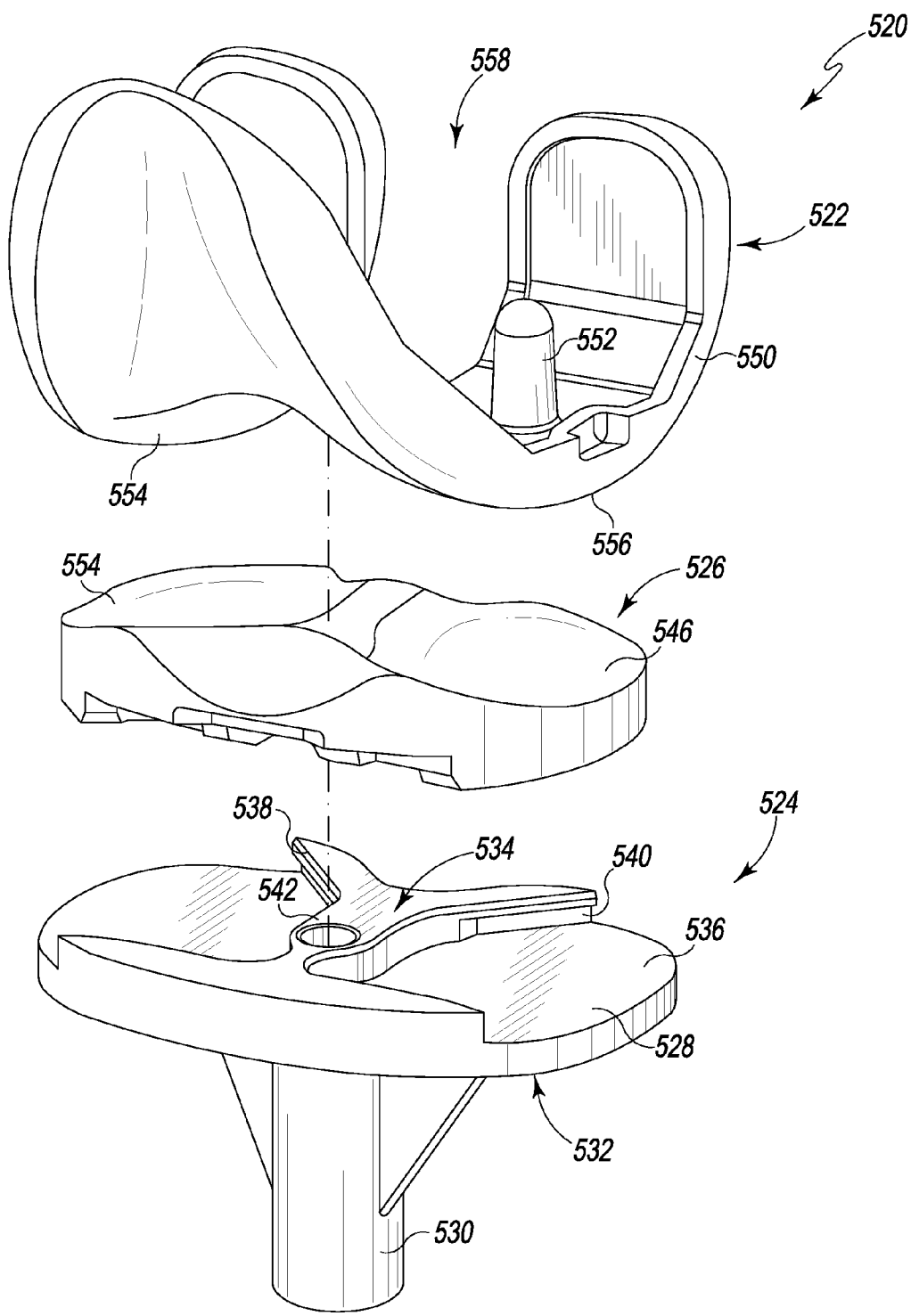
FIG. 19 is an exploded perspective view of one embodiment of a fixed bearing knee prosthesis.

Referring now to FIG. 19, one embodiment of a knee prosthesis (hereinafter fixed bearing knee prosthesis 520) that may replace the patient's natural joint is shown. The fixed bearing knee prosthesis 520 includes a femoral component 522, a tibial tray 524, and a tibial bearing 526. One example of a fixed bearing knee prosthesis is shown and described in U.S. Patent App. Pub. No. 2010/0063594, entitled "FIXED-BEARING KNEE PROSTHESIS HAVING INTER-CHANGEABLE COMPONENTS" by Stephen A. Hazebrouck et al., which is expressly incorporated herein by reference.

The tibial tray 524 includes a platform 528 having a fixation member, such as an elongated stem 530, extending away from its lower surface 532. The elongated tibial stem 530 is configured to be implanted into the surgically-prepared end 604 of a patient's tibia 606. A generally Y-shaped posterior buttress 534 extends upwardly from an upper surface 536 of the platform 528. The posterior buttress 534 includes a pair of arms 538, 540 extending along a posterior section of the perimeter of the platform 528. A third arm 542 extends anteriorly away from the intersection of the lateral arm 538 and the medial arm 540 (i.e., in a direction toward the center of the platform).

The bearing 526 is securable to the tibial tray 524. In particular, the bearing 526 may be snap-fit to the tibial tray 524. In such a way, the bearing 526 is fixed relative to the tibial tray 524 (i.e., it is not rotatable or moveable in the anterior-posterior or medial-lateral directions). The bearing 526 also includes a lateral bearing surface 544 and a medial bearing surface 546.

The femoral component 522 is configured to be implanted into a surgically-prepared end 600 of the patient's femur 602. Specifically, the femoral component 522 includes a body 550 having a pair of mounting lugs 552 extending therefrom. The mounting lugs 552 are configured to be received in the surgically-prepared end 600 of the patient's femur 602 to secure the femoral component 522 to the patient's femur 602.

The femoral component 522 is configured to emulate the configuration of the patient's natural femoral condyles. As such, the body 550 has a lateral condyle surface 554 and a medial condyle surface 556 that are configured (e.g., curved) in a manner that approximates the condyles of the natural femur. The surfaces 554, 556 are configured to articulate with the bearing surfaces 544, 546, respectively, of the bearing 526. The lateral condyle surface 554 and the medial condyle surface 556 are spaced apart from one another thereby defining an intercondylar notch 558 therebetween.

Figure 20:
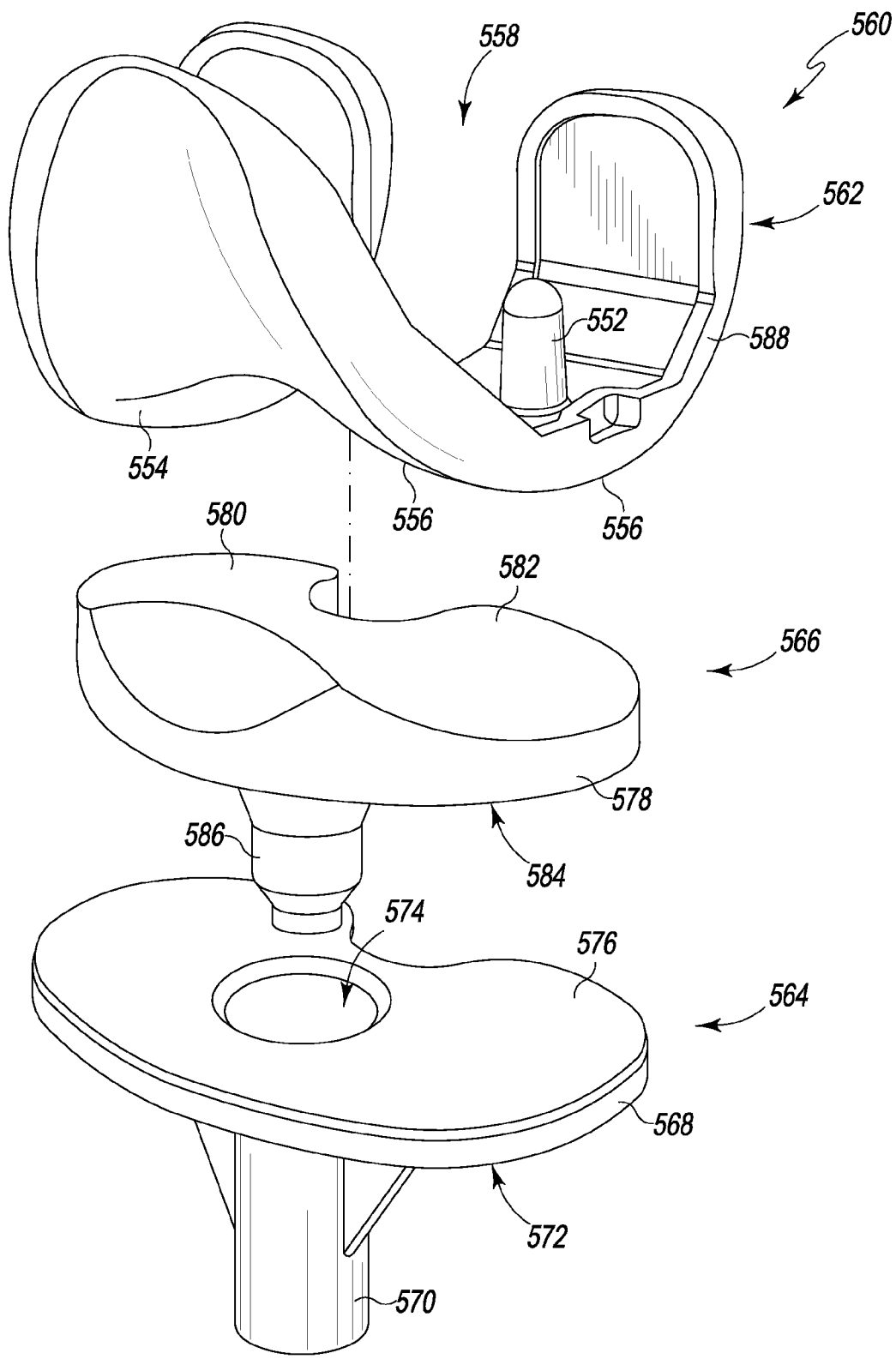
FIG. 20 is an exploded perspective view of one embodiment of a mobile bearing knee prosthesis.

Referring now to FIG. 20, another embodiment of a knee prosthesis (hereinafter mobile bearing knee prosthesis 560) that may replace the patient's natural joint is shown. The mobile bearing knee prosthesis 560 includes a femoral component 562, a tibial tray 564, and a tibial bearing 566. One example of a mobile bearing knee prosthesis is shown and described in U.S. Pat. No. 7,731,755 entitled "POSTERIOR STABILIZED MOBILE BEARING KNEE" by Joseph G. Wyss et al., which is expressly incorporated herein by reference.

The tibial tray 564 includes a platform 568 having a fixation member, such as an elongated stem 570, extending away from its lower surface 572. The elongated tibial stem 570 is configured to be implanted into the surgically-prepared end 604 of a patient's tibia 606. A cavity or bore 574 is defined in an upper surface 576 of the platform 568 and extends downwardly into the stem 570.

The bearing 566 is configured to be coupled to the tibial tray 564. The bearing includes a platform 578 having a lateral bearing surface 580, a medial bearing surface 582, and a bottom surface 584. The bearing 566 also includes a stem 586 extending downwardly from the bottom surface 584. When the bearing 566 is coupled to the tibial tray 564, the stem 586 of the bearing 566 is received in the bore 574 of the tibial tray 564. In that way, the tibial bearing 566 is configured to rotate about an axis defined by the stem 586 relative to the tibial tray 564.

The femoral component 562, like the femoral component 522 of the fixed bearing knee prosthesis 520, is configured to be implanted into a surgically-prepared end 600 of the patient's femur 602. Specifically, the femoral component 562 includes a body 588 having a pair of mounting lugs 552 extending therefrom. The mounting lugs 552 are configured to be received in the surgically-prepared end 600 of the patient's femur 602 to secure the femoral component 562 to the patient's femur 602.

The femoral component 562 is configured to emulate the configuration of the patient's natural femoral condyles. As such, the body 588 has a lateral condyle surface 554 and a medial condyle surface 556 that are configured (e.g., curved) in a manner that approximates the condyles of the natural femur. The surfaces 554, 556 are configured to articulate with the bearing surfaces 580, 582, respectively, of the bearing 566. The lateral condyle surface 554 and the medial condyle surface 556 are spaced apart from one another thereby defining an intercondylar notch 558 therebetween.

Figure 21:
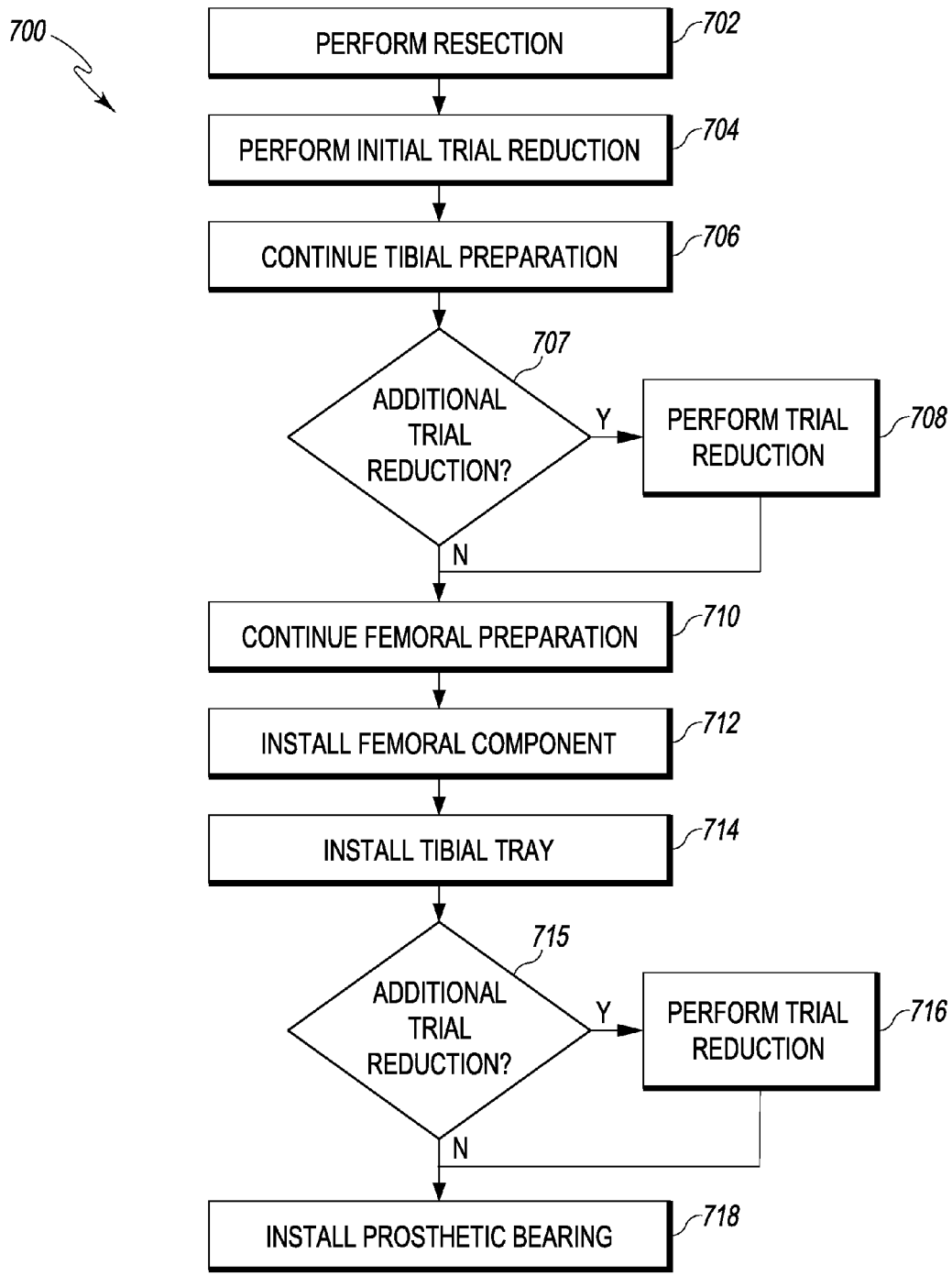
FIG. 21 is a simplified flow chart of one embodiment of a procedure utilizing the orthopaedic surgical instrument system of FIGS. 1-18.

The system 10 may be utilized during the performance of an orthopaedic surgical procedure similar to that shown in FIG. 21. As shown in FIGS. 22-32, the femoral trial 18 is attached to a distal end 600 of a patient's femur 602, and the tibial base trial 14 is attached to a proximal end 604 of a patient's tibia 606. A tibial bearing trial 20 is positioned on the tibial base trial 14 between the femoral trial 18 and the base trial 14 and a trial reduction is performed to determine the size and configuration of the knee prosthesis to be implanted.

In another part of the surgical procedure, the guide tower 24 of the system 10 is positioned on tibial base trial 14, and the surgeon uses the trial 14 and the tower 24 to guide, for example, a surgical drill while reaming the proximal end 604 of the patient's tibia 606. Thereafter, the keel punch 22 is impacted into the proximal end 604 of the patient's tibia 22 before the guide tower 24 is removed.

Figure 22:
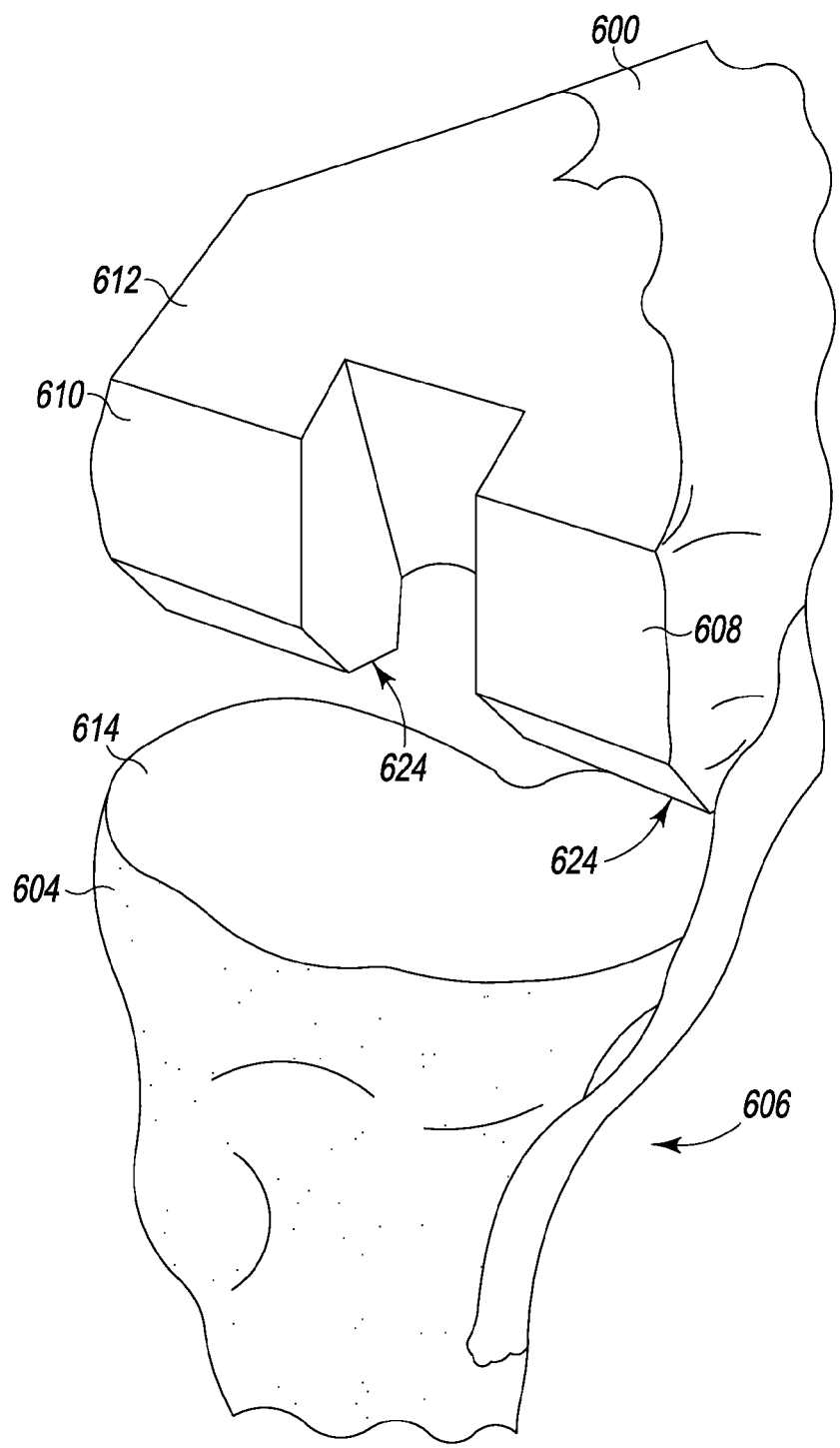
FIGS. 22-40 are views of a patient's femur, tibia, the knee prostheses of FIGS. 19 and 20, and the orthopaedic surgical instrument system of FIGS. 1-17 as the orthopaedic surgical instrument system is used in the procedure of FIG. 21.

Referring now to FIG. 21, an illustrative orthopaedic surgical procedure 700 utilizing the system 10 is shown. In block 702, the surgeon performs a resection of the distal end 600 of the patient's femur 602 and a resection of the proximal end 604 of the patient's tibia 606 to surgically prepare those ends for trial reduction. For example, as shown in FIG. 22, the patient's femur 602 and the patient's tibia 606 may be resected such that the surgically-prepared distal end 600 of the patient's femur 602 includes a resected medial condyle 608 and a resected lateral condyle 610. The resected medial condyle 608 and the resected lateral condyle 610 include a number of resected surfaces 612 configured to receive the femoral trial 18. Similarly, the surgically-prepared proximal end 604 of the patient's tibia 606 also includes a resected surface 614 configured to receive the tibial base trial 14.

Figure 23:
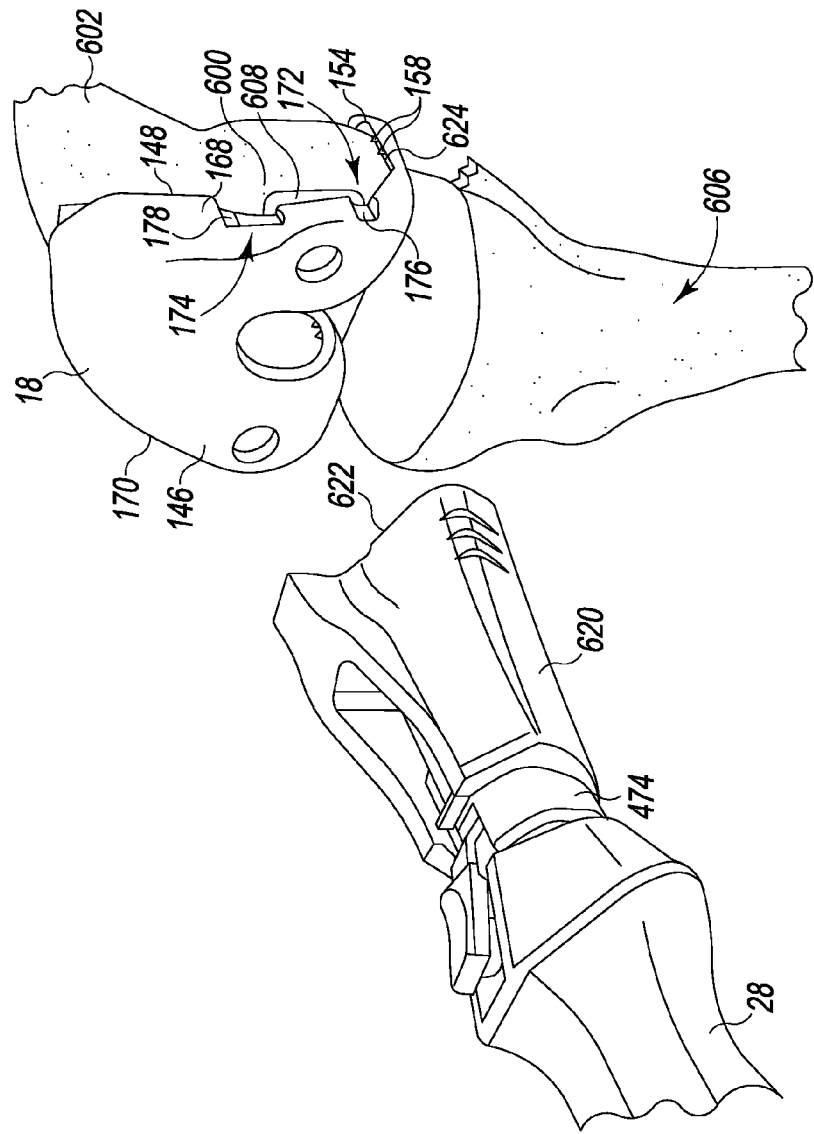

Returning to FIG. 21, the procedure 700 continues to block 704 in which the surgeon performs an initial trial reduction. In doing so, the surgeon uses the system 10 to evaluate and check the stability and kinematics of the patient's femur 602 and tibia 606 for implantation of a fixed bearing knee prosthesis 520 or a mobile bearing knee prosthesis 560. In the trial reduction process, the surgeon positions the femoral trial 18 over the distal end 600 of the patient's femur 602, as shown in FIG. 23. The impaction handle 28 may be used to tap the femoral trial 18 onto the distal end 600.

To do so, the surgeon may attach an impactor head 620 to the mounting shaft 474 of the impaction handle 28. The surgeon may position an engagement end 622 of the impactor head 620 in contact with the articular side 146 of the femoral trial 18 and apply force to the impaction handle 28 using the grip 486 or by tapping on the head 482 of the handle 28. The surgeon applies force until the fixation side 148 of the femoral trial 18 contacts the resected medial condyle 608 and the resected lateral condyle 610. Once the femoral trial 18 is properly positioned on the distal end 600 of the patient's femur 602, the surgeon may remove the impactor head 620 and the impaction handle 28. It should be appreciated that in other embodiments the surgeon may position the femoral trial 18 on the patient's femur 602 by hand without using the impaction handle 28.

When the femoral trial 18 is positioned on the distal end 600 of the patient's femur 602, the posterior fixation surfaces 154 of the femoral trial 18 engage posterior planar surfaces 624 of the patient's femur 602. One or more of the teeth 158 of the posterior fixation surfaces 154 of the femoral trial 18 engages with, or grips, the posterior planar surfaces 624 of the condyles 608, 610. The engagement of the teeth 158 with the posterior planar surfaces 624 secures the femoral trial 18 to the distal end 600 of the patient's femur 602.

As shown in FIG. 23, the sidewalls 168, 170 of the femoral trial 18 indicate where the outer edge of a standard femoral prosthetic component would be located on the resected condyles 608, 610. Conversely, the base surfaces 176, 178 of the notches 172, 174 in the femoral trial 18 indicate where the outer edge of a narrow femoral prosthetic component would be located. If the sidewalls 168, 170 extend beyond the condyles 608, 610, the surgeon may select the narrow femoral prosthetic component for implantation.

Figure 24:
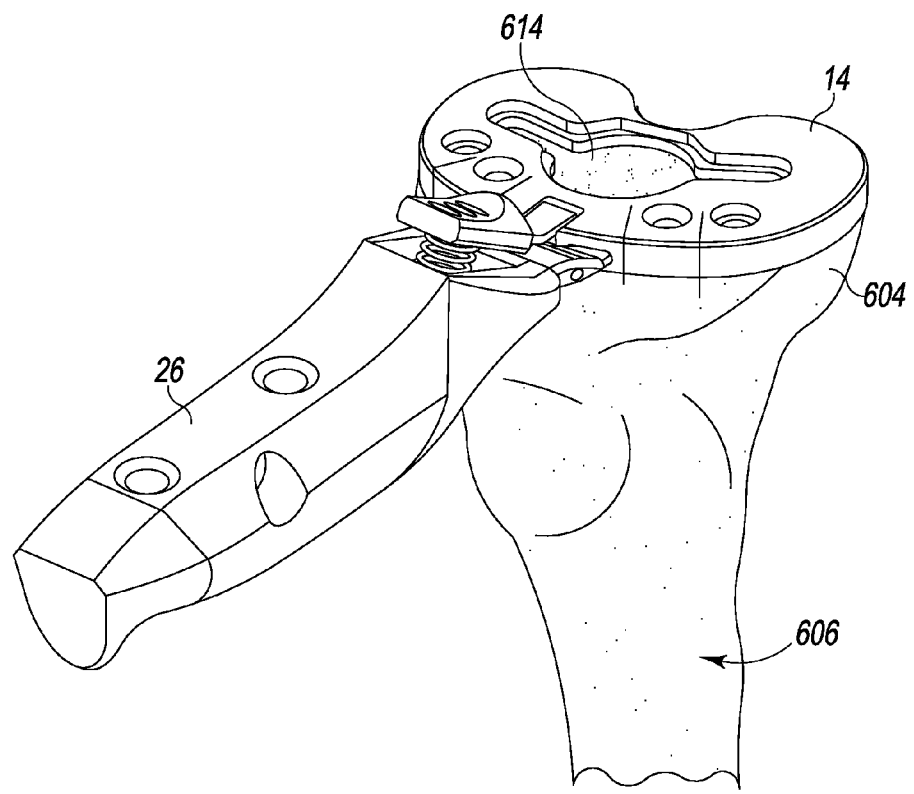

As shown in FIG. 24, the surgeon also positions the tibial base trial 14 on the resected surface 614 of the patient's tibia 606 during the trial reduction process. To do so, the surgeon may attach the alignment handle 26 to an appropriately-sized base trial 14 and, as shown in FIG. 24, use the alignment handle 26 to position the base trial 14 on the resected surface 614. Alternatively, the surgeon may choose to position the base trial 14 by hand. It should be appreciated that a number of base trials 14 may be provided, which are configured in a number of different sizes. As a result, the base trial 14 providing maximum coverage of the resected surface 614 of the patient's tibia 606 without overhang may be selected.

The surgeon may select one of the base inserts 16 to be placed in the plate opening 38 of the base trial 14. If the surgeon desires a fixed bearing trial 372, the surgeon may select a spikeless base insert 128 and position the base insert 128 in the plate opening 38 by hand so that the bottom surface 84 of the base insert 128 engages the shelf surface 52 of the base trial 14. If the surgeon desires a mobile bearing trial 374, the surgeon may select a spiked base insert 126, as shown in FIG. 25.

To position the spiked base insert 126 in the plate opening 38 of the base trial 14, the surgeon may attach the base insert 126 to the impaction handle 28. To do so, the surgeon positions the guide pin 508 of the impaction handle 28 in the opening 106 of the base insert 126 and presses on the actuation arm 494 of the lever 490 with a predetermined amount of force to overcome the bias exerted by the biasing element, thereby causing the lever 490 to pivot. As the lever 490 is pivoted, the locking flange 498 is moved away from the flat face 512 of the guide pin 508, and the guide pin 508 may be advanced along the passageway 112 defined in the base insert 126 until the top end 98 of the post 94 is placed in contact with the end face 510 of the impaction handle 28. In that position, the locking flange 498 is positioned over the lever-receiving notch 104. When the surgeon releases the actuation arm 494, the biasing element urges the lever 490 to pivot and the locking flange 498 is advanced into the notch 104, thereby securing the base insert 126 to the impaction handle 28.

Figure 25:
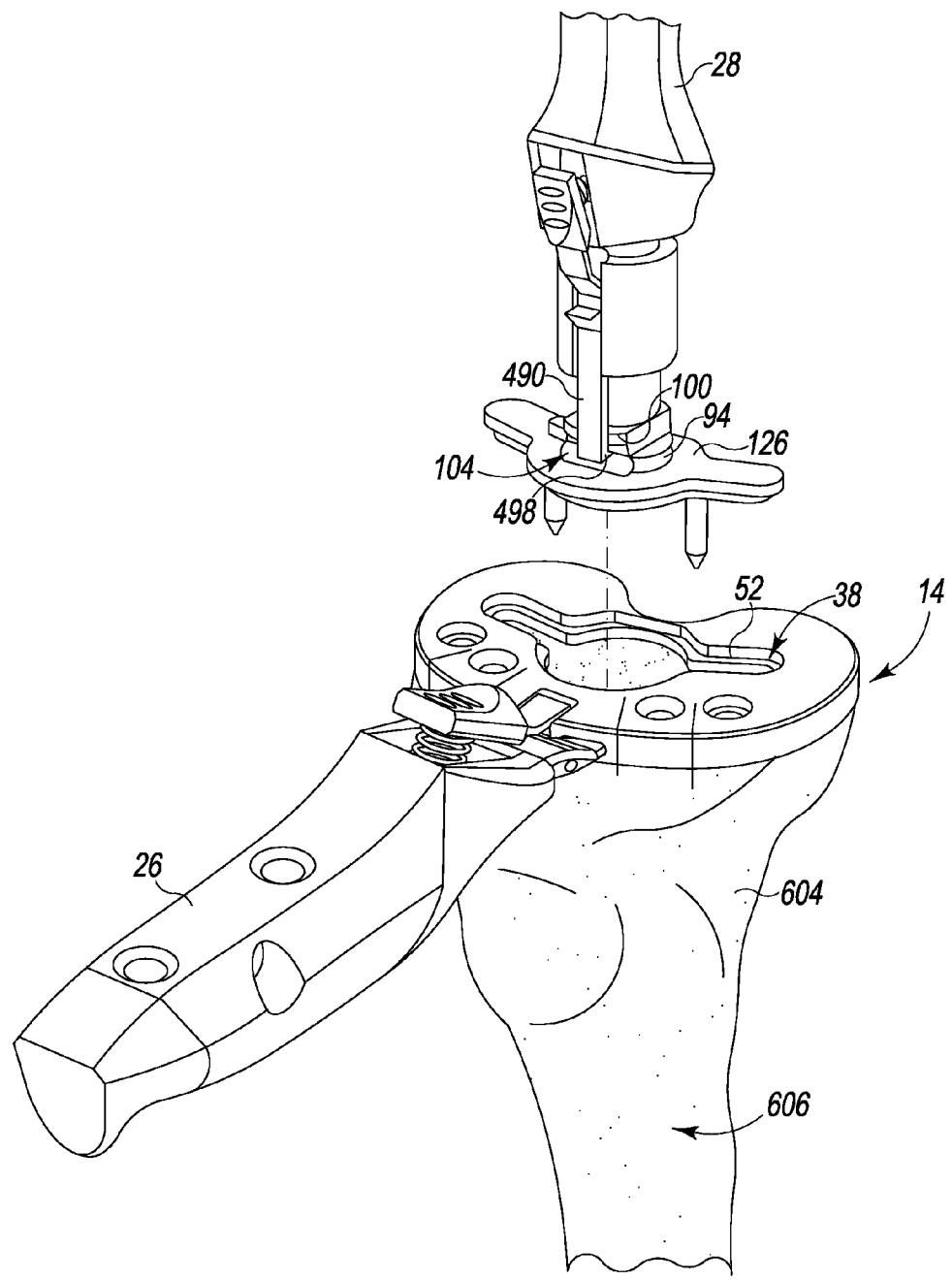

As shown in FIG. 25, the base insert 126 and impaction handle 28 are positioned over the plate opening 38, and the surgeon may then apply force to the handle 28 to tap the base insert 126 into the proximal end 604 of the patient's tibia 606. In doing so, the spikes 130 extending from the prongs 88, 90 of the base insert 126 are driven into the proximal end 604 of the patient's tibia 606. The surgeon continues driving the base insert 126 into the patient's tibia 606 until the bottom surface 84 of the base insert 126 engages the shelf surface 52 of the tibial base trial 14.

Once the selected base insert 16 (i.e., spiked or spikeless) is properly seated, the surgeon may select a trial shim 190 and a tibial bearing surface trial 192. If the surgeon desires a fixed bearing trial 372, a fixed bearing surface trial 300 may be selected and attached to one of the trial shims 190. To do so, the surgeon positions the trial shim 190 in the fixed bearing orientation shown in FIG. 26. Once the trial shim 190 is in the correct orientation, the surgeon attaches the trial shim 190 to the fixed bearing surface trial 300 by aligning the openings 258, 260 of the shim 190 with the pegs 270, 272, respectively, of the fixed bearing surface trial 300. The surgeon then advances the pegs 270, 272 into the respective openings 258, 260 such that the lower surface 304 of the fixed bearing surface trial 300 is placed in contact with the surface 196 of the shim 190 to assemble the fixed bearing trial 372.

Figure 26:
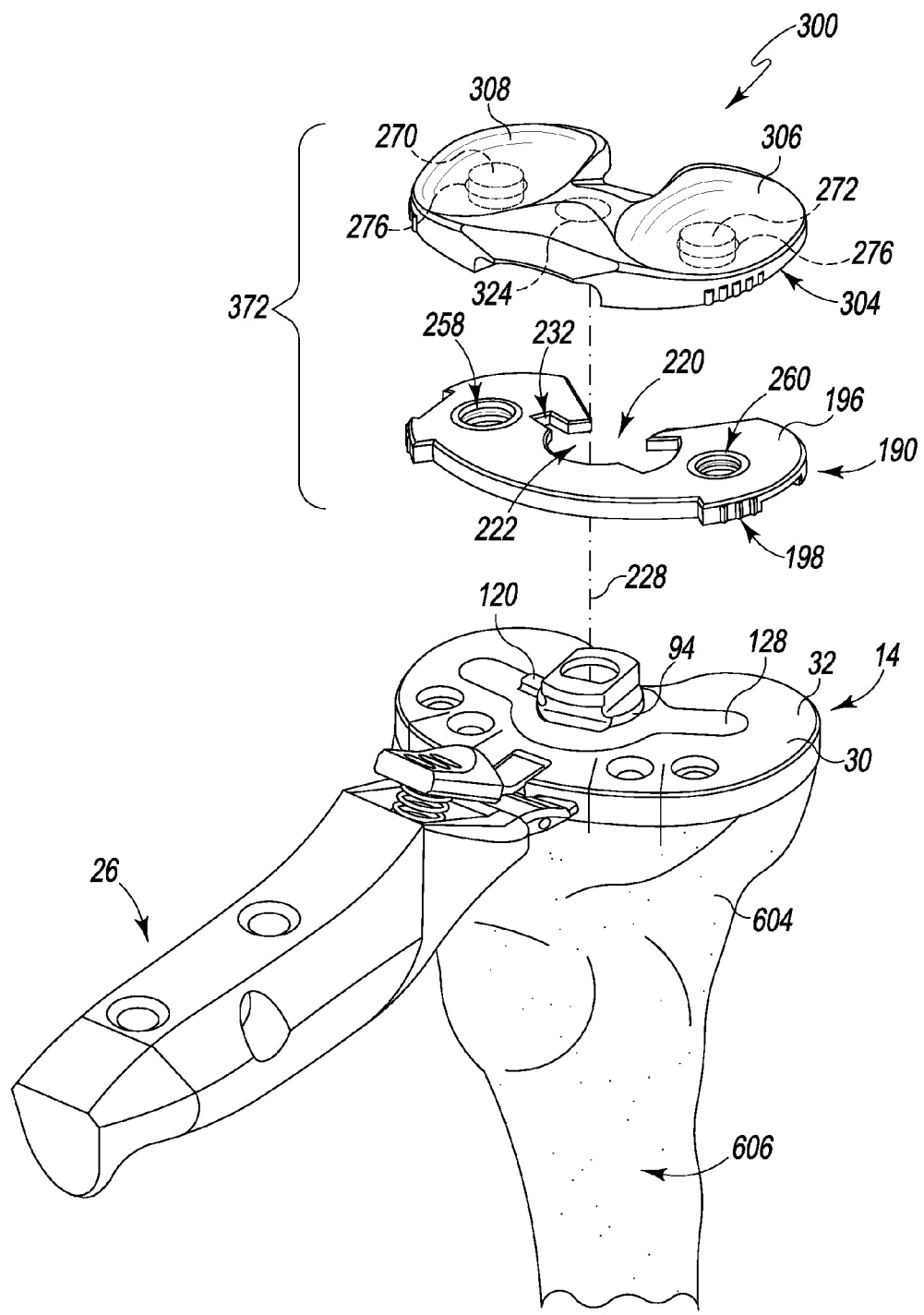

As shown in FIG. 26, the surgeon positions the fixed bearing trial 372 on the base trial 14 by aligning the apertures 220, 324 of the fixed bearing trial 372 with the post 94 and the lug 120 of the base insert 16. The surgeon then places the fixed bearing trial 372 over the post 94 and the lug 120 and advances the surface 198 of the shim 190 into contact with the upper surface 32 of the base trial 14. When properly seated, the lug 120 is received in the slot 232 of the shim 190 and the post 94 is received in the central passageway 222. The inner walls 240, 244 of the shim 190 cooperate with the lug 120 to prevent the fixed bearing trial 372 from rotating relative to the base trial 14.

Figure 27:
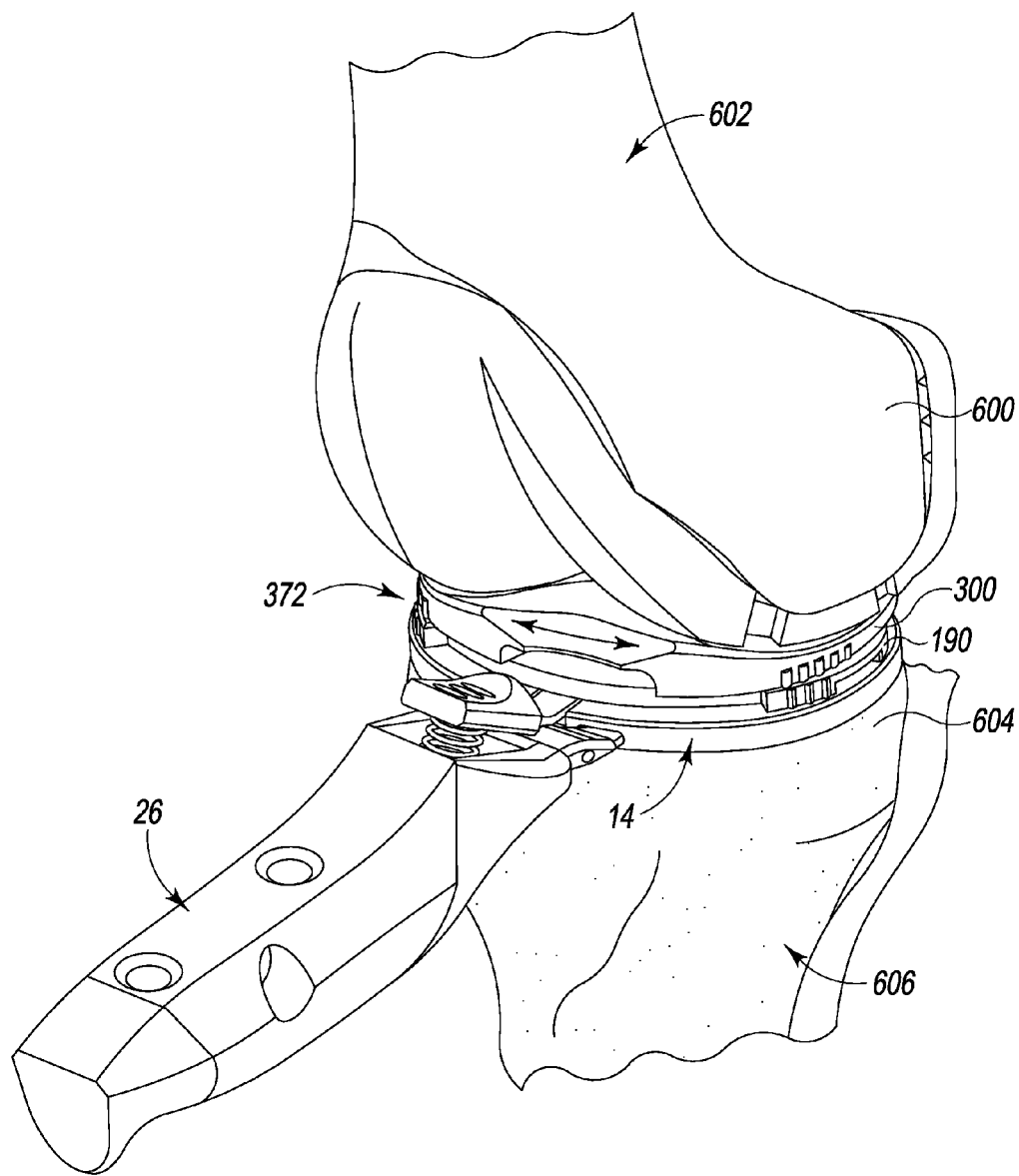

As shown in FIG. 27, when the fixed bearing trial 372 is in place, the surgeon carefully extends the knee of the patient, noting the anteroposterior stability, medial-lateral stability, and overall alignment in the anterior-posterior ("A/P") plane and medial-lateral ("M/L") plane. Rotational alignment of the tibial base trial 14 may be adjusted with the knee in full extension, using the handle 26 to rotate the trial 14 and the bearing trial 372 relative to the femoral trial 18. The rotation of the base trial 14 is usually centered on the junction between the medial and central one-third of the tibial tubercle.

Figure 30:
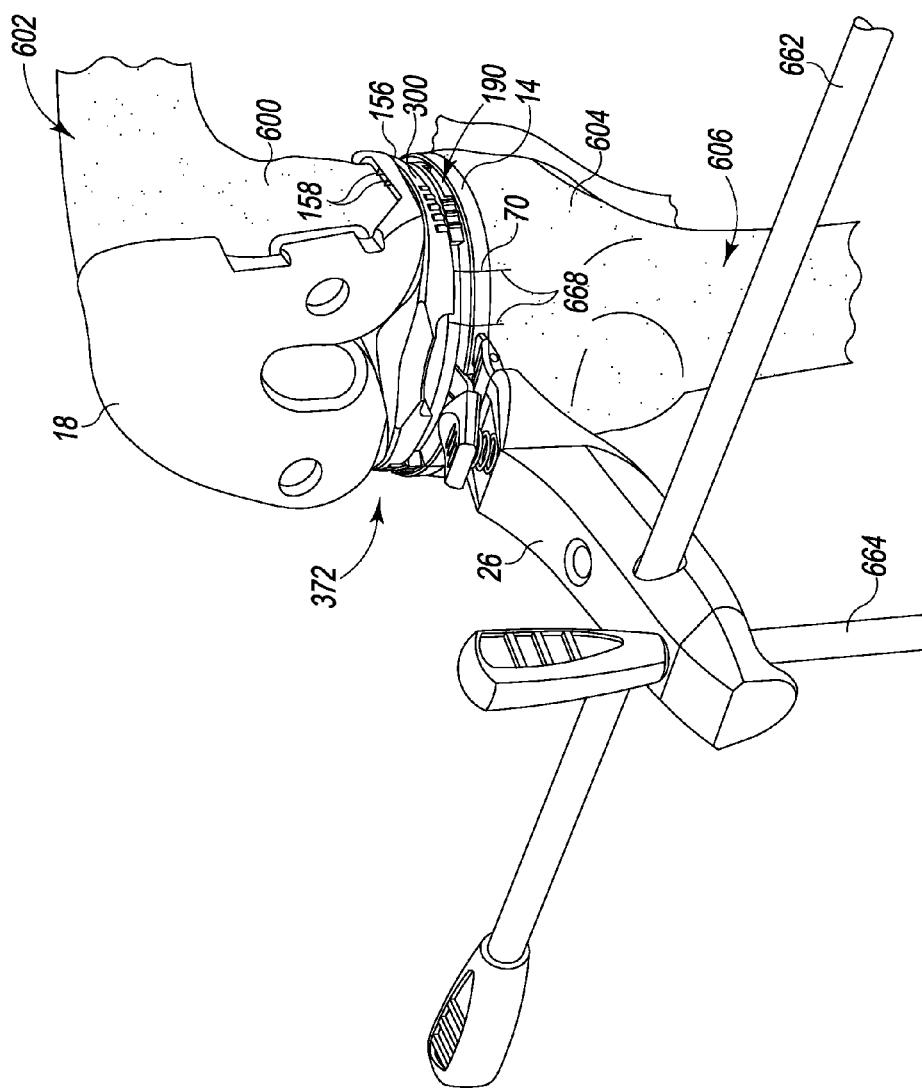

As the range of motion is evaluated, the load on the femoral trial 18 translates posteriorly as the knee is moved between extension (see FIG. 27) and flexion (see FIG. 30). As the load moves posteriorly, the force normal to the posterior condyle surfaces 156 of the femoral trial 18 increases, thereby causing the teeth 158 of the posterior fixation surfaces 154 of the femoral trial 18 to further engage, or grips, the posterior planar surfaces 624 of the surgically-prepared distal end 600 of the patient's femur 602. The engagement of one or more of the teeth 158 of the femoral trial 18 with the distal end 600 of the patient's femur 602 retains the femoral trial 18 on the patient's femur 602.

Figure 28:
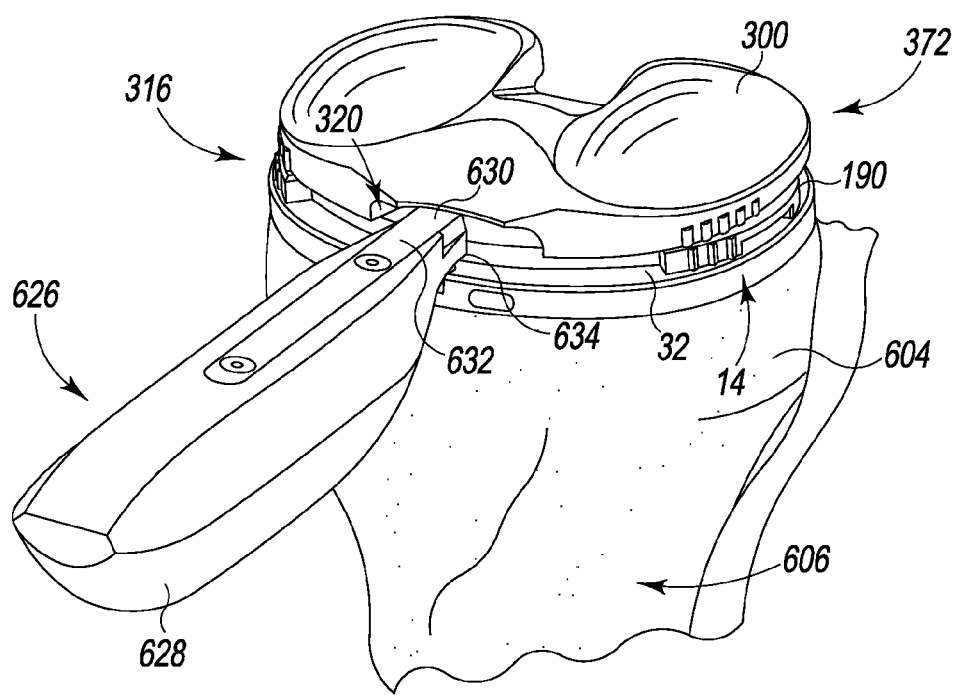

To improve performance, the surgeon may remove the fixed bearing trial 372 from the tibial base trial 14 to exchange the shim 190 or the bearing surface trial 192. As shown in FIG. 28, a removal tool 626 may be used to detach the fixed bearing trial 372 from the base trial 14. The removal tool 626 has an elongated body 628 and a tip 630 configured to be received in the notch 316 of the fixed bearing surface trial 300. When the tip 630 is positioned in the notch 316 of the shim 190, an upper surface 632 of the tip 630 contacts the bottom of the channel 320 of the shim 190 while a lower surface 634 of the tip 630 contacts the upper surface 32 of the base trial 14. The surgeon may then pivot the elongated body 628 of the removal tool 626 downward, thereby disengaging the fixed bearing trial 372 from the base trial 14.

Figure 29:
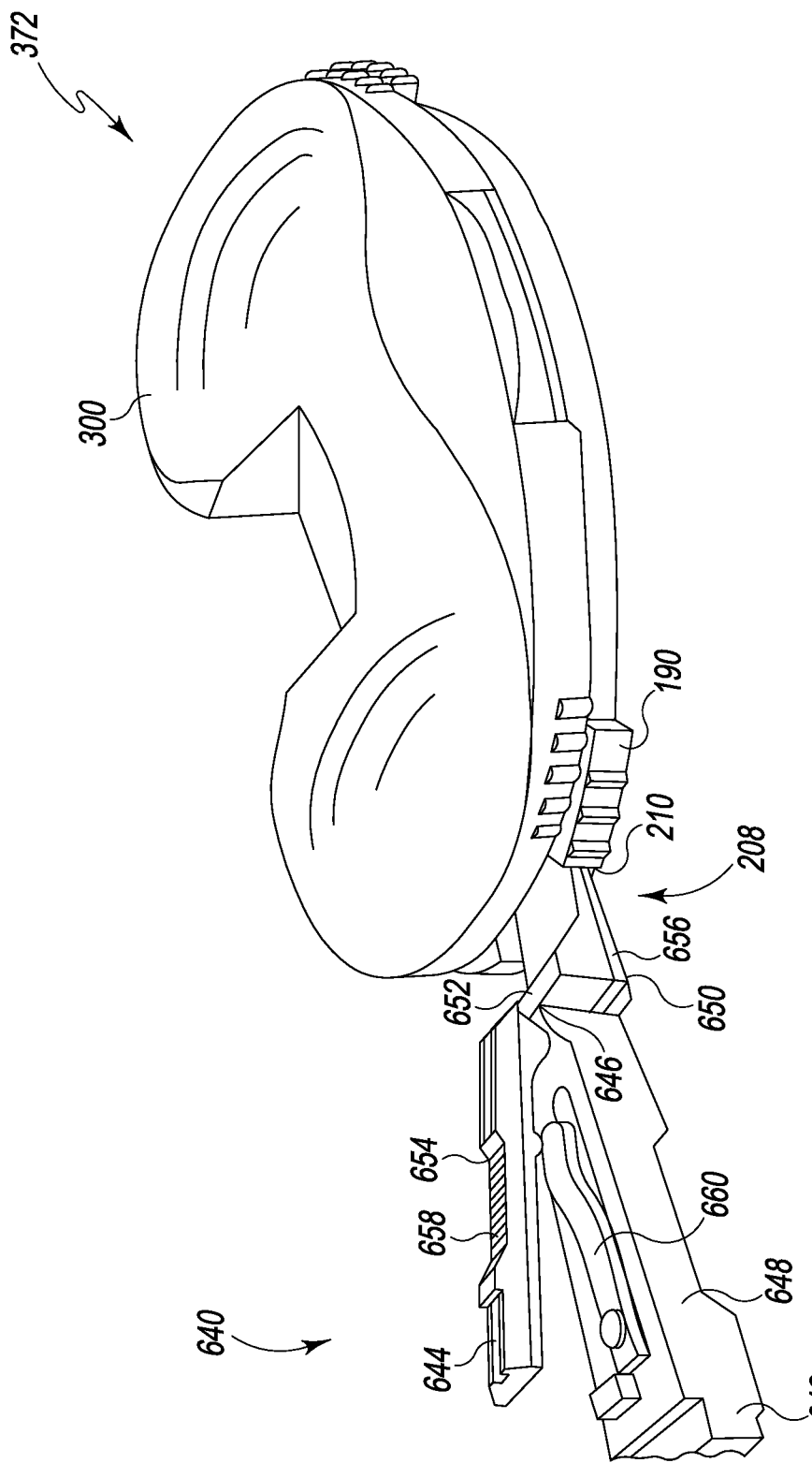

As shown in FIG. 29, the surgeon may use a separator tool 640 to detach the shim 190 from the fixed bearing surface trial 300. The separator tool 640 has a housing 642 and a lever 644 pivotally coupled to the housing 642 at a joint 646. The housing 642 includes a main body 648 and a plate 650 extending from the main body 648.

The lever 644 includes a lift arm 652 and an actuation arm 654. The lift arm 652 is wedge-shaped and includes a lower surface 656 configured to contact the plate 650. The actuation arm 654 includes a contoured upper surface 658 configured to receive the fingertip of the surgeon. A biasing element, illustratively embodied as a leaf spring 660, is positioned between the actuation arm 654 of the lever 644 and the main body 648 of the housing 642, thereby biasing the lift arm 652 in contact with the plate 650.

To detach the shim 190 from the fixed bearing surface trial 300, the surgeon positions the lift arm 652 and the plate 650 of the separator tool 640 in the notch 208 of the shim 190. By pressing down on the contoured upper surface 658 of the actuation arm 654, the surgeon may overcome the bias of leaf spring 660 and pivot the lever 644 about the joint 646. The lift arm 652 is advanced into contact with the lower surface 304 of the fixed bearing surface trial 300. As the surgeon continues to press down on the actuation arm 654, the pegs 270, 272 may be withdrawn from the openings 258, 260 and shim 190 may be separated from the fixed bearing surface trial 300.

The surgeon may then select another shim 190 having a different thickness or choose a fixed bearing surface trial 300 with an alternative configuration, such as, for example, a fixed bearing surface trial 300 that is cruciate retaining or posterior stabilized. In some cases, the surgeon may switch to a mobile bearing surface trial 340. The surgeon may continue to try various combinations of shims 190 and bearing surface trials 192 to ascertain which final implant will have the best stability in flexion and extension while permitting full extension.

As shown in FIG. 30, the surgeon may confirm overall alignment with two alignment rods 662, 664. The alignment rod 662 is positioned in the hole 448 while the alignment rod 664 is positioned in one of the holes 450 extending through the handle 26. Once a combination is selected and the appropriate position on the patient's tibia is located, the surgeon may etch marks 668 on the anterior tibial cortex using, for example, an electrocautery tool (not shown). The marks 668 are aligned with the alignment etchings 70 defined in the anterior aspect 56 of the tibial base trial 14.

If the surgeon desires instead a mobile bearing trial 374, a mobile bearing surface trial 340 may be selected and attached to one of the trial shims 190. To do so, the surgeon positions the trial shim 190 in the mobile bearing orientation shown in FIG. 31. Once the trial shim 190 is in the correct orientation, the surgeon attaches the trial shim 190 to the mobile bearing surface trial 340 by aligning the openings 258, 260 of the shim 190 with the pegs 270, 272, respectively, of the mobile bearing surface trial 340. The surgeon then advances the pegs 270, 272 into the respective openings 258, 260 such that the lower surface 346 of the mobile bearing surface trial 340 is placed in contact with the surface 198 of the shim 190, thereby assembling the mobile bearing trial 374.

Figure 31:
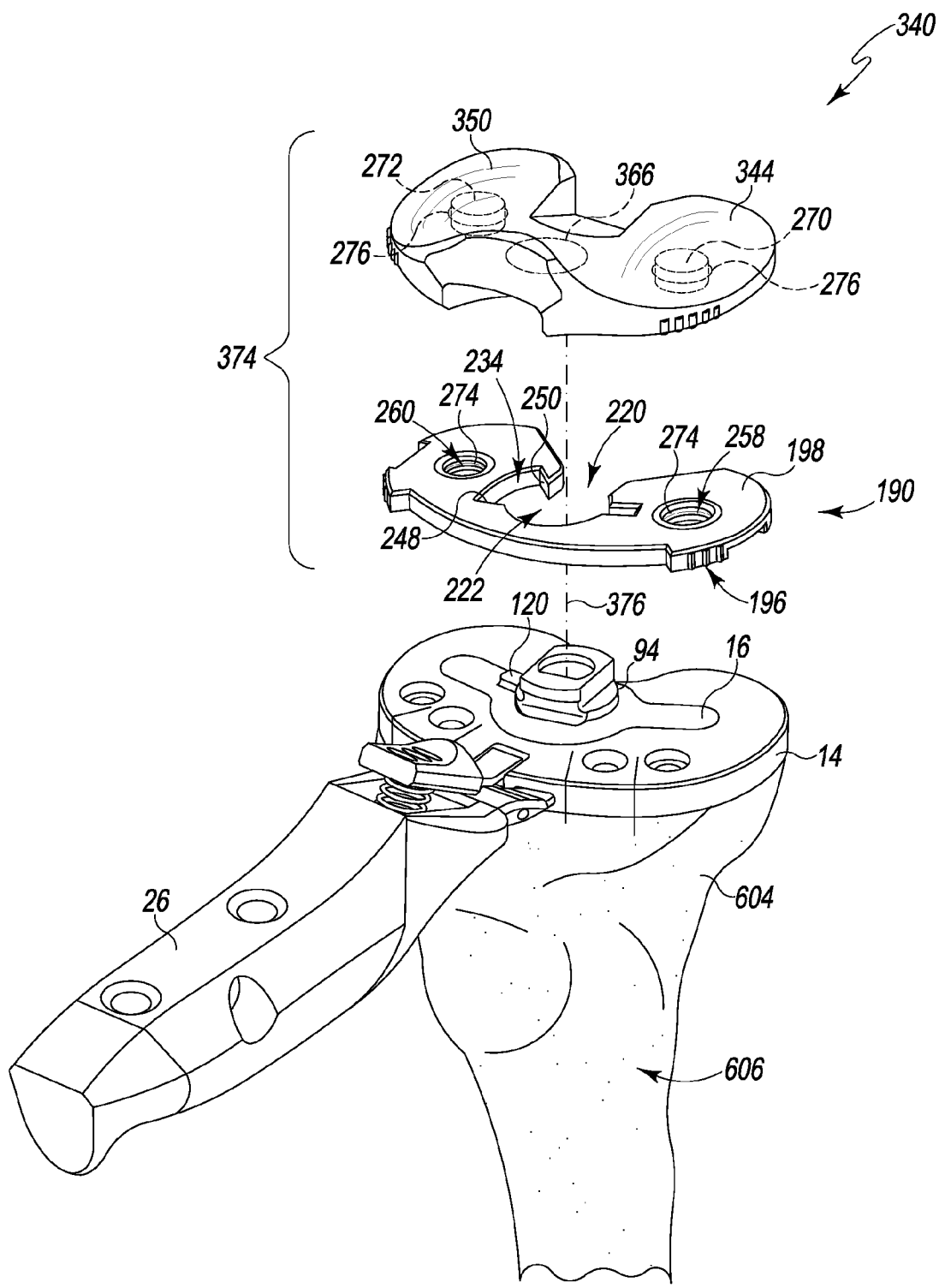

As shown in FIG. 31, the surgeon positions the mobile bearing trial 374 on the base trial 14 by aligning the apertures 220, 366 of the mobile bearing trial 374 with the post 94 and the lug 120 of the base insert 16. The surgeon then places the mobile bearing trial 374 over the post 94 and the lug 120 and advances the surface 196 of the shim 190 into contact with the upper surface 32 of the base trial 14. When properly seated, the lug 120 is received in the slot 234 of the shim 190 and the post 94 is received in the central passageway 222.

Figure 32:
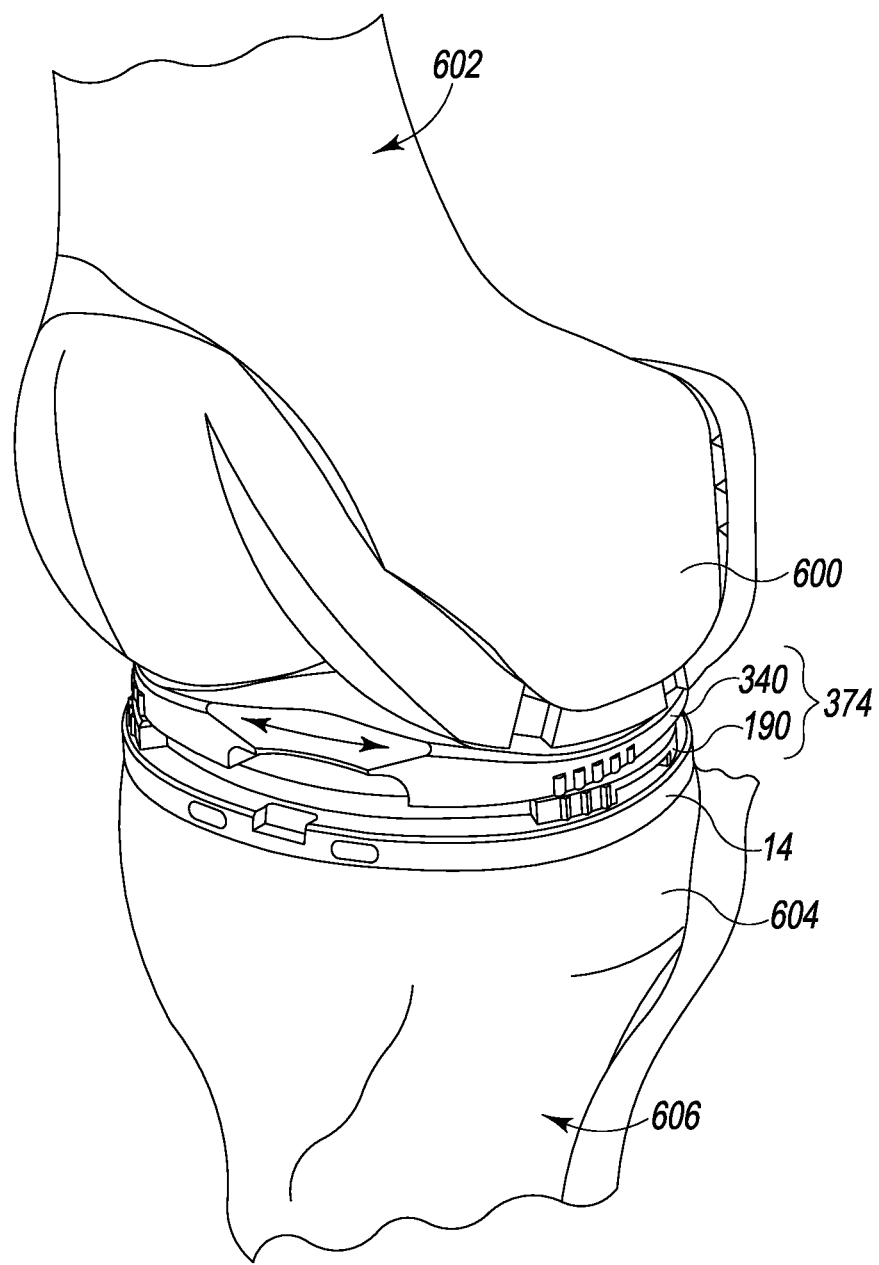

With the femoral trial 18, tibial base trial 14, and mobile bearing trial 374 in place, the surgeon may extend the knee and note the anteroposterior stability, medial-lateral stability, and overall alignment in the A/P and M/L planes, as shown in FIG. 32. The surgeon is also able to assess the bearing rotation and patellofemoral tracking because the mobile bearing trial 374 is rotatable about the base trial 14. As discussed above, when the mobile bearing trial 374 is attached to the base trial 14, the post 94 defines a longitudinal axis 376 extending along the passageway 112 of the base insert 16. The arcuate slot 234 of the shim 190 permits the mobile bearing trial 374 to rotate relative to the base trial 14 about the axis 376. When the mobile bearing trial 374 is rotated in one direction, the lug 120 may be advanced along the arcuate inner wall 252 into contact with the inner wall 248 of the shim 190; when the mobile bearing trial 374 is rotated in the opposite direction, the lug 120 may be advanced along the arcuate inner wall 252 into contact with the inner wall 250.

Overall alignment can be confirmed by attaching alignment rods 662, 664 to the handle 26, which is reattached to the base trial 14. If there is any indication of instability, the surgeon may remove the mobile bearing trial 374 from the tibial base trial 14 using the removal tool 626 and disassemble the trial 374 using the separator tool 640 to exchange the shim 190 or the bearing surface trial 192. For example, the surgeon may select the next greater thickness shim 190 before repeating the trial reduction. The surgeon may continue to try various combinations of shims 190 and bearing surface trials 192 to ascertain which implant size and configuration (e.g., the thickness of the implant, the mobility of the implant, etc.) will have the best stability in flexion and extension while permitting the desired kinematics.

Figure 33:
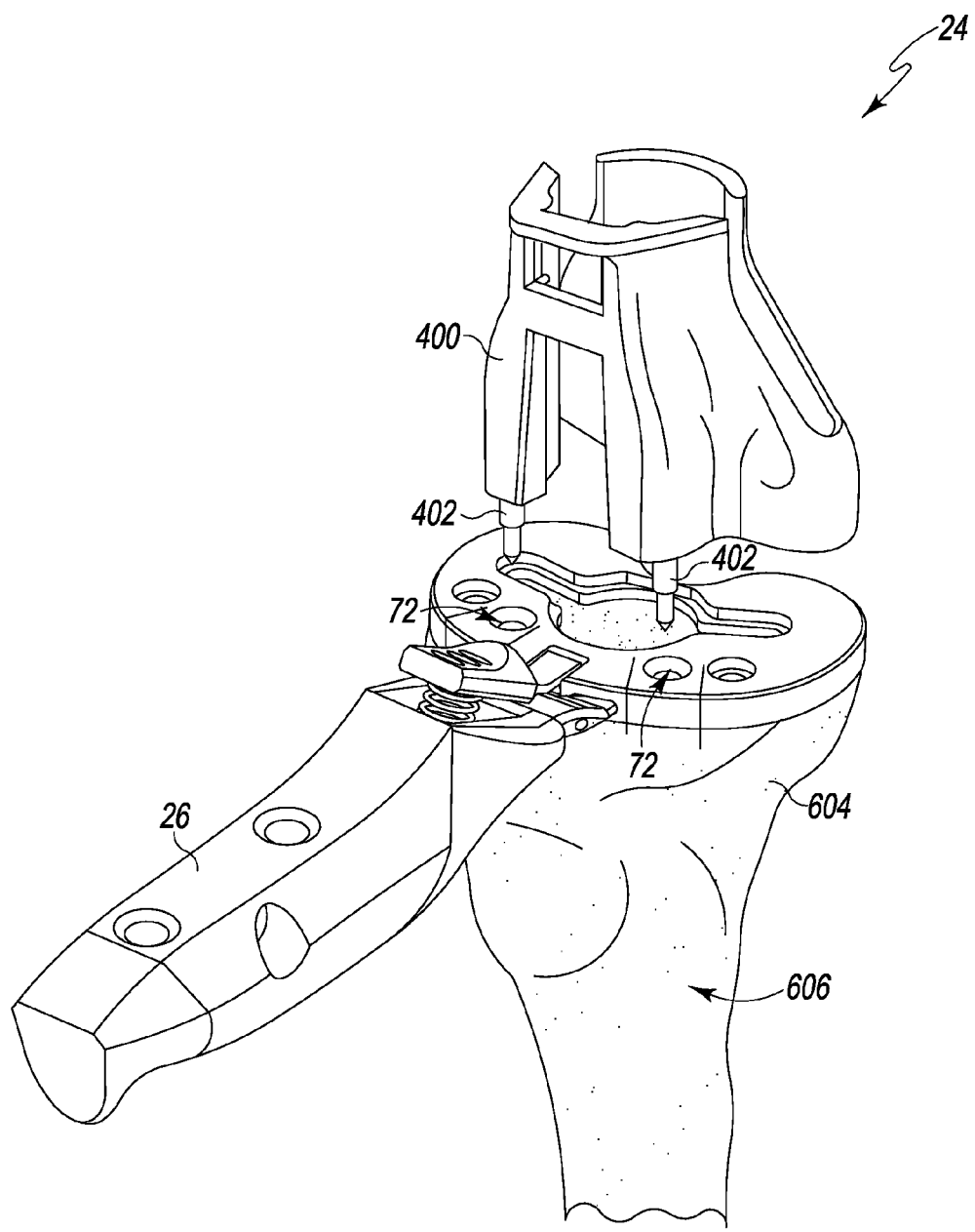
Figure 34:
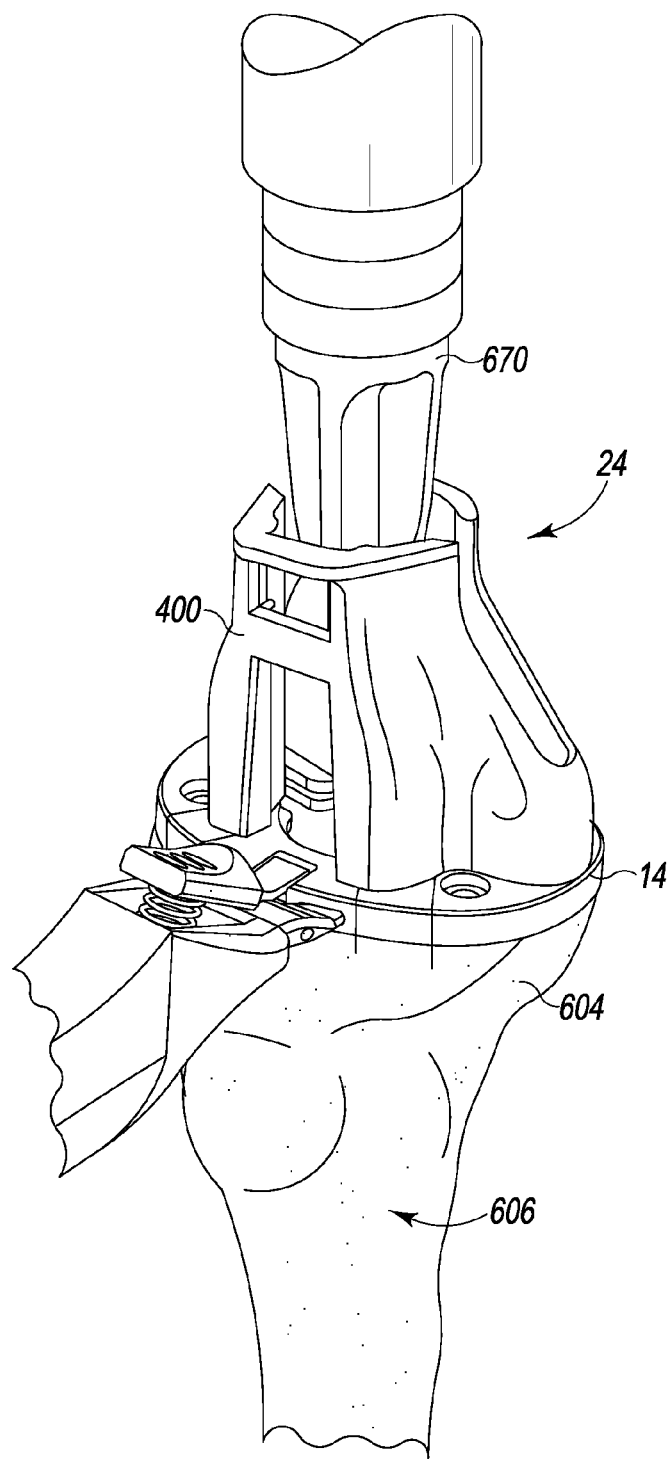
Figure 35:
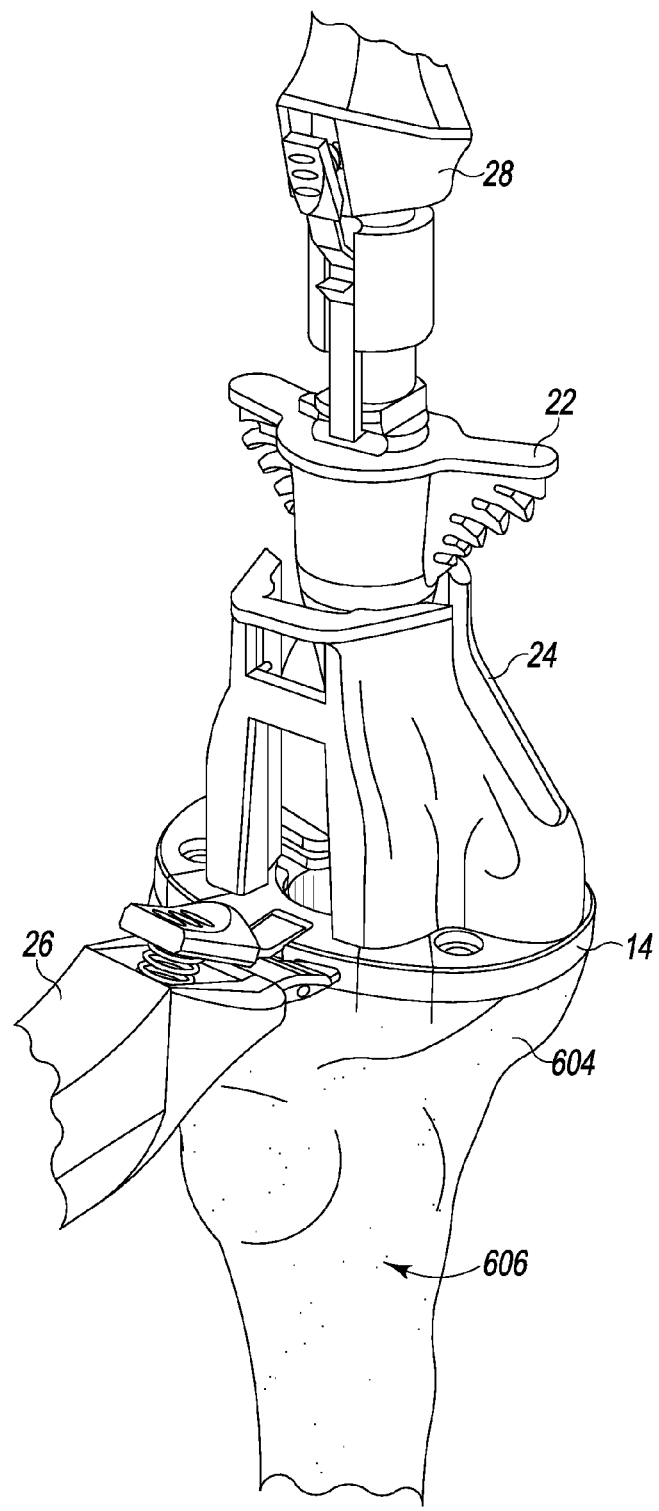

Returning back to FIG. 21, after the surgeon has performed the trial reduction of block 704, the procedure 700 proceeds to block 706 in which further surgical preparation of the proximal end 604 of the patient's tibia 606 is performed. Specifically, as shown in FIG. 33, the guide tower 24 is positioned on tibial base trial 14 so that fixation pins 402 extend through the fastener holes 72 of the tibial base trial 14 and into the proximal end 604 of the patient's tibia 606. As shown in FIG. 34, the surgeon uses the base trial 14 and the tower 24 to guide, for example, a surgical drill 670 while reaming the proximal end 604 of the patient's tibia 606. Thereafter, as shown in FIG. 35, the keel punch 22 is impacted into the proximal end 604 of the patient's tibia 606 using the impaction handle 28 before the guide tower 24 is removed. An exemplary procedure for reaming the patient's tibia 606 and installing the keel punch 22 is set forth in U.S. Patent App. Ser. No. 61/503,331, entitled "METHOD OF SURGICALLY PREPARING A TIBIA FOR IMPLANTATION OF A PROSTHETIC COMPONENT" filed by David Waite et al., which is incorporated herein by reference.

Figure 36:
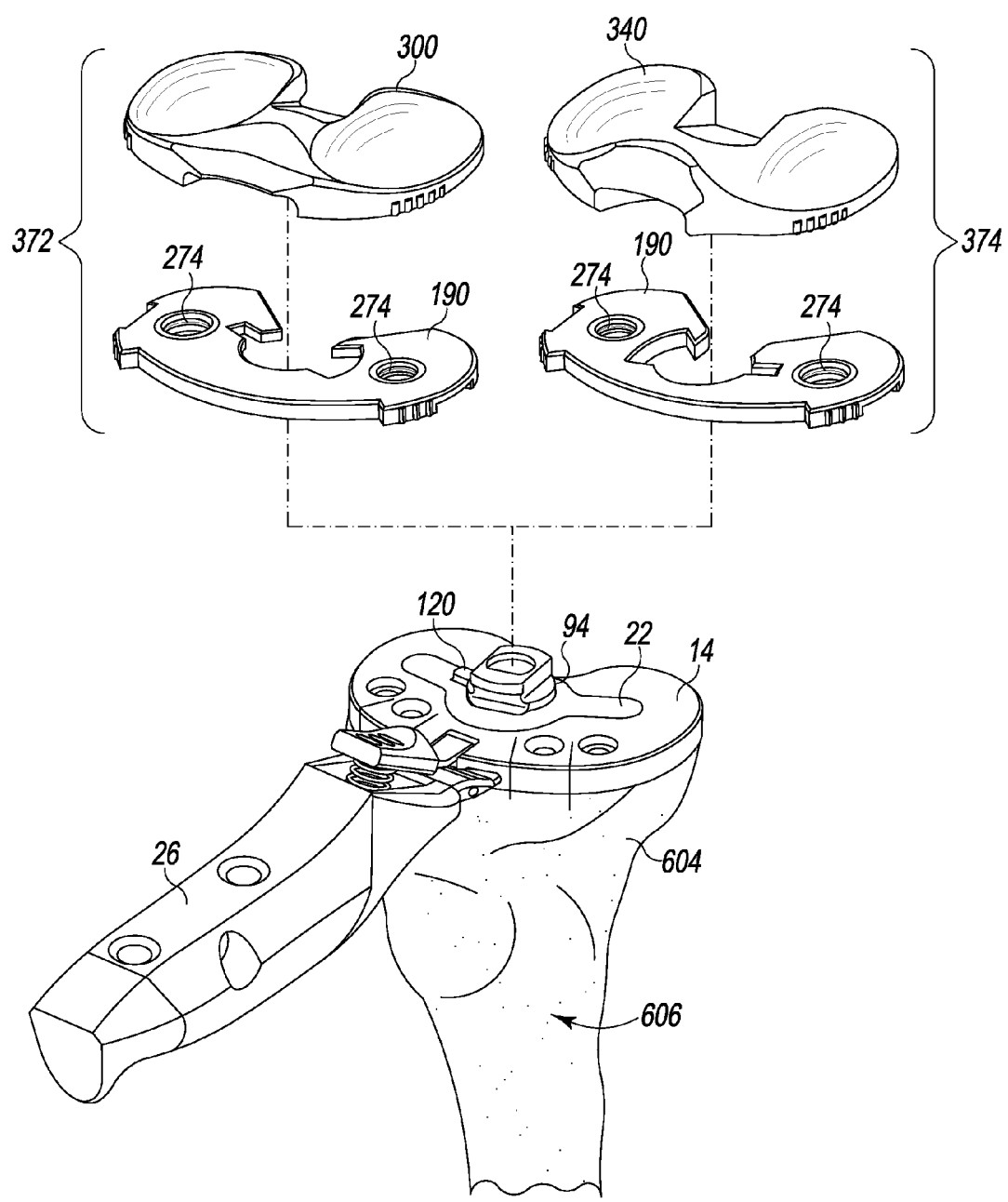

Subsequently, in block 707, the surgeon determines whether any additional trial reduction is necessary. If so, the procedure 700 continues to block 708 in which the surgeon may utilize the keel punch 22 seated on the tibial base trial 14 in the proximal end 604 of the patient's tibia 606 to perform an additional trial reduction. As shown in FIG. 36, the surgeon may assemble a fixed bearing trial 372 or a mobile bearing trial 374 and position the trial 372 or trial 374 over the post 94 and the lug 120 of the keel punch 22. If a fixed bearing trial 372 is selected, the surgeon advances the surface 198 of the shim 190 into contact with the upper surface 32 of the base trial 14. When properly seated, the lug 120 of the keel punch 22 is received in the slot 232 of the shim 190 and the post 94 is received in the central passageway 222 of the shim 190.

With the fixed bearing trial 372 in place, the knee is again extended and the surgeon may note the anteroposterior stability, medial-lateral stability, and overall alignment in the A/P and M/L planes. Overall alignment can be confirmed by attaching alignment rods 662, 664 to the handle 26. If there is any indication of instability, the surgeon may remove the fixed bearing trial 372 from the tibial base trial 14 using the removal tool 626 and disassemble the trial 372 using the separator tool 640 to exchange the shim 190 or the bearing surface trial 192. The surgeon may then repeat the trial reduction until satisfied with the alignment and the stability of the knee.

If a mobile bearing trial 374 is selected, the surgeon advances the surface 196 of the shim 190 into contact with the upper surface 32 of the base trial 14. When properly seated, the lug 120 of the keel punch 22 is received in the slot 234 of the shim 190 and the post 94 is received in the central passageway 222. With the mobile bearing trial 374 in place, the knee is again extended and the surgeon may note the anteroposterior stability, medial-lateral stability, and overall alignment in the A/P and M/L planes. Overall alignment can be confirmed by attaching alignment rods 662, 664 to the handle 26. If there is any indication of instability, the surgeon may remove the mobile bearing trial 374 from the tibial base trial 14 using the removal tool 626 and disassemble the trial 374 using the separator tool 640 to exchange the shim 190 or the bearing surface trial 192. The surgeon may then repeat the trial reduction until satisfied with the alignment and the stability of the knee.

Figure 37:
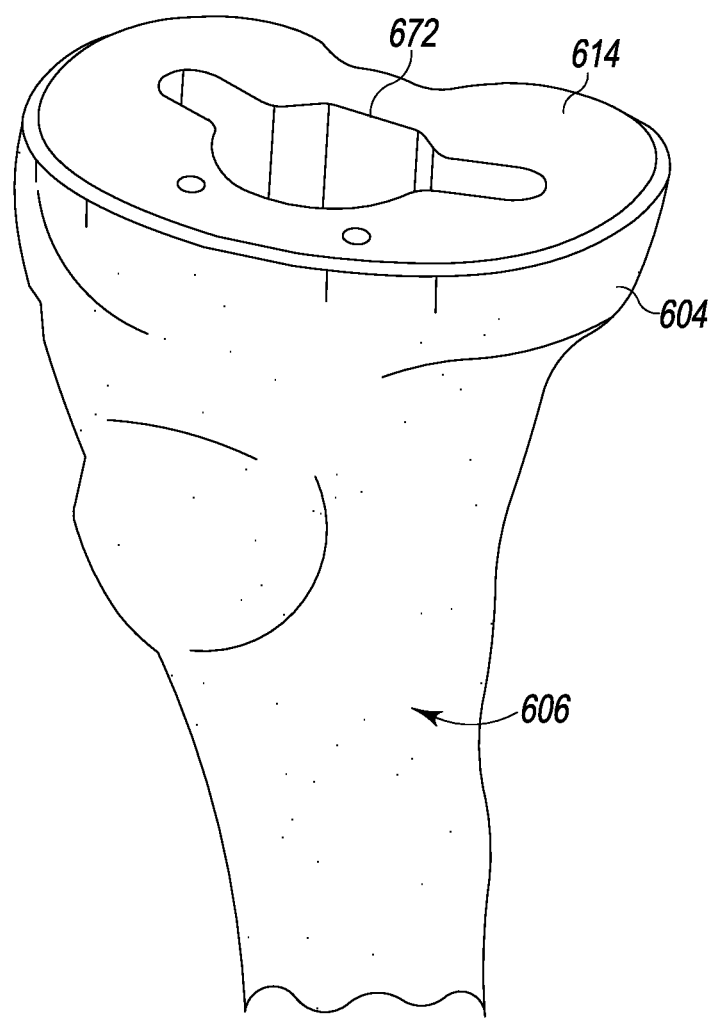

When the additional trial reduction of block 708 is complete or if the surgeon determines in block 707 that an additional trial reduction is not needed, the surgeon may use the impaction handle 28 to remove the keel punch 22 from the patient's tibia 606. As shown in FIG. 37, the resultant features, including an opening 672, of the proximal end 604 of the patient's tibia 606 are configured to receive a tibial tray, such as the tray 524 of the fixed bearing knee prosthesis 520 or the tray 564 of the mobile bearing knee prosthesis 560.

Figure 38:
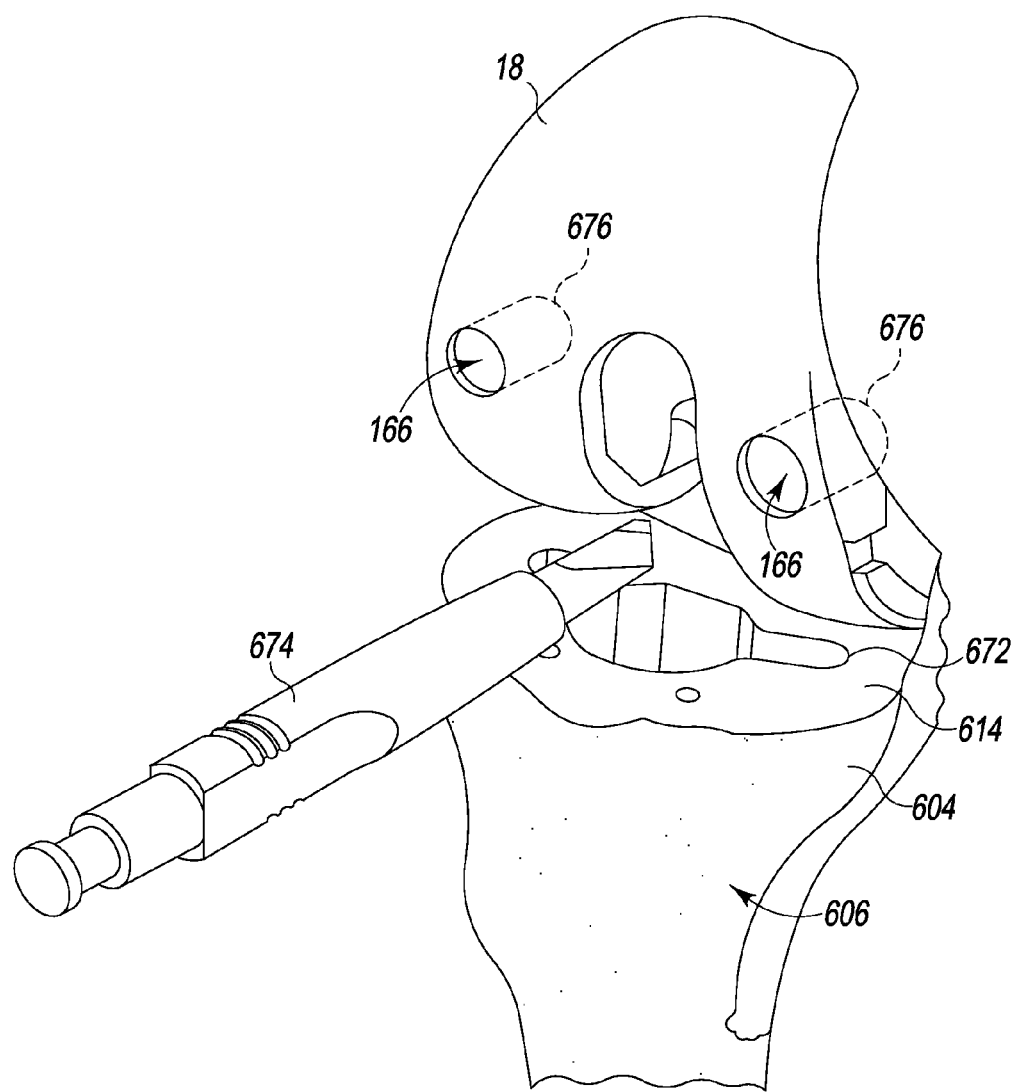

In block 710 of the procedure 700, further surgical preparation of the distal end 600 of the patient's femur 602 is performed. As shown in FIG. 38, the surgeon positions the femoral trial 18 on the distal end 600 of the patient's femur 602. The distal fixation surfaces 162 are advanced into contact with the condyles 608, 610 of the patient's femur 602. A surgical drill 674 is advanced sequentially through the through-holes 166 defined in the femoral trial 18 to drill a hole 676 in each of the condyles 608, 610. Each hole 676 is sized to receive a corresponding lug 552 of the femoral component 522 of the fixed bearing knee prosthesis 520 or the femoral component 562 of the mobile bearing knee prosthesis 560. In block 712 of the surgical procedure 700, the surgeon may attach the selected femoral component of the knee prosthesis to the distal end 600 of the patient's femur 602.

In block 714 of the surgical procedure 700, the surgeon attaches the selected tibial tray (e.g., tibial tray 524 or tibial tray 564) to the proximal end 604 of the patient's tibia 606. To do so, the surgeon inserts the stem (e.g., stem 530 of the tibial tray 524 or stem 570 of the tibial tray 564) into the opening 672 defined in the resected surface 614 of the proximal end 604 of the patient's tibia 606. The surgeon may attach a tibial impactor (not shown) to the impaction handle 28, and, with the selected tibial tray fully seated, the surgeon may tap on the head 482 of the impaction handle 28 with a mallet or other instrument. It should be appreciated that the selected tibial tray may be press fit into the tibia 606 or, alternatively, may be secured to the tibia 606 by use of bone cement.

Figure 39:
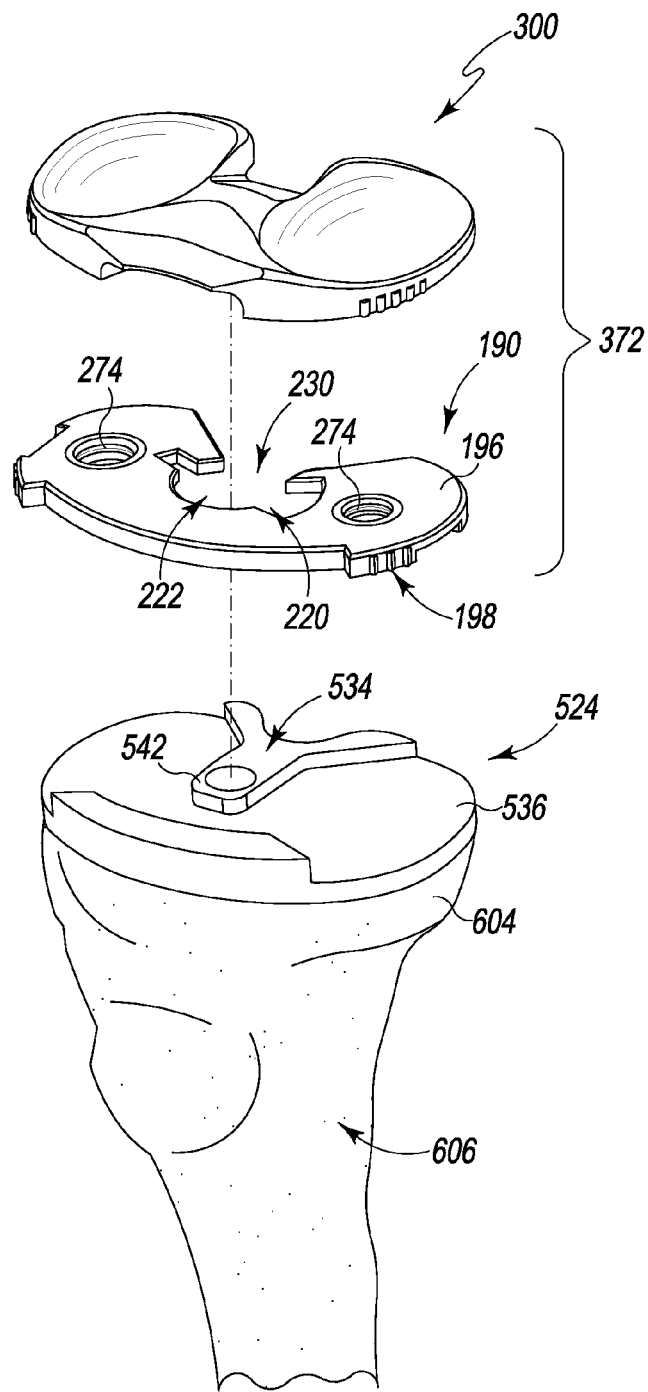

Subsequently, in block 715, the surgeon determines whether an additional trial reduction is necessary. If the surgeon determines that a trial reduction is needed, the procedure 700 continues to block 716 in which the surgeon may perform an additional trial reduction with the selected tibial tray installed in the patient's tibia 606 and the selected femoral component installed on the patient's femur 602. If the surgeon has selected the fixed bearing knee prosthesis 520, the surgeon again selects a fixed bearing trial 372 for the trial reduction. As shown in FIG. 39, the tibial tray 524 of the fixed bearing knee prosthesis 520 is installed in the proximal end 604 of the patient's tibia 606. The surgeon attaches the fixed bearing surface trial 300 to the shim 190 to assemble to the fixed bearing trial 372 and positions the fixed bearing trial 372 over the tibial tray 524. The surface 198 of the shim 190 is then advanced into contact with the upper surface 536 of the tibial tray 524. When properly seated, the third arm 542 of the posterior buttress 534 of the tibial tray 524 is positioned in the slot 230 and the central passageway 222 of the shim 190.

With the fixed bearing trial 372 in place on the tibial tray 524, the knee is again extended and the surgeon may note the anteroposterior stability, medial-lateral stability, and overall alignment in the A/P and M/L planes. Overall alignment can be confirmed by attaching alignment rods 662, 664 to the handle 26. If there is any indication of instability, the surgeon may remove the fixed bearing trial 372 from the tibial tray 524 using the removal tool 626 and disassemble the trial 372 using the separator tool 640 to exchange the shim 190 or the bearing surface trial 192. The surgeon may then repeat the trial reduction until satisfied with the alignment and the stability of the knee.

Figure 40:
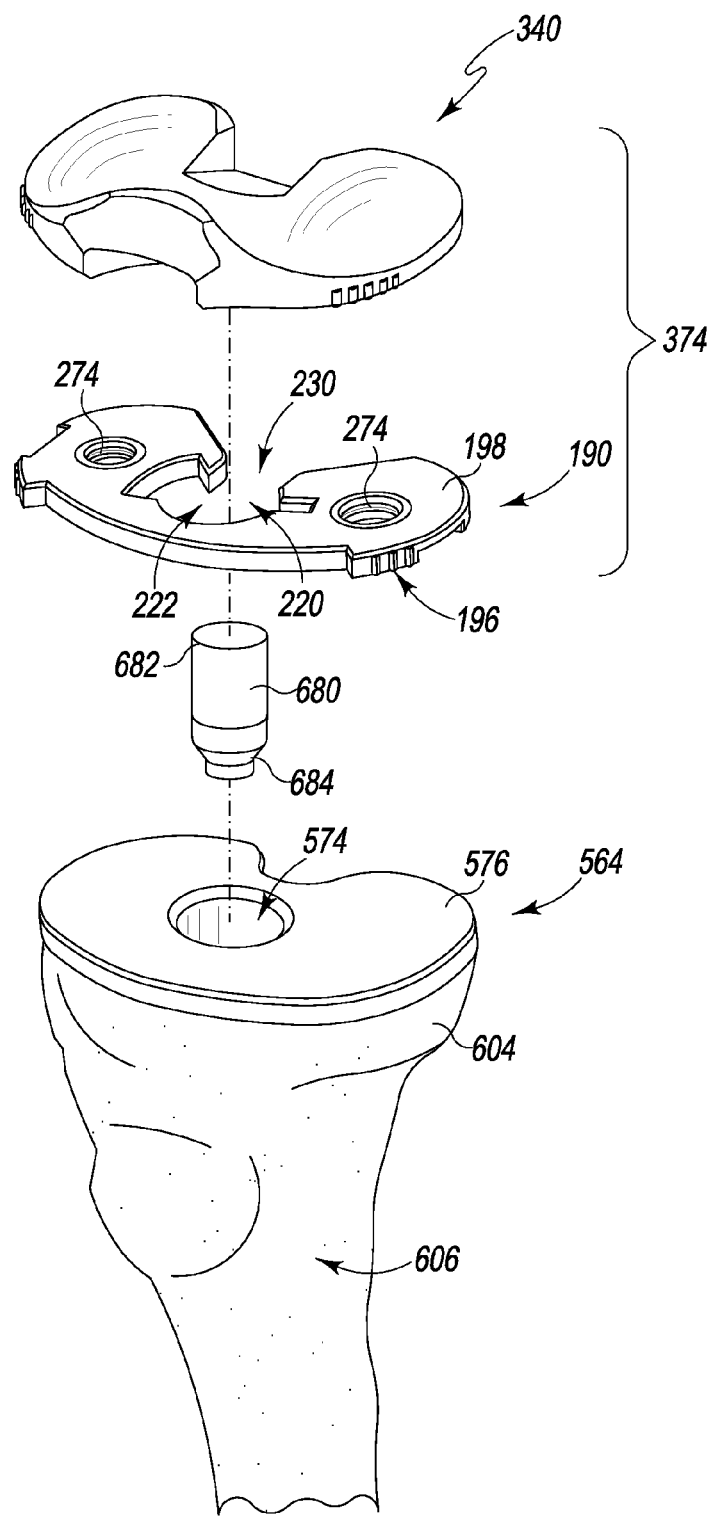

Alternatively, if the surgeon has selected the mobile bearing knee prosthesis 560, the surgeon again selects a mobile bearing trial 374 for the trial reduction. As shown in FIG. 40, the tibial tray 564 of the mobile bearing knee prosthesis 560 is installed in the proximal end 604 of the patient's tibia 606. A trial stem 680 is positioned in the bore 574 of the tibial tray 564 to approximate the function of the stem 586 of the mobile bearing 566. The upper end 682 is configured to be received in the central passageway 222 of the shim 190 while the lower end 684 is seated in the bore 574.

The surgeon attaches the mobile bearing surface trial 340 to the shim 190 to assemble to the mobile bearing trial 374 and positions the mobile bearing trial 374 over the tibial tray 564. The surface 196 of the shim 190 is then advanced into contact with the upper surface 576 of the tibial tray 564. When properly seated, the upper end 682 of the trial stem 680 is received in the central passageway 222 of the shim 190.

With the mobile bearing trial 374 in place on the tibial tray 564, the knee is again extended and the surgeon may note the anteroposterior stability, medial-lateral stability, and overall alignment in the A/P and M/L planes. Overall alignment can be confirmed by attaching alignment rods 662, 664 to the handle 26. If there is any indication of instability, the surgeon may remove the mobile bearing trial 374 from the tibial tray 564 using the removal tool 626 and disassemble the trial 372 using the separator tool 640 to exchange the shim 190 or the bearing surface trial 192. The surgeon may then repeat the trial reduction until satisfied with the alignment and the stability of the knee.

When the additional trial reduction of block 716 is complete, or if the surgeon determines in block 715 that an additional trial reduction is not needed, the procedure 700 continues to block 718 in which the surgeon installs the selected tibial bearing. The surgeon may then continue with other parts of the surgical procedure.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method of trialing prosthetic components of a knee prosthesis, the method comprising
positioning a polymer femoral trial component on a surgically-prepared distal end of a patient's femur,
assembling a tibial bearing trial component,
positioning the tibial bearing trial component on a tibial base trial component seated on a surgically-prepared proximal end of a patient's tibia,
adjusting the patient's leg with the tibial bearing trial component engaging the polymer femoral trial component,
removing the tibial bearing trial component from the tibial base trial component,
inserting a keel punch into the surgically-prepared proximal end of the patient's tibia through an opening of the tibial base trial component,
placing the tibial bearing trial component on the tibial base trial component and the keel punch, and
readjusting the patient's leg with the tibial bearing trial component engaging the polymer femoral trial component after positioning the tibial bearing trial component on the tibial base trial component and the keel punch.

2. The method of claim 1, wherein adjusting the patient's leg includes moving the patient's leg between extension and flexion such that a plurality of teeth of the polymer femoral trial component grip the surgically-prepared distal end of the patient's femur.

3. The method of claim 1, further comprising inserting a base insert into the opening of the tibial base trial component before positioning the tibial bearing trial component on the tibial base trial component.

4. The method of claim 3, wherein
assembling the tibial bearing trial component includes securing a shim to a first tibial bearing surface trial component in a first orientation, and
positioning the tibial bearing trial component includes positioning a lug of the base insert in a first slot of the shim such that the tibial bearing trial component is prevented from substantially rotating relative to the tibial base trial component.

5. The method of claim 4, wherein placing the tibial bearing trial component on the tibial base trial component and the keel punch includes positioning a lug of the keel punch in the first slot of the shim such that the tibial bearing trial component is prevented from substantially rotating relative to the tibial base trial component.

6. The method of claim 4, wherein
assembling the tibial bearing trial component includes securing the shim to a second tibial bearing surface trial component in a second orientation,
positioning the tibial bearing trial component includes positioning the lug of the base insert in a second slot of the shim such that the tibial bearing trial component is permitted to substantially rotate relative to the tibial base trial component, and
adjusting the patient's leg includes rotating the tibial bearing trial component relative to the tibial base trial component.

7. The method of claim 6, wherein inserting the base insert includes inserting a spike of the base insert into the patient's tibia.

8. The method of claim 6, wherein
placing the tibial bearing trial component on the tibial base trial component and the keel punch includes positioning a lug of the keel punch in the second slot of the shim such that the tibial bearing trial component is permitted to substantially rotate relative to the tibial base trial component, and
readjusting the patient's leg includes rotating the tibial bearing trial component relative to the tibial base trial component.

9. The method of claim 1, further comprising
placing a guide tower on the tibial base trial component, and
securing the keel punch to a lower end of a handle by engaging a lever of the handle with the keel punch,
wherein inserting the keel punch into the surgically-prepared proximal end of the patient's tibia includes inserting the keel punch and the lower end of the handle through an upper end of the guide tower.

10. The method of claim 9, wherein positioning the polymer femoral trial component includes
securing an impactor head to the handle,
attaching the polymer femoral trial component to the impactor head, and
tapping a head end of the handle to attach the polymer femoral trial component to the surgically-prepared distal end of the patient's femur.

11. The method of claim 1, further comprising
installing a tibial tray of the knee prosthesis in the surgically-prepared proximal end of the patient's tibia,
positioning the tibial bearing trial component on the tibial tray, and
readjusting the patient's leg after positioning the tibial bearing trial component on the tibial tray.

12. A method of trialing prosthetic components of a knee prosthesis, the method comprising
positioning a femoral trial component on a surgically-prepared distal end of a patient's femur,
selecting (i) a first femoral prosthetic component if a sidewall of the femoral trial component is positioned beyond an outer edge of the surgically-prepared distal end of the patient's femur and the surgically-prepared distal end of the patient's femur is visible through a notch defined in the sidewall of the femoral trial component, and (ii) a second femoral prosthetic component if the sidewall of the femoral trial component is positioned within the outer edge of the surgically-prepared distal end of the patient's femur, the first femoral prosthetic component being more narrow than the second femoral prosthetic component,
positioning a tibial bearing trial component on a tibial base trial component seated on a surgically-prepared proximal end of a patient's tibia,
adjusting the patient's leg with the tibial bearing trial component engaging the femoral trial component, removing the tibial bearing trial component from the tibial base trial component,
inserting a keel punch into the surgically-prepared proximal end of the patient's tibia through an opening of the tibial base trial component,
positioning the tibial bearing trial component on the tibial base trial component and the keel punch, and
readjusting the patient's leg with the tibial bearing trial component engaging the femoral trial component after positioning the tibial bearing trial component on the tibial base trial component and the keel punch.

13. The method of claim 12, wherein the femoral trial component is formed from a polymeric material.

14. The method of claim 12, further comprising
selecting a tibial bearing surface trial component from a plurality of tibial bearing surface trial components,
orienting a shim relative to the tibial bearing surface trial component, and
securing the shim to the tibial bearing surface trial component to assemble the tibial bearing trial component,
wherein (i) the shim is secured in a first orientation relative to the tibial bearing surface trial component if the tibial bearing surface trial component is a first tibial bearing surface trial component, and (ii) the shim is secured in a second orientation that is opposite the first orientation if the tibial bearing surface trial component is a second tibial bearing surface trial component.

15. The method of claim 14, wherein the tibial bearing surface trial component is the first tibial bearing surface trial component adjusting the patient's leg includes rotating the tibial bearing trial component relative to the tibial base trial component.

16. A method of trialing prosthetic components of a knee prosthesis, the method comprising
positioning a femoral trial component on a surgically-prepared distal end of a patient's femur,
selecting (i) a first femoral prosthetic component if a sidewall of the femoral trial component is positioned beyond an outer edge of the surgically-prepared distal end of the patient's femur and the surgically-prepared distal end of the patient's femur is visible through a notch defined in the sidewall of the femoral trial component, and (ii) a second femoral prosthetic component if the sidewall of the femoral trial component is positioned within the outer edge of the surgically-prepared distal end of the patient's femur, the first femoral prosthetic component being more narrow than the second femoral prosthetic component,
selecting a tibial bearing surface trial component from a plurality of tibial bearing surface trial components,
selecting a shim that includes a first surface configured to face the tibial bearing surface trial component when the shim is placed in a first orientation and a second surface configured to face the tibial bearing surface trial component when the shim is placed in a second orientation,
orienting the shim relative to the tibial bearing surface trial component in one of the first orientation and the second orientation based on the selected tibial bearing surface trial component,
securing the shim to the tibial bearing surface trial component to assemble the tibial bearing trial component, positioning the tibial bearing trial component on a tibial base trial component seated on a surgically-prepared proximal end of a patient's tibia, and adjusting the patient's leg with the tibial bearing trial component engaging the femoral trial component, wherein (i) the shim is secured in the first orientation relative to the tibial bearing surface trial component when the selected tibial bearing surface trial component is a first tibial bearing surface trial component, and (ii) the shim is secured in the second orientation that is opposite the first orientation when the selected tibial bearing surface trial component is a second tibial bearing surface trial component that is different from the first tibial bearing surface trial component, wherein (i) the tibial bearing trial component is permitted to rotate relative to the tibial base trial component when the shim is secured to the tibial bearing surface trial component in the first orientation and (ii) the tibial bearing trial component is substantially prevented from rotating relative to the tibial base trial component when the shim is secured to the tibial bearing surface trial component in the second orientation.

17. The method of claim 16, further comprising drilling a pair of fixation holes in the surgically-prepared distal end of the patient's femur.

18. The method of claim 17, wherein drilling the pair of fixation holes includes inserting a surgical drill into two guide holes defined in the polymer femoral trial component.

* * * * *